US012780896B2

(12) United States Patent
Li et al.

(10) Patent No.: US 12,780,896 B2
(45) Date of Patent: Nov. 3, 2026

(54) COMBINED EXPRESSION OF A CHIMERIC CD3 FUSION PROTEIN AND AN ANTI-CD3-BASED BISPECIFIC T CELL ACTIVATING ELEMENT

(71) Applicant: BIOTHEUS (SUZHOU) CO., LTD., Suzhou (CN)

(72) Inventors: Zhiyuan Li, Suzhou (CN); Gang Yi, Suzhou (CN); Andy Tsun, Zhuhai (CN); Xiaolin Liu, Zhuhai (CN); Weifeng Huang, Suzhou (CN); Shaogang Peng, Suzhou (CN)

(73) Assignee: BIOTHEUS (SUZHOU) CO., LTD., Suzhou (CN)

( * ) Notice: Subject to any disclaimer, the term of this patent is extended or adjusted under 35 U.S.C. 154(b) by 1273 days.

(21) Appl. No.: 17/642,570

(22) PCT Filed: Sep. 7, 2020

(86) PCT No.: PCT/IB2020/058302

§ 371 (c)(1),
(2) Date: Mar. 11, 2022

(87) PCT Pub. No.: WO2021/048724

PCT Pub. Date: Mar. 18, 2021

(65) Prior Publication Data

US 2022/0331416 A1 Oct. 20, 2022

(30) Foreign Application Priority Data

Sep. 12, 2019 (CN) ......................... 201910866695.4

(51) Int. Cl.

| | |
|---|---|
| ***A61K 39/00*** | (2006.01) |
| ***A61K 40/11*** | (2025.01) |
| ***A61K 40/31*** | (2025.01) |
| ***A61K 40/42*** | (2025.01) |
| ***A61P 35/00*** | (2006.01) |
| ***C07K 14/705*** | (2006.01) |
| ***C07K 16/28*** | (2006.01) |
| ***C07K 16/30*** | (2006.01) |
| ***C07K 16/32*** | (2006.01) |
| ***C12N 5/0783*** | (2010.01) |

(52) U.S. Cl.

CPC .......... *C07K 14/7051* (2013.01); *A61K 40/11* (2025.01); *A61K 40/31* (2025.01); *A61K 40/4205* (2025.01); *A61K 40/4244* (2025.01); *A61P 35/00* (2018.01); *C07K 16/2809* (2013.01); *C07K 16/30* (2013.01); *C07K 16/32* (2013.01); *C12N 5/0636* (2013.01); *C12N 5/0638* (2013.01)

(58) Field of Classification Search

None

See application file for complete search history.

(56) References Cited

U.S. PATENT DOCUMENTS

| | | | | |
|---|---|---|---|---|
| 7,446,190 B2 * | 11/2008 | Sadelain | ............ | C07K 14/7051 536/23.53 |
| 9,499,629 B2 * | 11/2016 | June | ..................... | C12N 5/0636 |
| 9,683,985 B2 * | 6/2017 | Kodandapani | ..... | G01N 33/5011 |
| 2023/0002503 A1 * | 1/2023 | Miao | ...................... | C07K 16/30 |

FOREIGN PATENT DOCUMENTS

| | | | | |
|---|---|---|---|---|
| CN | 107227299 A | 10/2017 | | |
| CN | 108424458 A | 8/2018 | | |
| CN | 108424461 A | 8/2018 | | |
| CN | 109306014 A | 2/2019 | | |
| JP | 2018-536434 A | 12/2018 | | |
| WO | 2009/025846 A2 | 2/2009 | | |
| WO | 2016/054520 A2 | 4/2016 | | |
| WO | WO2016/054520 * | 4/2016 | ........... | C07K 14/725 |
| WO | 2016/070061 A1 | 5/2016 | | |
| WO | 2019/110815 A1 | 6/2019 | | |
| WO | 2019/157533 A1 | 8/2019 | | |

OTHER PUBLICATIONS

Clevers et al. (Proc. Natl. Acad. Sci. U.S.A. 85, 8156-8160, 1988).*
Huehls et al. (Immunology and Cell Biology, 2015, p. 290-296).*
Notice of Reasons for Refusal directed to Japanese Patent Application No. 2022-516428 mailed on Aug. 20, 2024, 5 pages.
European Search Report dated Oct. 24, 2023, directed to European Application No. 20863564.9, 9 pages.
Choi, Byran D. et al., "CAR-T cells secreting BiTEs circumvent antigen escape without detectable toxicity", Nature Biotechnology, vol. 37, No. 9, Jul. 22, 2019 (Jul. 22, 2019), pp. 1049-1058.
International Search Report and Written Opinion mailed Dec. 18, 2020, directed to International Application No. PCT/IB2020/058302; 11 pages.
Jiang, W. et al., (Oct. 2010). "Anti-tumor Effects of the Combined Administration of Fusion Protein Based on 4-1BBL and CD3 Signals," in Biotechnology Bulletin No. 10; pp. 205-209.
Märklin, M. et al., (May 2019). "Bispecific NKG2D-CD3 and NKG2D-CD16 fusion proteins for induction of NK and T cell reactivity against acute myeloid leukemia," in Journal for Immunotherapy for Cancer, vol. 7: No. 143; 15 pages.

(Continued)

*Primary Examiner* — Agnieszka Boesen

(74) *Attorney, Agent, or Firm* — Michele V. Frank; Keith G. Haddaway; Venable LLP

(57) ABSTRACT

Provided is a nucleic acid encoding a chimeric CD3 fusion protein and an anti-CD3 based bispecific T cell activator (BiTA) element. Also provided are vectors, engineered immune cells comprising the nucleic acid, the usage thereof and methods for preventing tumor. BiTA secreted by CAB-T cells can simultaneously achieve activation of CAB-T cells and endogenous TCR complexes in non-engineered T cells in tumor, and exert an anti-tumor effect.

26 Claims, 17 Drawing Sheets

Specification includes a Sequence Listing.

(56) References Cited

OTHER PUBLICATIONS

First Examination Report Notification from Chinese Patent Application No. 202080064132.4 dated Nov. 28, 2024, 16 pages.
Office Action dated Jan. 16, 2024, directed to Canadian Patent Application No. 3,150,839; 7 pages.
Mestermann, K. et al., (Jul. 3, 2019). "The tyrosine kinase inhibitor dasatinib acts as a pharmacologic on/off switch for CAR T cells," Science Translational Medicine, 11(499); 11 pages.

* cited by examiner

COMBINED EXPRESSION OF A CHIMERIC CD3 FUSION PROTEIN AND AN ANTI-CD3-BASED BISPECIFIC T CELL ACTIVATING ELEMENT

CROSS-REFERENCE TO RELATED APPLICATIONS

This application is a National Stage Application under 35 U.S.C. § 371 PCT/IB2020/058302, filed Sep. 7, 2020, which claims priority benefit from Chinese Patent Application No. 201910866695.4, filed on Sep. 12, 2019, the entire contents of each of which is incorporated herein by reference.

BACKGROUND

Sequence Listing

The instant application contains a Sequence Listing which has been filed electronically in ASCII format and is hereby incorporated by reference in its entirety. Said ASCII copy, created on May 5, 2022, is named 141279_560320_SL.txt and is 153,699 bytes in size.

TECHNICAL FIELD

The present disclosure relates generally to immunotherapy, and in particular, the present disclosure relates to the combined expression of a chimeric CD3 fusion protein and an anti-CD3-based bispecific T cell activating element.

RELATED ART

In recent years, immunotherapy has achieved unprecedented success in the complete remission rate of hematological tumors. In 2017, two CAR-T products targeting CD19 have been successfully marketed and approved for the treatment of acute leukemia and Non-Hodgkin lymphomas in children and adolescents, respectively.

However, there are two major problems associated with immunotherapy for treating solid tumors: on the one hand, the serious and even fatal clinical side effects associated with CAR-T therapy, which mainly include cytokine release syndrome (CRS), macrophage activation syndrome, neurotoxicity, etc., remain a great risk for clinical application of CAR-T therapy. Furthermore, CAR-T therapy has not yet demonstrated significant clinical efficacy in the clinical treatment of solid tumors.

WO2016070061 to Zhao et al. describes engineered T cells expressing a bispecific antibody and a chimeric ligand engineered activation receptor (CLEAR). However, Zhao's disclosure is limited to receptor/ligand targets PD1/PD-L1 and CD27/CD70 and the expression of PD1 or CD27 CLEARs.

WO2016/054520 to Kim et al. describes effector cells expressing engineered cell surface protein and using the effector cell for the treatment of diseases. And in one of their embodiment, the combination therapy of effector cells with engineered CD3e expression and bispecific T cell engager (BiTE) was described. However, in the method of Kim, CD3e and the BiTEs are not co-expressed in a single effector cell, and continuous low dose infusion is required due to the low PK half-life and toxicity of BiTEs. Independent administration of these effector cells and BiTEs does not result in synergy in the solid tumor microenvironment.

Therefore, there is still a need to develop a therapeutic regimen for inhibiting solid tumors with good clinical efficacy and low clinical side effects.

SUMMARY

It is an object of the present disclosure to provide a treatment regimen for inhibiting solid tumors with good clinical efficacy and minimized clinical side-effects.

A first aspect of the present disclosure provides a DNA construct encoding a chimeric CD3 fusion protein (e.g., chimeric CD3e fusion protein), and an anti-CD3-based bispecific T cell activating element.

In a preferred embodiment, the chimeric CD3 is fusion protein that comprises one or more polypeptide that is recognizable by an anti-CD3 antibody, and optionally one or more of the following: a transmembrane domain (TM), a co-stimulatory domain and CD3 signal activation domains, such as a CD3ζ domain.

In a preferred embodiment, the anti-CD3-based bispecific T cell activating element is a fusion protein that comprises one or more tumor antigen recognition domain and one or more anti-CD3 antibody fragment(s), including for example, a single domain antibody sequence (VHH), a single-chain antibody variable region sequence (scFv), and/or an antigen-binding fragment (Fab) that targets CD3. In a preferred embodiment, the chimeric CD3 fusion protein has a structure shown in the following formula I:

$$\text{L-EC-H-TM-C-CD3}\zeta \qquad \text{(I)}$$

In the formula,

- L is absent or a signal peptide sequence;
- EC is a polypeptide binding domain from or derived from a CD3e protein, that is recognizable by an anti-CD3 antibody and binds to the anti-CD3 antibody;
- the polypeptide binding domain is also referred to as a recognition binding domain of the anti-CD3 antibody;
- the polypeptide binding domain is also referred to as a subunit of recognition binding domain of the anti-CD3 antibody;
- H is absent or a linker or a hinge region;
- TM is a transmembrane domain;
- C is absent or a costimulatory signaling molecule;
- CD3ζ is absent or a cytoplasmic signaling sequence derived from CD3ζ;
- each "—" is independently a linker peptide or a peptide bond.

In another preferred embodiment, the L is a signal peptide of a protein selected from the following group: CD8, GM-CSFR (DNA SEQ ID NO.: SEQ 1, AA SEQ ID NO.: SEQ 2), CD4, CD137, or a combination thereof.

In another preferred embodiment, the polypeptide binding domain is a CD3e extracellular region or a portion thereof recognizable by an anti-CD3 antibody.

In another preferred embodiment, the anti-CD3 antibody is selected from the following group: an scFV (single-chain antibody), a single domain antibody sequence (also known as a nanobody or VHH), a diabody, or a variant thereof, or a combination thereof.

In another preferred embodiment, a clone of the anti-CD3 antibody comprises L2K (DNA SEQ ID NO.: SEQ 19, AA SEQ ID NO.: SEQ 20), UCHT1, OKT3, F6A, I2C or a combination thereof. In another preferred embodiment, the polypeptide binding domain specifically recognizes and binds to an anti-CD3 antibody, which may be present as a segment of a bispecific antibody.

In another preferred embodiment, EC comprises or consists of position 1 to 104 of a wild type or mutant CD3e protein, and the amino acid sequence thereof is shown in SEQ ID NO.: SEQ 4.

In another preferred embodiment, H is a linker or a hinge region of a protein selected from the following group: CD8 (DNA SEQ ID NO.: SEQ 5, AA SEQ ID NO.: SEQ 6), CD28 (DNA SEQ ID NO.: SEQ 57, AA SEQ ID NO.: SEQ 58), CD137, or a combination thereof.

In another preferred embodiment, the TM is a transmembrane region of a protein selected from the following group: CD28 (DNA SEQ ID NO.: SEQ 59, AA SEQ ID NO.: SEQ 60), CD3 epsilon, CD45, CD4, CD5, CD8 (DNA SEQ ID NO.: SEQ 7, AA SEQ ID NO.: SEQ 8), CD9, CD16, CD22, CD33, CD37, CD64, CD80, CD86, CD134, CD137, CD154, or a combination thereof.

In another preferred embodiment, C is a costimulatory signal molecule of a protein selected from the following group: OX40, CD2, CD7, CD27, CD28, CD30, CD40, CD70, CD134, 4-1BB (CD137), PD1, Dap10, CDS, ICAM-1, LFA-1 (CD11a/CD18), ICOS (CD278), NKG2D, GITR, TLR2, or a combination thereof.

In another preferred embodiment, C comprises a 4-1BB-derived costimulatory signal molecule (DNA SEQ ID NO.: SEQ 9, AA SEQ ID NO.: SEQ 10), and/or a CD28-derived costimulatory signal molecule (DNA SEQ ID NO.: SEQ 61, AA SEQ ID NO.: SEQ 62).

In another preferred embodiment, CD3ζ is a cytoplasmic signaling sequence as represented by AA SEQ ID NO. NO.: 12.

In another preferred embodiment, the DNA construct is expressed in a cis or fusion form with a safety switch protein, and proteins capable of serving as a safety switch comprise: inducible Caspase 9 (iCasp9), CD19, CD20, EGFR, HER2, CD30, CD19, c-Met, Claudin 18.2, or a combination thereof.

In another preferred embodiment, the anti-CD3-based bispecific T cell activating element (BiTA) has a structure shown in the following formula II:

L'-T1-B1-B2-T2 (II)

In the formula,

- L' is absent or a signal peptide sequence;
- T1 is absent or a tag element;
- B1 is a tumor antigen recognition region or a CD3 antigen recognition region;
- B2 is a CD3 antigen-binding antibody fragment or a tumor antigen recognition region;
- T2 is absent or a tag element;
- each "—" is independently a linker peptide or peptide bond.

In another preferred embodiment, L' is a signal peptide of a protein selected from the following group: CD8, GM-CSFR, CD4, CD137, or a combination thereof.

In another preferred embodiment, the tag element comprises a tag protein, a fluorescein labeled protein or an enzyme labeled protein.

In another preferred embodiment, the tag protein comprises a FLAG protein (DNA SEQ ID NO.: SEQ 13, AA SEQ ID NO.: SEQ 14), and His protein (DNA SEQ ID NO.: SEQ 35, AA SEQ ID NO.: SEQ 36).

In another preferred embodiment, B1 is a tumor antigen recognition region and B2 is a CD3 antigen recognition region.

In another preferred embodiment, the tumor antigen recognition region comprises of one or more receptor or ligand binding domains, an antibody fragment, including single domain antibody sequence (VHH), and/or single-chain antibody variable region sequence (scFv), and/or a TCR sequence.

In another preferred embodiment, the tumor antigen is selected from the following group: TSHR, CD19, CD123, CD22, CD30, CD171, CS-1, CLL-1, CD33, EGFRvIII, GD2, GD3, BCMA, Tn Ag, PSMA, ROR1, FLT3, FAP, TAG72, CD38, CD44v6, CEA, EPCAM, B7H3, KIT, IL-13Ra2, Mesothelin, IL-11Ra, PSCA, PRSS21, VEGFR2, LewisY, CD24, PDGFR-β, SSEA-4, CD20, folate receptor alpha, ERBB2 (Her2/neu), MUC1, EGFR, NCAM, Prostase, PAP, ELF2M, ephrin B2, IGF-I receptor, CAIX, LMP2, gp100, bcr-abl, tyrosinase, EphA2, fucosyl GM1, sLe, GM3, TGS5, HMWMAA, o-acetyl-GD2, folate receptor β, TEM1/CD248, TEM7R, CLDN6, GPRC5D, CXORF61, CD97, CD179a, ALK, polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, MAGE-A1, legumain, HPV E6, E7, MAGE A1, ETV6-AML, sperm protein 17, XAGE1, Tie 2, MAD-CT-1, MAD-CT-2, Fos-associated antigen 1, p53, p53 mutant, prostein, survivin and telomerase, PCTA-1/Galectin 8, MelanA/MART1, Ras mutant, hTERT, sarcoma translocation breakpoint, ML-IAP, ERG (TMPRSS2ETS fusion gene), NA17, PAX3, androgen receptor, cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxylesterase, mut hsp70-2, CD79a, CD79b, CD72, LAIR1, FCAR, LILRA2, CD300LF, CLEC12A, BST2, EMR2, LY75, GPC3, FCRL5, IGLL1, DLL3 or a combination thereof.

In another preferred embodiment, the tumor antigen recognition region targets CAIX and/or HER2.

In another preferred embodiment, the tumor antigen recognition region is a VHH antibody (DNA SEQ ID NO.: SEQ 17, AA SEQ ID NO.: SEQ 18) targeting CAIX.

In another preferred embodiment, the tumor antigen recognition region is a single-chain antibody (DNA SEQ ID NO.: SEQ 65, AA SEQ ID NO.: SEQ 66) targeting HER2.

In another preferred embodiment, the CD3 antigen-binding antibody fragment is a single domain antibody sequence (VHH), a single-chain antibody variable region sequence (scFv), or an antigen-binding fragment (Fab) that targets CD3.

In another preferred embodiment, the BiTA is a secreted BiTA.

In another preferred embodiment, the BiTA targets CAIX (DNA SEQ ID NO.: SEQ 21, AA SEQ ID NO.: SEQ 22), or targets HER2 (DNA SEQ ID NO.: SEQ 49, AA SEQ ID NO.: SEQ 50).

In another preferred embodiment, the secreted BiTA may be autocrine, and/or paracrine.

In another preferred embodiment, the secretory cell type of the secreted BiTA may be: a T cell, an NK cell, a macrophage, a B cell, a red blood cell, or a combination thereof.

In another preferred embodiment, the secretory cell type of the secreted BiTA is a T cell.

In another preferred embodiment, the BiTA can bind to chimeric CD3e.

In another preferred embodiment, the BiTA can bind to the T cell receptor (TCR) complex.

In another preferred embodiment, the TCR is derived from a T cell according to the fifth aspect, and/or a T cell that has not been engineered.

In another preferred embodiment, the nucleic acid molecule encoding the chimeric CD3 fusion protein and the nucleic acid molecule encoding the bispecific T cell activating element are provided separately. Advantageously, the nucleic acid molecule encoding the chimeric CD3 fusion protein and the nucleic acid molecule encoding the bispecific T cell activating element are co-expressed in the same immune cell.

A second aspect of the invention provides a vector, characterized in that the vector comprises the nucleic acid molecule.

In another preferred embodiment, the vector is selected from the group consisting of lentiviral, adenoviral, and retroviral vectors.

A third aspect of the invention provides a genetically engineered immune cell (e.g. T cell), characterized in that the immune cell expresses the nucleic acid molecules as described above. In an optionally embodiment, the immune cell is engineered to express the chimeric CD3 fusion protein and the bispecific T cell activating element, whereby the nucleic acid molecule encoding the chimeric CD3 fusion protein and the nucleic acid molecule encoding the bispecific T cell activating element are not provided on the same DNA construct.

In another preferred embodiment, the T cell is derived from a person or a non-human mammal.

In another preferred embodiment, the T cell further comprises other chimeric antigens.

A fourth aspect of the present disclosure provides a composition, characterized in that the composition comprises the fusion protein and BiTA.

In another preferred embodiment, the fusion protein in the composition is located in the extracellular region of a T cell membrane.

In another preferred embodiment, the BiTA in the composition is autocrine, paracrine or exogenous BiTA.

In another preferred embodiment, the composition is expressed in the form of a fusion protein of the structural formula I and the structural formula II with a 2A protein, the structural formula of which is: I-2A-II or II-2A-I, and the sequence of 2A includes one of T2A (DNA SEQ ID NO.: SEQ 23, AA SEQ ID NO.: SEQ 24), P2A, F2A or E2A or a combination thereof.

In another preferred embodiment, the I-2A-II structure is a sequence that targets CAIX (DNA SEQ ID NO.: SEQ 25, AA SEQ ID NO.: SEQ 26) or HER2 (DNA SEQ ID NO.: SEQ 49, AA SEQ ID NO.: SEQ 50).

In another preferred embodiment, the II-2A-I structure is a sequence that targets CAIX or HER2 (DNA SEQ ID NO.: SEQ 67, AA SEQ ID NO.: SEQ 68).

In another preferred embodiment, the I-2A-II or II-2A-I structure is expressed in a cis or fusion form with a safety switch protein, and proteins capable of serving as a safety switch comprise: inducible Caspase 9 (iCasp9), CD19, CD20, EGFR, HER2, CD30, CD19, c-Met, Claudin 18.2, or a combination thereof.

In another preferred embodiment, the composition is expressed in the form of a combination of a fusion protein of the structural formula I and the structural formula II with an IRES sequence, the structural formula of which is: I-IRES-II or II-IRES-I, IRES is a nucleotide sequence internal ribosome entry site.

In another preferred embodiment, the IRES functions as initiating amino acid translation of a downstream gene.

In another preferred embodiment, the I-IRES-II or II-IRES-I structure is expressed in a cis or fusion form with a safety switch protein, and proteins capable of serving as a safety switch comprise: inducible Caspase 9 (iCasp9), CD19, CD20, EGFR, HER2, CD30, CD19, c-Met, Claudin 18.2, or a combination thereof.

A fifth aspect of the present disclosure provides a non-naturally occurring T cell population. The T cells as described above are present in the T cell population at a ratio C1 of 10% or more, based on the total number of T cells in the T cell population.

In another preferred embodiment, the C1 is 10% or more, preferably C1≥20%, and more preferably C1≥30%.

In another preferred embodiment, BiTA, and/or BiTA-secreting T cells C2 are also present in the T cell population.

A sixth aspect of the present disclosure provides a composition, comprises (a) the genetically engineered T cells as described above and/or the T cell population as described above, and (b) a pharmaceutically acceptable carrier, diluent and/or excipient.

A seventh aspect of the present disclosure relates to the use of the genetically engineered T cells, the T cell population, and/or the composition as described above in the preparation of a medicament for the prevention and/or treatment of cancer or tumors, or for use in a method as described below.

An eighth aspect of the present disclosure provides a method for preventing or treating a disease, comprising: administering an appropriate amount of the genetically engineered T cells, the T cell population, and/or the composition according as described above to a subject in need of treatment.

In another preferred embodiment, the disease is cancer or a tumor.

In another preferred embodiment, the tumor is selected from the following group: a hematological tumor, a solid tumor, and a combination thereof.

In another preferred embodiment, the hematological tumor is selected from the following group: acute myelocytic leukemia (AML), multiple myeloma (MM), chronic lymphocytic leukemia (CLL), acute lymphocytic leukemia (ALL), diffuse large B cell lymphoma (DLBCL), and a combination thereof.

In another preferred embodiment, the solid tumor is selected from the following group: gastric cancer, peritoneal metastasis in gastric cancer, liver cancer, leukemia, kidney tumor, lung cancer, small intestine cancer, bone cancer, prostate cancer, colorectal cancer, breast cancer, colon cancer, cervical cancer, ovarian cancer, lymphoma, nasopharyngeal carcinoma, adrenal tumor, bladder tumor, non-small cell lung cancer (NSCLC), glioma, endometrial cancer, testicular cancer, urinary tract tumor, thyroid cancer and a combination thereof.

In another preferred embodiment, the solid tumor is selected from the following group: ovarian cancer, mesothelioma, lung cancer, pancreatic cancer, breast cancer, liver cancer, endometrial cancer, or a combination thereof. In another preferred embodiment, the method further comprises administering an appropriate amount of a cytokine secreted by a stimulating cell or drug compound and a composition thereof to enhance the responsiveness of an immune cell.

In an embodiment, the method further comprises the step of administering dasatinib to the subject.

In another preferred embodiment, the immune cell comprises the T cell, the T cell population, and/or the composition as described above, and an endogenous T cell, NK cell, macrophage and B cell.

A ninth aspect of the present disclosure provides a method of reducing the toxicity of an immune cell engineered with a chimeric CD3e fusion protein and a bispecific T cell activating element, comprising the administration of dasatinib; as well as the use of dasatinib in the preparation of a medicament for reducing the toxicity of an immune cell engineered with a chimeric CD3e fusion protein and a bispecific T cell activating element.

It is to be understood that within the scope of the present disclosure, the various technical features of the present disclosure as described above and the various technical features specifically described hereinafter (e.g. in the examples) may be combined with each other to constitute a new or preferred technical solution.

DETAILED DESCRIPTION

Figure 1:
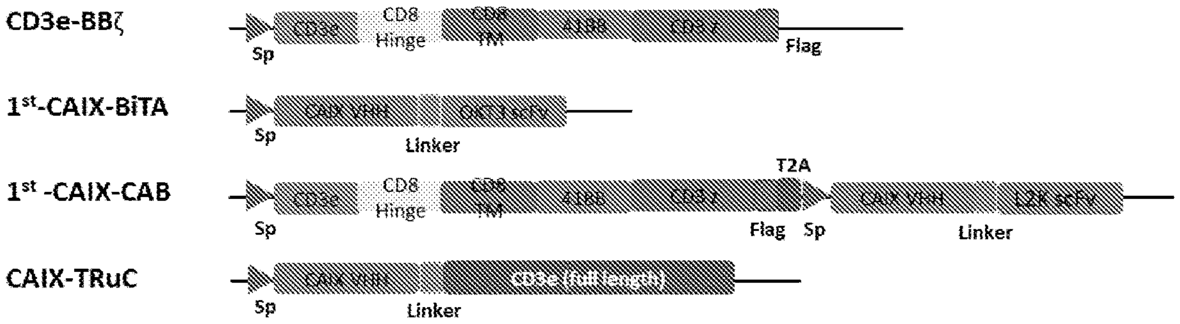
FIG. 1 shows the structures of CAB-T according to a first group of experiments and its control group.

The present disclosure relates to an immunotherapeutic regimen for inhibiting tumors, particularly solid tumors, involving the use of T cells expressing a chimeric CD3 fusion protein, preferably a chimeric CD3e fusion protein, with an anti-CD3 antibody-based bispecific T cell activator (BiTA), similar to a bispecific T-cell engager (BiTE). The chimeric CD3 fusion protein and BiTA with a CD3 antigen recognition site bind to each other and function to activate T cells and target tumor cells expressing tumor associated antigens (TAA). The present disclosure also provides a CAB structure and CAB-engineered T cells (CAB-T) expressing chimeric CD3 and an anti-CD3 antibody-based bispecific T cell activator. BiTA secreted by the CAB-T cells can simultaneously activate CAB-T cells and the endogenous TCR complex of non-engineered and engineered T cells in tumor tissues, exert the anti-tumor effect of CAB-T itself and mobilize the anti-tumor effect of the non-engineered T cells, thereby ensuring the effectiveness of this CAB-T technology for clinical application. The chimeric CD3 construct that is expressed by CAB-T and BiTA act synergistically to exert its antitumor effects: activation of the chimeric CD3 element is dependent on BiTA secreted by CAB-T, and the secretion of BiTA further stimulates CAB-T to secrete BiTA by activating the chimeric CD3 element, so that immune cell activation and anti-tumor effects are localized to the tumor microenvironment and the safety advantage of this CAB-T technology for clinical application is ensured.

Description of Terms

Unless defined otherwise, all technical and scientific terms used herein have the same meaning as commonly understood by one of ordinary skill in the art to which this present disclosure belongs.

As used herein, the term "about" when used in reference to a specifically recited value means that the value may vary by no more than 1% from the recited value. For example, as used herein, the expression "about 100" includes 99 and 101 and all values there between (e.g., 99.1, 99.2, 99.3, 99.4, etc.).

As used herein, the term "contain" or "include (comprise)" can be open, semi-closed, and closed. In other words, the term also includes "consisting essentially of . . . " or "consisting of . . . ".

The term "administering" refers to the physical introduction of a product of the present disclosure into a subject using any of a variety of methods and delivery systems known to those skilled in the art, including intravenous, intramuscular, subcutaneous, intraperitoneal, spinal cord or other parenteral routes of administration, e.g., by injection or infusion.

The term "antibody" (Ab) shall include, but not limited to, an immunoglobulin that specifically binds to an antigen and comprises at least two heavy (H) chains and two light (L) chains interconnected by disulfide bonds, or an antigen binding fragment thereof. Each H chain comprises a heavy chain variable region (abbreviated as VH herein) and a heavy chain constant region. The heavy chain constant region comprises three constant domains: CH1, CH2 and CH3. Each light chain comprises a light chain variable region (abbreviated as VL herein) and a light chain constant region. The light chain constant region comprises a constant domain CL. The VH and VL regions can be further subdivided into hypervariable regions called complementary determining regions (CDRs), and the hypervariable regions are interspersed with more conserved regions called framework regions (FRs). Each of VH and VL contains three CDRs and four FRs, arranged from the amino end to the carboxyl end in the following order: FR1, CDR1, FR2, CDR2, FR3, CDR3, and FR4. The variable regions of the heavy and light chains contain a binding domain that interacts with the antigen.

It should be understood that the amino acid names herein are given by the international single English letter designation, and three-English-letter abbreviations corresponding to the amino acid names respectively are: Ala (A), Arg (R), Asn (N), Asp (D), Cys (C), Gln (Q), Glu (E), Gly (G), His (H), Ile (I), Leu (L), Lys (K), Met (M), Phe (F), Pro (P), Ser (S), Thr (T), Trp (W), Tyr (Y) and Val (V).

Chimeric Antigen Receptor (CAR)

The structure of the chimeric antigen receptor (CAR) is a fusion protein based on the intracellular segment domain of a TCR complex CD3ζ and the intracellular activator domain from costimulatory signals CD28 or 4-1BB. Advantageously, T cells modified to express CAR are able to bind to target antigens in a MHC-independent manner, such that the activation of T cells does not depend on the presentation of antigens by MHC. This type of CAR is known as a second generation CAR structure, and two CAR-T drugs approved in 2017 belong to this structure type.

T Cell Receptor (TCR)

The T cell receptor (TCR) is the most complex receptor in the human body, and the interaction of six different receptor subunits together determines its broad signal transduction within T cells. The two chains of TCRα and TCRβ together recognize a complex composed of a polypeptide-histocompatibility complex, and the subunits that transmit TCR signals, collectively known as CD3, include: one heterodimer formed by CD3ε and CD3γ, one heterodimer formed by CD3ε and CD3δ, and one CD3ζ homodimer. All subunits of the TCR are type I transmembrane proteins and have immunoglobulin domains except for CD3ζ. The four different CD3 subunits in the TCR receptor complex have 10 immune receptor tyrosine-based activation motifs (ITAMs) in total, and can receive 20 tyrosine phosphate groups in total when the TCR receptor complex is activated. In transgenic mouse experiments, it is shown that changes in the proline rich region of the intracellular segment of CD3ε or the conformation of CD3ε play a crucial regulatory role in the delivery of intact TCRs. It has been demonstrated that TCR activity can be modulated by binding the ligand to TCRαβ and stabilizing the arrangement of the CD3 subunits, ligand-independent TCR oligomerization, and binding to cholesterol.

TRuC Structure

A novel T cell therapy platform, TRuC™, self-developed by $TCR^2$ is a chimeric antigen receptor consisting of an antibody-based target antigen recognition sequence and a TCR receptor subunit. The TRuC structure can reprogram a complete TCR complex that recognizes tumor antigens. Unlike the CAR structure, the TRuC structure can be integrated into the TCR complex to exert its function. TRuC-T has the same tumor killing activity as the second generation CAR-T; at the same time, TRuC-T cells release cytokine at a level significantly lower than that of CAR-T cells because of the absence of additional costimulatory signal domains (CD28 or 4-1BB). TRuC-T shows antitumor activity in both hematological and solid tumor transplantation models. At the same time, TRuC-T shows more potent anti-tumor activity compared to CAR-T in multiple tumor models.

T Cell Antigen Coupler (TAC)

A TAC (T cell antigen coupler) technology platform by Triumvira can induce a more potent anti-tumor response than CAR-T with lower toxicity by regulating endogenous TCR of the T cell. The TAC structure consists of three parts: 1. an extracellular antigen binding region; 2. a TCR-recruitment region of a CD3 single-chain antibody; 3. a CD4/CD8 co-receptor binding region. Preclinical experiments have shown that TAC-T technology can specifically bind tumor cells and produce cytotoxicity, and the activation of TAC-T cells is similar to the activation of normal T cells, avoiding the production of a large number of cytokines. In a mouse tumor transplant model, TAC-T shows a better activity than CAR-T against either a solid tumor or a hematological tumor. In addition, TAC-T is more capable of infiltrating into a tumor microenvironment in solid tumors.

Bispecific T Cell Engager (BiTE)

Blinatumomab, a bispecific T cell engager (BiTE) drug targeting CD19 and developed by Amgen, USA, was approved by FDA in 2014 for clinical treatment of acute leukemia. This antibody consists of two moieties: scFv that recognizes the CD19 antigen and scFv that recognizes the TCR complex (CD3e). After recognizing the target antigen CD19 in the tumor cell, the BiTE antibody can utilize the anti-CD3 scFv moiety to induce endogenous TCR oligomerization of T cells, thereby activating T cells and triggering tumor killing. The way by which BiTE treats tumors is similar to those of TRuC and TAC techniques, all of which cause endogenous TCR activation in T cells. Theoretically, the three have comparable abilities of activating endogenous TCR signals, and all have potential great value for mobilizing and redirecting T cells to treat solid tumors. However, due to the poor safety resulting from the systemic administration of BiTE drugs, the extremely short half-life of BiTE drugs in vivo, and the like, the use of BiTE in achieving a desirable efficacy in the clinical treatment of solid tumors has yet to be shown.

Bispecific T Cell Activator (BiTA) Structure

"Bispecific T cell activator structure", "bispecific T cell activating element", "BiTA", "bispecific T cell activator", and "-BiTA" stated herein refer to an anti-CD3-based bispecific T cell activator structure, which comprises of two moieties: (i) one or more tumor antigen recognition region(s), such as receptor or ligand binding domains, an antibody fragment, including single domain antibody sequence (VHH), a single-chain antibody variable region sequence (scFv), a antigen-binding fragment (Fab) and/or a T-cell receptor (TCR) sequence that recognizes a tumor antigen, and (ii) one or more CD3 antigen recognition regions, such as, an antibody fragment, including a single domain antibody sequence (VHH) that targets CD3, a single-chain antibody variable region sequence (scFv), or antigen-binding fragment (Fab).

In another preferred embodiment, the anti-CD3-based bispecific T cell activating element has a structure shown in the following formula II:

L'-T1-B1-B2-T2 (II)

In the formula,

L' is absent or a signal peptide sequence derived of a protein selected from the following group: CD8, CD4, CD137, or a combination thereof.

T1 is absent or a tag element, optionally comprising a tag protein, a fluorescein labeled protein or an enzyme labeled protein. Preferably, tag protein comprises a FLAG protein (DNA SEQ ID NO.: SEQ 13, AA SEQ ID NO.: SEQ 14), and His protein (DNA SEQ ID NO.: SEQ 35, AA SEQ ID NO.: SEQ 36).

B1 is a tumor antigen recognition region, optionally comprising receptor or ligand binding domains, a single domain antibody sequence (VHH), and/or a single-chain antibody variable region sequence (scFv), and/or an antibody Fab, and/or a T-cell receptor (TCR) sequence, which is/are able to recognize a tumor antigen selected from the following group: TSHR, CD19, CD123, CD22, CD30, CD171, CS-1, CLL-1, CD33, EGFRvIII, GD2, GD3, BCMA, Tn Ag, PSMA, ROR1, FLT3, FAP, TAG72, CD38, CD44v6, CEA, EPCAM, B7H3, KIT, IL-13Ra2, Mesothelin, IL-11Ra, PSCA, PRSS21, VEGFR2, LewisY, CD24, PDGFR-β, SSEA-4, CD20, folate receptor alpha, ERBB2 (Her2/neu), MUC1, EGFR, NCAM, Prostase, PAP, ELF2M, ephrin B2, IGF-I receptor, CAIX, LMP2, gp100, bcr-abl, tyrosinase, EphA2, fucosyl GM1, sLe, GM3, TGS5, HMW-MAA, o-acetyl-GD2, folate receptor β, TEM1/CD248, TEM7R, CLDN6, GPRC5D, CXORF61, CD97, CD179a, ALK, polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, MAGE-A1, legumain, HPV E6, E7, MAGE A1, ETV6-AML, sperm protein 17, XAGE1, Tie 2, MAD-CT-1, MAD-CT-2, Fos-associated antigen 1, p53, p53 mutant, prostein, survivin and telomerase, PCTA-1/Galectin 8, MelanA/MART1, Ras mutant, hTERT, sarcoma translocation breakpoint, ML-IAP, ERG (TMPRSS2ETS fusion gene), NA17, PAX3, androgen receptor, cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxylesterase, mut hsp70-2, CD79a, CD79b, CD72, LAIR1, FCAR, LILRA2, CD300LF, CLEC12A, BST2, EMR2, LY75, GPC3, FCRL5, IGLL1, DLL3 or a combination thereof. Preferably, the tumor antigen recognition region B1 targets tumor antigen CAIX and/or HER2.

In another preferred embodiment, the tumor antigen recognition region B1 is a VHH antibody (DNA SEQ ID NO.: SEQ 17, AA SEQ ID NO.: SEQ 18) targeting CAIX.

In another preferred embodiment, the tumor antigen recognition region B1 is a single-chain antibody derived from Trastuzumab (DNA SEQ ID NO.: SEQ 65, AA SEQ ID NO.: SEQ 66) targeting HER2.

B2 is a CD3 antigen recognition region, optionally, is a single domain antibody sequence (VHH), and/or an antibody Fab, and/or a single-chain antibody variable region sequence (scFv) that targets CD3. In a preferred embodiment, the CD3 antigen-binding antibody fragment could derived from CD3 Ab clones of L2K, UCHT, OKT3, F6A, SP34 etc.

Optionally, the position of B1 and B2 may be reversed.

T2 is absent or a tag element, optionally comprising a tag protein, a fluorescein labeled protein or an enzyme labeled protein. Preferably, tag protein comprises a FLAG protein (DNA SEQ ID NO.: SEQ 13, AA SEQ ID NO.: SEQ 14), and His protein (DNA SEQ ID NO.: SEQ 35, AA SEQ ID NO.: SEQ 36).

each "—" is independently a linker peptide or peptide bond.

CD3e Protein

"CD3e protein" and "CD3e" stated herein both refer to human CD3e protein.

"Extracellular region of CD3e protein" stated herein refers to amino acids 1-104 of the CD3e protein sequence, as illustrated by SEQ ID NO. NO.: 4.

The protein sequence comprises an amino acid sequence having a homology with the amino acid sequence of not less than 60%, for example, at least 65%, 70%, 75%, 80%, 85%, 90%, 91%, 92%, 93%, 94%, 95%, 96%, 97%, 98%, 99% or 100%.

Chimeric CD3e Fusion Protein

"Chimeric CD3e fusion protein", "CD3e fusion protein", and "chimeric CD3e protein" stated herein refer to a fusion protein expressed in T cells having a structure shown in the following formula I:

L-EC-H-TM-C-CD3ζ (I)

In the formula, each "—" is independently a linker peptide or peptide bond;

L is an optional signal peptide sequence;

EC is a polypeptide binding domain from or derived from a CD3e protein, that is recognizable by an anti-CD3 antibody and binds to the anti-CD3 antibody;

the polypeptide binding domain is also referred to as a recognition binding domain of the anti-CD3 antibody;

the polypeptide binding domain is also referred to as a subunit of recognition binding domain of the anti-CD3 antibody;

H is an optional linker or hinge region;

TM is a transmembrane domain;

C is absent or a costimulatory signal molecule;

CD3ζ is absent or a cytoplasmic signaling sequence derived from CD3ζ.

In another preferred embodiment, the polypeptide binding domain is a CD3e extracellular region as illustrated by SEQ ID NO. NO.: 4, or a portion thereof recognizable by an anti-CD3 antibody.

In another preferred embodiment, the anti-CD3 antibody is selected from the following group: an scFV (single-chain antibody), a single domain antibody sequence (also known as a nanobody), a diabody, an antibody Fab or a variant thereof, or a combination thereof.

In another preferred embodiment, the polypeptide binding domain specifically recognizes and binds to an anti-CD3 antibody, which may be present as a segment of a bispecific antibody.

In another preferred embodiment, the hinge region is CD8 Hinge, and the amino acid sequence thereof is SEQ ID NO. NO.: 3.

In another preferred embodiment, the transmembrane region is CD8 TM, and the amino acid sequence thereof is SEQ ID NO. NO.: 8.

Chimeric CD3 and anti-CD3 Based Bispecific T Cell Activator Engineered T Cells, CAB-T "Chimeric CD3 and anti-CD3 based Bispecific T cell activator engineered T cells", "CAB-T cells", "CAB-T technology", "CAB structure", "CAB-T", "-CAB-T" and "-CAB" stated herein refer to T cells engineered to co-express both chimeric CD3 fusion protein and anti-CD3 based bispecific T cell activator. Preferably, the engineered T cells comprises a construct with the following structure: (i) a chimeric CD3e in the CAB structure comprising at least the following four components: a CD3e extracellular region, a CD8 hinge region and transmembrane region, 4-1BB intracellular region and a CD3 intracellular region; (ii) an anti-CD3 based bispecific T cell activator (BiTA) structure comprises at least the following two moieties: receptor or ligand binding domains, an antibody fragment, including single domain antibody sequence (VHH), an antibody Fab fragment, a single-chain antibody variable region sequence (scFv), or a T-cell receptor (TCR) sequence that recognizes and binds a tumor antigen, and a variable region sequence that recognizes CD3 antigen in TCR complexes.

As noted above, the amino acid sequence of the CD3e extracellular region is shown in SEQ ID NO. NO.: 4, the amino acid sequence of the 4-1BB is shown in SEQ ID NO. NO.: 10, and the amino acid sequence of the CD3ζ is shown in SEQ ID NO. NO.: 12.

Other preferred synthetic gene sequences are shown in Table 1 below:

TABLE 1

Synthetic gene names and nucleotide and amino acid sequences thereof

| Synthetic Gene Name | DNA SEQ ID NO. | AA SEQ ID NO. |
|---|---|---|
| GM-CSFRsp (signal peptide) | SEQ 1 | SEQ 2 |
| CD3e ECD (extracellular region) | SEQ 3 | SEQ 4 |
| CD8 Hinge (hinge region) | SEQ 5 | SEQ 6 |
| CD8 TM (transmembrane region) | SEQ 7 | SEQ 8 |
| 4-1BB costimulatory domain | SEQ 9 | SEQ 10 |
| CD3ζ (TCR activation domain) | SEQ 11 | SEQ 12 |
| FLAG (tag sequence) | SEQ 13 | SEQ 14 |
| CD3e-BBζ | SEQ 15 | SEQ 16 |
| CAIX VHH | SEQ 17 | SEQ 18 |
| L2K scFv | SEQ 19 | SEQ 20 |
| $1^{st}$-CAIX-BiTA | SEQ 21 | SEQ 22 |
| T2A | SEQ 23 | SEQ 24 |
| $1^{st}$-CAIX-CAB | SEQ 25 | SEQ 26 |
| Linker | SEQ 27 | SEQ 28 |
| CD3e full length | SEQ 29 | SEQ 30 |
| CAIX-TRuC | SEQ 31 | SEQ 32 |
| Truncated ERBB2 (tERBB2) | SEQ 33 | SEQ 34 |
| 6 × His | SEQ 35 | SEQ 36 |
| CAIX-BiTA | SEQ 37 | SEQ 38 |
| CAIX-CAB | SEQ 39 | SEQ 40 |
| CAIX-ζ | SEQ 41 | SEQ 42 |
| CD8L (CD8 signal peptide) | SEQ 43 | SEQ 44 |
| CAIX-BBζ | SEQ 45 | SEQ 46 |
| CAIX-28ζ | SEQ 47 | SEQ 48 |
| HER2-CAB | SEQ 49 | SEQ 50 |

TABLE 1-continued

Synthetic gene names and nucleotide and amino acid sequences thereof

| Synthetic Gene Name | DNA SEQ ID NO. | AA SEQ ID NO. |
|---|---|---|
| HER2-ζ | SEQ 51 | SEQ 52 |
| HER2-BBζ | SEQ 53 | SEQ 54 |
| HER2-28ζ | SEQ 55 | SEQ 56 |
| CD28 Hinge | SEQ 57 | SEQ 58 |
| CD28 TM | SEQ 59 | SEQ 60 |
| CD28 costimulatory domain | SEQ 61 | SEQ 62 |
| HER2-BiTA | SEQ 63 | SEQ 64 |
| Trastuzumab scFv | SEQ 65 | SEQ 66 |
| $HER2\text{-}CAB^{R}$ | SEQ 67 | SEQ 68 |
| Humanized CAIX VHH | SEQ 69 | SEQ 70 |
| hCAIX-BiTA | SEQ 71 | SEQ 72 |
| hCAIX-CAB | SEQ 73 | SEQ 74 |
| hCAIX-BBζ | SEQ 75 | SEQ 76 |

CAIX

CAIX is a transmembrane protein expressed in a variety of solid tumor cells. The primary function of CAIX is to maintain the homeostasis of intracellular pH under hypoxic conditions, which is common in solid tumors. The expression of CAIX in tumor cells is considered to be a marker protein for hypoxia in a tumor environment and poor prognosis in patients. Common types of tumors that express CAIX include cervical cancer, kidney cancer, brain cancer, head and neck cancer, esophageal cancer, intestinal cancer, breast cancer, ovarian cancer, endometrial cancer, bladder cancer, and the like. In normal tissues, CAIX is mainly expressed in epithelial cells in the bile duct and small intestine, as well as gastric epithelial cells, etc., but unlike tumor cells, CAIX expressed in normal tissues is mainly localized in the cytoplasm. Therefore, CAIX is an ideal therapeutic target for targeted therapy including cell therapy.

HER2

HER2 is one of the most studied targets in tumor immunotherapy, and is commonly expressed in tissues such as breast cancer, gastric cancer, colorectal cancer, cervical cancer, endometrial cancer, urothelial cancer, ovarian cancer, and lung cancer. Although trastuzumab, a monoclonal antibody drug targeting HER2, has significantly improved the quality of life and prolonged the lifetime of patients with HER2-positive breast cancer, there are still a large number of patients with HER2-positive tumors that do not respond or develop resistance to the trastuzumab. Therefore, there is still a large market demand for the development of new therapeutic approaches targeting HER2. Currently, there are reports on CAR-T drugs targeting HER2. Among them, Steven A Rosenberg reports serious toxic and side effects in clinical trials of a third generation CAR-T drug targeting HER2, and such drug causes respiratory distress and severe immune cell infiltration in lung and thus causes the patient to die. Therefore, during the development of drugs targeting HER2 cells, it must be designed to highlight the safety of the drug.

Composition

The present disclosure provides a composition or a formulation comprising T cells engineered to co-express both chimeric CD3 fusion protein and anti-CD3 based bispecific T cell activator (i.e. the CAB-T cells), together with a pharmaceutically acceptable carrier, diluent or excipient. In one embodiment, the composition is a liquid formulation. Preferably, the composition is an injection. Preferably, the concentration of the CAB-T cells in the composition is $1\times10^{3}$-$1\times10^{8}$ cells/ml, more preferably $1\times10^{4}$-$1\times10^{7}$ cells/ml.

In one embodiment, the composition may include a buffer such as neutral buffered saline, sulfate buffered saline, and the like; a carbohydrate such as glucose, mannose, sucrose or dextran, and mannitol; a protein; a polypeptide or an amino acid such as glycine; an antioxidant; a chelating agent such as EDTA or glutathione; an adjuvant (for example, aluminum hydroxide); and a preservative. The composition of the present disclosure is preferably formulated for intravenous administration.

Therapeutic Application

The present disclosure encompasses the therapeutic application of the T cells engineered to co-express both chimeric CD3 fusion protein and anti-CD3 based bispecific T cell activator (i.e. the CAB-T cells). T cells transduced with vectors comprising the nucleic acid construct of the present disclosure can target tumor cell markers, while autocrine or paracrine BiTA (secreted by the engineered T cells) can synergistically activate T cells and cause T cell immune responses, thereby significantly increasing their killing efficiency against tumor cells.

Accordingly, the present disclosure also provides a method for stimulating a T cell-mediated immune response of a target cell population or tissue in a mammal, comprising the step of administering the CAB-T cells.

Cancers that can be treated include tumor that has not been vascularized or has not been substantially vascularized, as well as vascularized tumors. Cancers can include non-solid tumors (for example, hematological tumor such as leukemias and lymphoma) or solid tumors. Types of cancer that can be treated with the nucleic acid construct and engineered T cells of the present disclosure include, but are not limited to, carcinoma, blastoma, and sarcoma, and certain leukemia or lymphoid malignancy, benign and malignant tumor, and malignancy, such as sarcoma, carcinoma, and melanoma. Adult tumor/cancer and pediatric tumor/cancer are also included.

Hematological cancer is a cancer of the blood or bone marrow. Examples of hematological (or hematogenous) cancer include leukemia, including acute leukemia (such as acute lymphocytic leukemia, acute myelocytic leukemia, acute myelogenous leukemia, and myeloblastic leukemia, promyelocytic leukemia, granulocyte-monocyte leukemia, monocyte leukemia and erythroleukemia), chronic leukemia (such as chronic myelocytic (granulocytic) leukemia, chronic myelogenous leukemia and chronic lymphocytic leukemia), polycythemia vera, lymphoma, Hodgkin's disease, non-Hodgkin's lymphoma (painless and high-grade forms), multiple myeloma, Waldenstrom's macroglobulinemia, heavy chain disease, myelodysplastic syndrome, hairy cell leukemia, and myelodysplasia.

A solid tumor is an abnormal mass of tissue that usually does not contain a cyst or fluid area. Solid tumors can be benign or malignant. Different types of solid tumors are named after the cell types that form them (such as sarcoma, carcinoma, and lymphoma). Examples of solid tumor such as sarcoma and carcinoma include fibrosarcoma, mucinous sarcoma, liposarcoma, mesothelioma, lymphoid malignancy, pancreatic cancer, and ovarian cancer.

The CAB-modified T cells of the present disclosure can also be used as a vaccine for ex vivo immunization and/or in vivo therapy in a mammal. Preferably, the mammal is human.

For ex vivo immunization, at least one of the following occurs in vitro prior to administration of the cells into the mammal: i) amplifying the cells, ii) introducing a CAB-encoding nucleic acid into the cells, and/or iii) cryopreserving the cells.

Ex vivo procedures are well known in the art and are discussed in more details below. Briefly, cells are isolated from a mammal, preferably human, and genetically modified (i.e., transduced or transfected in vitro) with a vector that expresses the CABs disclosed herein. CAB-modified cells can be administered to a mammalian recipient to provide a therapeutic benefit. The mammalian recipient can be human, and the CAB-modified cells can be autologous relative to the recipient. Alternatively, the cells may be allogeneic, syngeneic or xenogeneic relative to the recipient.

In addition to the use of cell-based vaccines for ex vivo immunization, the present disclosure also provides a composition and a method for in vivo immunization to elicit an immune response against antigens in a patient.

The present disclosure provides a method for treating a tumor, comprising administering a therapeutically effective amount of a CAB-modified T cell of the present disclosure to a subject.

The CAB-modified T cells of the present disclosure can be administered alone or in combination with a diluent and/or with other components such as IL-2, IL-17 or other cytokines or cell populations in the form of a pharmaceutical composition. Briefly, the pharmaceutical composition of the present disclosure may comprise a population of target cells as described herein in combination with one or more pharmaceutically or physiologically acceptable carriers, diluents or excipients. Such compositions may include a buffer such as neutral buffered saline, sulfate buffered saline, and the like; a carbohydrate such as glucose, mannose, sucrose or dextran, and mannitol; a protein; a polypeptide or an amino acid such as glycine; an antioxidant; a chelating agent such as EDTA or glutathione; an adjuvant (for example, aluminum hydroxide); and a preservative. The composition of the present disclosure is preferably formulated for intravenous administration.

The pharmaceutical composition of the present disclosure can be administered in a manner suitable for the disease to be treated (or prevented). The amount and frequency of administration will be determined by factors such as the condition of a patient, and the type and severity of the patient's disease—although appropriate dosages may be determined by clinical trials.

When referring to "immunologically effective amount", "anti-tumor effective amount", "tumor-suppressing effective amount" or "therapeutic amount", the precise amount of the composition of the present disclosure to be administered can be determined by a physician, taking into account the age, weight, tumor size, and degree of infection or metastasis of the patient (subject), and individual differences in the condition. It is generally indicated that a pharmaceutical composition comprising a T cell as described herein can be administered at a dose of $10^4$ to $10^9$ cells/kg body weight, preferably a dose of $10^5$ to $10^6$ cells/kg body weight, including all integer values within those ranges. T cell composition can also be administered for multiple times at these doses. Cells can be administered by using injection techniques well known in immunotherapy (see, for example, Rosenberg et al, New Eng. J. of Med. 319: 1676, 1988). Optimal dosages and treatment regimens for a particular patient can be readily determined by a person skilled in the medical field by monitoring the patient's signs of disease and thus regulating the treatment.

The composition can be administrated to a subject in any convenient manner, including by nebulization, injection, oral administration, infusion, implantation or transplantation. The composition described herein can be administered to a patient subcutaneously, intradermally, intratumorally, intranodally, intraspinally, intramuscularly, by intravenous (i.v.) injection or intraperitoneally. In one embodiment, a T cell composition of the present disclosure is administered to a patient by intradermal or subcutaneous injection. In another embodiment, the T cell composition of the present disclosure is preferably administered by i.v. injection. The T cell composition can be injected directly into tumor, a lymph node or an infected site.

In certain embodiments of the present disclosure, cells activated and expanded using the methods described herein, or other methods known in the art to expand T cells to therapeutic levels are administered to a patient in conjunction with (e.g., prior to, simultaneously or following) any number of related therapeutic modalities, including but not limited to treatment with agents such as antiviral therapy, cidofovir and interleukin-2, cytarabine (also known as ARA-C) or natalizumab treatment for patients with MS or efalizumab treatment for patients with psoriasis or other treatments for patients with PML. In a further embodiment, the T cells of the present disclosure can be used in combination with chemotherapy, radiation, immunosuppressive agents such as cyclosporin, azathioprine, methotrexate, mycophenloate and FK506, antibodies or other immunotherapeutic agents. In a further embodiment, the cell composition of the present disclosure is administered to a patient in conjunction with (e.g., prior to, simultaneously or following) bone marrow transplantation, a chemotherapeutic agent such as fludarabine, external beam radiation therapy (XRT), or cyclophosphamide. For example, in one embodiment, the subject may undergo a standard treatment by high dose chemotherapy, followed by peripheral blood stem cell transplantation. In some embodiments, the subject receives an injection of the expanded immune cells of the present disclosure after transplantation. In one additional embodiment, the expanded cells are administered prior to or after surgery.

The dosage of the above treatment administered to the patient will vary with the precise nature of the condition being treated and the recipient being treated. The dosage ratios administered to human can be carried out according to practices accepted in the art. Typically, for each treatment or each course of treatment, $1\times10^6$ to $1\times10^{10}$ modified T cells of the present disclosure can be administered to a patient by, for example, intravenous reinfusion.

The Technical Solution of the Present Disclosure Has the Following Beneficial Effects:

1. The present disclosure provides an immunotherapeutic regimen for inhibiting tumors, particularly solid tumors, namely combining T cells expressing a chimeric CD3 fusion protein with BiTA. The chimeric CD3 fusion protein and BiTA bind to each other and function to activate T cells and target tumor cells.
2. The present disclosure also provides a CAB technology for CAB-T cells to target tumor tissues by chimeric expression of CD3 and BiTA in T cells, and BiTA secreted by CAB-T cells can simultaneously achieve the activation of the CAB-T cells and the activation of the endogenous TCR complexes of the non-engineered T cells in tumor tissues, exert the anti-tumor effect of CAB-T itself and mobilize the anti-tumor effect of the non-engineered T cells, thereby ensuring the effectiveness of CAB-T clinical application.
3. Since the activation of chimeric CD3 is dependent on BiTA secreted by CAB-T, a small amount of BiTA released by CAB-T in tumor tissues can stimulate CAB-T to release more BiTA in the local tumor microenvironment, which advantageously ensures the safety of CAB-T clinical application.
4. CAB-T can achieve better activation in solid tumor tissues, achieve the maximum anti-tumor effect at a tumor site, achieve safety and effectiveness similar to those of local administration of tumors, and has great advantages and potential in the clinical treatment of solid tumors compared with second generation CAR-T.

The present disclosure is further illustrated below with specific examples. It is to be understood that these examples are for illustrative purposes only and not intended to limit the scope of the present disclosure. Experimental methods in which specific conditions are not indicated in the following examples are generally carried out according to the conventional conditions described by, for example, Sambrook et al., Molecular Cloning: A Laboratory Manual (New York: Cold Spring Harbor Laboratory Press, 1989), or according to the conditions recommended by a manufacturer. Percentages and parts are by weight unless otherwise stated.

Example 1

Design of CAB and Its Control Structures 1.1 Structural Design of CD3e-BBζ, $1^{st}$-CAIX-BiTA, $1^{st}$-CAIX-CAB and CAIX-TRuC in a Control Group To validate the anti-tumor activity of CAB-T, we first designed a first group of four structures using a nanobody (VHH) targeting CAIX in a group of experiments: CD3e-BBζ (DNA SEQ ID NO.: SEQ 15, AA SEQ ID NO.: SEQ 16), CAIX-BiTA (DNA SEQ ID NO.: SEQ 21, AA SEQ ID NO.: SEQ 22), CAIX-CAB (DNA SEQ ID NO.: SEQ 25, AA SEQ ID NO.: SEQ 26) and CAIX-TRuC (DNA SEQ ID NO.: SEQ 31, AA SEQ ID NO.: SEQ 32). In order to distinguish from the second group of CAIX-CAB structures described later, we named CAIX-BiTA and CAIX-CAB of this group as $1^{st}$-CAIX-BiTA and $1^{st}$-CAIX-CAB, respectively. Among them, $1^{st}$-CAIX-BiTA is a BiTA without tags, $1^{st}$-CAIX-CAB comprises CD3e-BBζ and a CAB structure where BiTA is not labeled, and CAIX-TRuC is a control structure using a platform technology of $TCR^2$ Therapeutics. The specific structure the above constructs are shown in FIG. 1.

Figure 2:
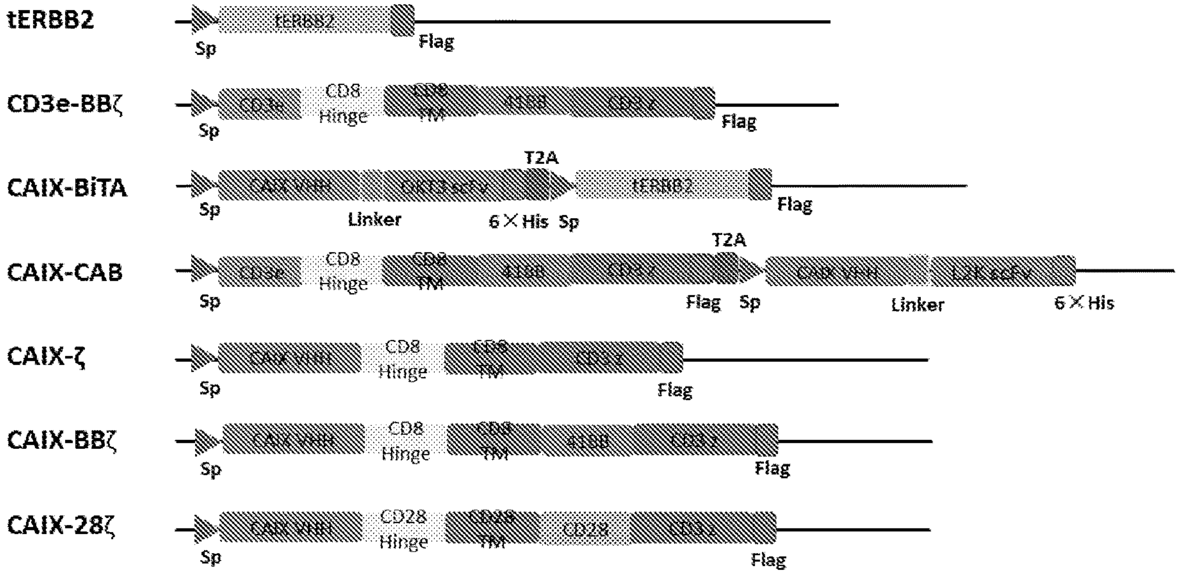
FIG. 2 shows the structures of the CAB-T according to a second group of experiments and its control group.

1.2 Structural Design of tERBB2, CD3e-BBζ, CAIX-BiTA, CAIX-CAB, CAIX-ζ, CAIX-BBζ and CAIX-28ζ in an Experimental Group of Nanobody (VHH) Targeting CAIX In another group of experiments, we designed a second group of structures using VHH targeting CAIX, including: truncated ERBB2 (tERBB2 used as a negative control, including the fourth extracellular domain of ERBB2, transmembrane region, and FLAG tag) (DNA SEQ ID NO.: SEQ 33, AA SEQ ID NO.: SEQ 34), CD3e-BBζ (DNA SEQ ID NO.: SEQ 15, AA SEQ ID NO.: SEQ 16), CAIX-BiTA (DNA SEQ ID NO.: SEQ 37, AA SEQ ID NO.: SEQ 38), CAIX-CAB (DNA SEQ ID NO.: SEQ 39, AA SEQ ID NO.: SEQ 40), CALX-ζ (a first generation CAR structure targeting CAIX) (DNA SEQ ID NO.: SEQ 41, AA SEQ ID NO.: SEQ 42), CAIX-BBζ (a second generation CAR structure containing the 4-1BB costimulatory domain) (DNA SEQ ID NO.: SEQ 45, AA SEQ ID NO.: SEQ 46) and CAIX-28ζ (a second generation CAR structure containing the CD28 costimulatory domain) (DNA SEQ ID NO.: SEQ 47, AA SEQ ID NO.: SEQ 48), 7 structures in total. In this group of structures, all the structures carry a FLAG tag, and all of the secretory BiTA antibodies have a His tag. The inclusion of His tag facilitates the subsequent detection of BiTA secretion levels. The details of these constructs are shown in FIG. 2.

1.3 Structural Design of tERBB2, CD3e-BBζ, HER2-BiTA, HER2-CAB, HER2-ζ, HER2-BBζ and HER2-28ζ in the Experimental Group of Single-Chain Antibody Targeting HER2

Figure 3:
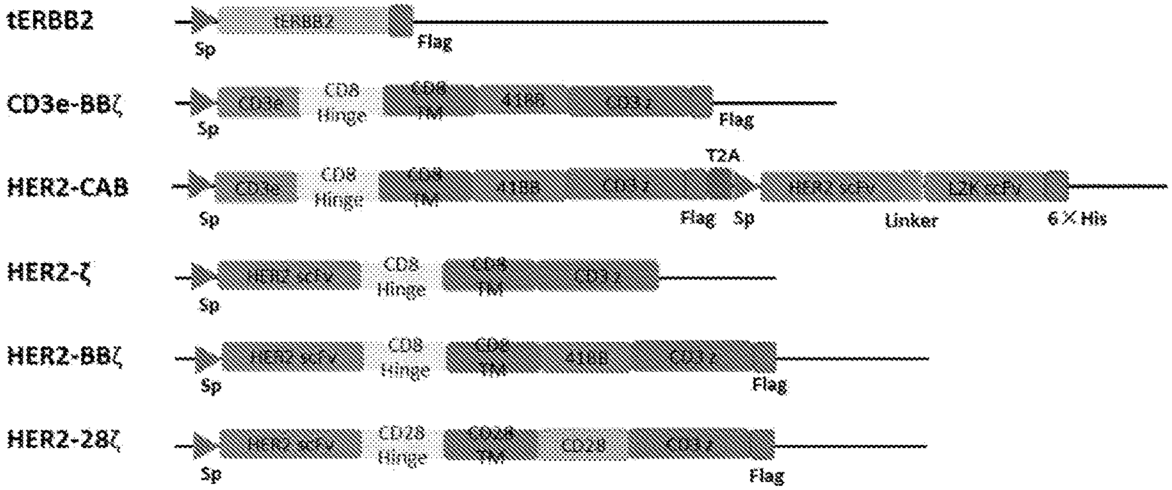
FIG. 3 shows the structures of the CAB-T according to a third group of experiments and its control group.

In the third groups of experiments, we tested the anti-tumor activity of a CAB platform using a single-chain antibody (scFv) that targets HER2. The single-chain antibody variable region sequence is derived from an antibody drug Herceptin (trastuzumab). In this example, we designed a third group of structures including: truncated ERBB2, CD3e-BBζ, HER2-CAB (DNA SEQ ID NO.: SEQ 49, AA SEQ ID NO.: SEQ 50), HER2-ζ (DNA SEQ ID NO.: SEQ 51, AA SEQ ID NO.: SEQ 52), HER2-BBζ (DNA SEQ ID NO.: SEQ 53, AA SEQ ID NO.: SEQ 54) and HER2-28ζ, second generation CAR structure (DNA SEQ ID NO.: SEQ 55, AA SEQ ID NO.: SEQ 56), 7 structures in total. In this group of structures, all structures except HER2-ζ carry the FLAG tag, and all secretory BiTA antibodies also carry the His tag. The details are shown in FIG. 3.

Example 2

Lentivirus Packaging of CAB and Its Control Structures

In the present disclosure, we prepared CAB-T cells using lentivirus as a vector. First, we prepared a lentiviral vector carrying a gene encoding CAB and its control structures. A specific procedure for packing lentivirus is as follows.

1) $1\times10^7$ HEK 293T cells were seeded in a 10 cm culture plate, 10 mL of DMEM (Hyclone, SH30243.01) medium containing 10% FBS (Gibco, 10099-141C) was added, and the cells were mixed fully and incubated at 37° C. overnight.
2) On the second day, the medium was replaced with a serum-free DMEM when the cell confluence of HEK 293T (ATCC, CRL-3216) reached about 90%.
3) A plasmid complex was prepared, in which the amounts of various plasmids were 8 μg plasmid DNA, 4 μg psPAX2 and 2 μg pMD2g, respectively, and dissolved in 1 mL opti-MEM (Gibco, 31985-070), and 42 μL PEI (Polysciences, 24765-2) was added; shaking was performed under vortex for 20 s. After standing at room temperature for 15 min, the mixture was gently added to the HEK293T medium along the side, and culture was kept at 37° C.
4) Following the culture of cells for 4 h, the medium was removed, and washed once with PBS (Hyclone, SH30256.01), and 2% FBS pre-warmed fresh DMEM medium was added again.
5) After transfection for 48 h and 72 h, supernatants were collected respectively, and centrifuged at 2000 g for 5 min, and the precipitate was discarded. The supernatant was filtered with a 0.25 μm filter (Sartorius, 16541-K) and then PEG 8000 (Sigma, 89510-1KG-F) with a final concentration of 5% and NaCl (Sigma, S5150-1L) with a final concentration of 0.15 M were added, vigorously mixed and allowed to stand overnight at 4° C.
6) The virus supernatant was centrifuged at 2000 g, 4° C. for 20 min, the supernatant was removed, and virus pellets were dissolved in 50-100 μL of PBS and frozen at −80° C.

Example 3

Preparation of Engineered T Cells With CAB and Its Control Structures

Following the completion of the preparation of the lentiviral vector carrying the CAB structure, the lentiviral vector can be used to infect immune cells to complete the preparation of CAB-T cells. A specific procedure for preparing CAB-T cells is as follows.

1) Commercialized PBMC (Saily Bio, SLB-HP050B) cells were cultured with X-VIVO 15 (LONZA, 04-418Q) containing 5% human blood albumin (GRIFOLS, 20% human blood albumin) at an initial cell density of $1\times10^6$/mL.
2) Anti-CD3/CD28 beads (Miltenyi biotec, 130-091-441) were added in a ratio of cells: Beads=3:1, and 1000 IU/mL of IL-2 (Si Huan Sheng Wu, SFDA approval number: S10970016) was added to activate T cell expansion.
3) After cell activation for 48 h, T cells were infected by adding appropriate amount of virus and 12 μg/mL protamine (Sigma, P4005).
4) After lentivirus infection for 24 h, the cell suspension was aspirated, and a completely fresh X-VIVO 15 medium was added at a concentration of $1\times10^6$ cells/mL.
5) The density of cells was observed every day, T cell culture solution containing 1000 IU/ml of IL-2 was added in good time to maintain the density of T cells at about $1\times10^6$ cells/mL, and expansion was continued for 5-10 days to complete the preparation of CAR-T cells.

Example 4

Positive Frequency Assay of CAB-T Cells

Upon the completion of the preparation of CAB-T and its control group cells, the infection efficiency was determined for subsequent activity analysis. Specifically, a method for detecting the CAB-T positive frequency using a FLAG antibody is as follows.

1) $3\text{-}5\times10^5$ cells were taken, 200 μL FACS buffer (PBS containing 1% FBS) was added into each flow cytometry tube, and the mixture was centrifuged at 300 g for 5 min; biotin-CAIX (sino biological, 10107-H02H) at a final concentration of 100 nM was added to a CAIX-Truc sample, and the mixture was incubated at 4° C. for 20 min; biotin-HER-2 (ACRO, HE2-H82E2) at a final concentration of 100 nM was added to an Her2-Truc sample, and the mixture was incubated at 4° C. for 20 min; the supernatant was discarded, 200 μL Fixation/Permeabilization solution (BD bioscience, 554715) was added, and the mixture was incubated at 4° C. for 20 min.
2) The mixture was centrifuged at 300 g for 5 min; the supernatant centrifuged was removed, 200 μL of 1×Perm/Wash buffer (BD bioscience, 554715) was added, and the mixture was resuspended, centrifuged at 400 g for 5 min, and washed twice;
3) the supernatant centrifuged was removed, 100 μL of anti-Flag antibody diluted with 1:1000 FACS buffer was added into each sample, and the cells were mixed well and incubated at 4° C. for 30 min.
4) After incubation, 1 mL of FACS buffer was added to each flow cytometry tube, and the mixture was centrifuged at 400 g for 5 min.

5) The supernatant centrifuged was removed, 1 mL FACS buffer was added, and the mixture was resuspended and centrifuged at 400 g for 5 min.
6) The supernatant centrifuged was removed, 100 μL of SA-PE (Invitrogen, S866) diluted with 1:250 FACS buffer was added to each sample, the cells were mixed well and incubated at 4° C. for 30 min in the dark; after incubation, 1 mL of FACS buffer was added to each flow cytometry tube, and the mixture was centrifuged at 300 g for 5 min; the supernatant centrifuged was removed, and washing was repeated twice.
7) The sample was placed on a flow cytometer for detection.

Figure 4:
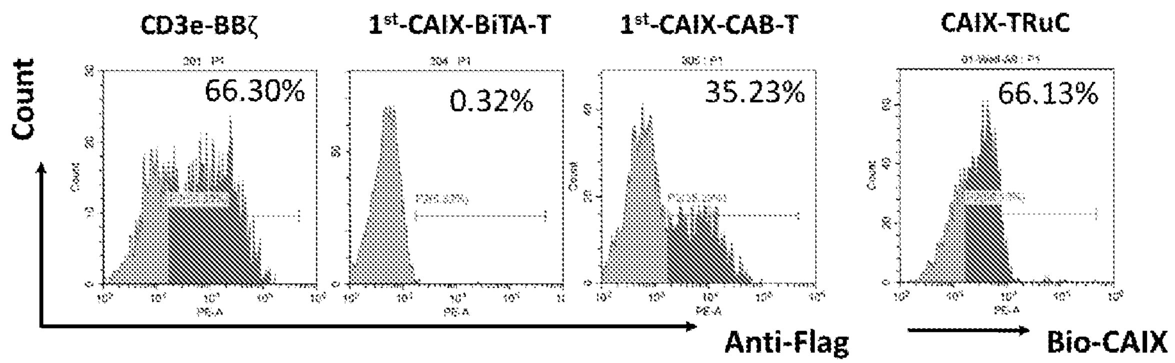
FIG. 4 shows the transduction frequency results of a T cell engineered by the first group of structures.

Results:

In the first group of experiments, the FLAG antibody can be used to detect the positive frequencies of T cells engineered by the corresponding structure as the FLAG tag was carried in the CD3e-BBζ structure and the $1^{st}$-CAIX-CAB structure, while biotin-labeled CAIX protein can be used to detect the positive frequencies of T cell transduction for T cells engineered by CAIX-TRuC. However, since the $1^{st}$-CAIX-BiTA structure does not have a suitable tag, the positive frequencies of T cells engineered by this structure cannot be detected. However, it can be judged from the subsequent results that the positive frequency of T cells engineered by $1^{st}$-CAIX-BiTA can meet the requirement of experimental analysis. The results of the detection are shown in FIG. 4.

Figure 5:
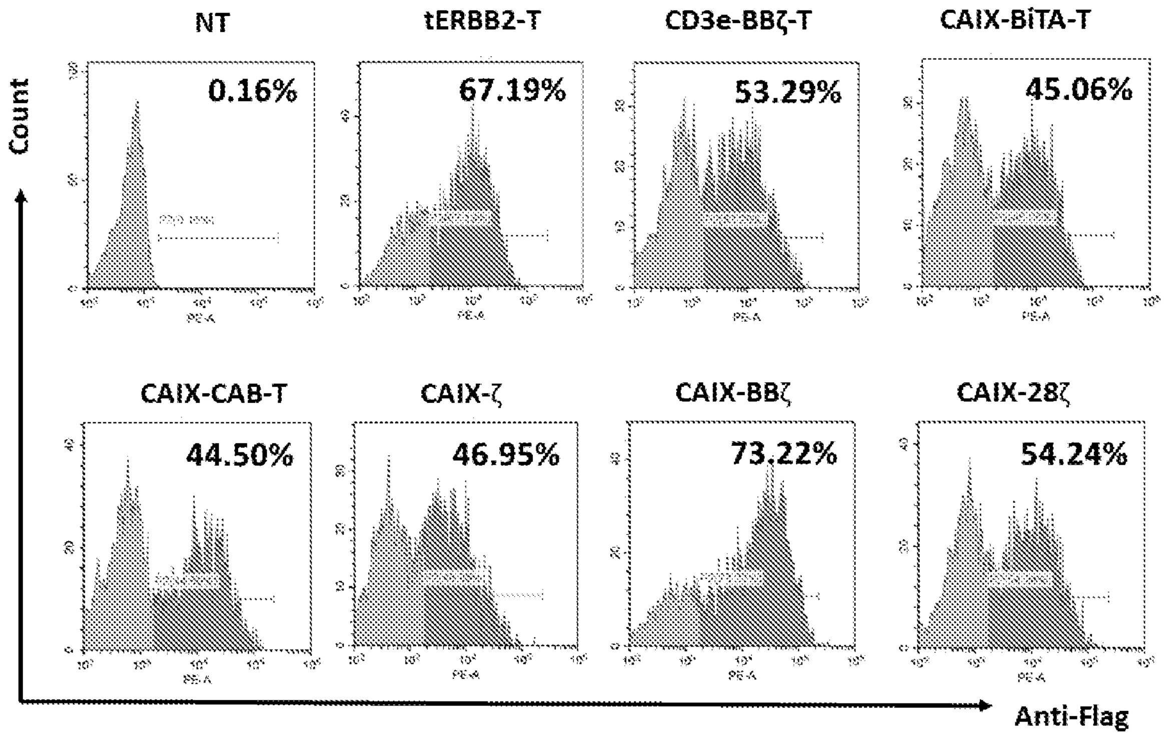
FIG. 5 shows the transduction frequency results of a T cell engineered by the second group of structures.
Figure 6:
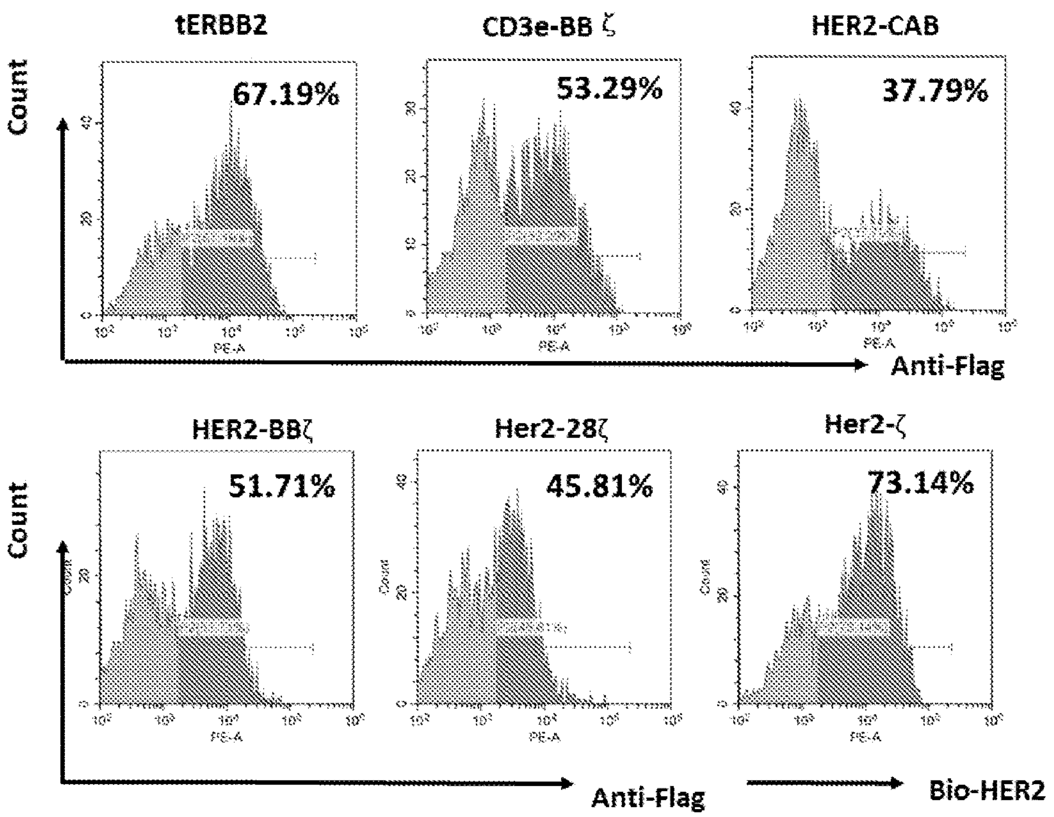
FIG. 6 shows the transduction frequency assay results of a T cell engineered by the third group of structures.

In the second and third groups of experiments, we designed a FLAG tag for each structure, and the positive frequencies of the corresponding engineered T cells can be carried out the labelling and detection of the FLAG antibody (for first generation structure HER2-ζ without a FLAG tag, biotinylated HER2 was used for transduction efficiency detection). NT represents non-transduced T cells and were used as a negative control group. The test results are shown in FIG. 5 and FIG. 6. Differences in infection efficiency between different samples are within acceptable limits.

It can be seen from the above that the positive frequency of transduction for each group of engineered T cells designed by using the structures disclosed in the present disclosure and the prior art meet the requirement of experimental analysis.

Example 5

Antigen Dependent Cytokine Release Assay of CAB-T

When CAB-T cells are co-cultured with tumor cells, CAB-T can recognize and activate target antigens on the surface of tumor cells, thereby releasing a large number of inflammatory cytokines. Based on this, the level of cytokines released by activated CAB-T cells was detected by enzyme-linked immunosorbent assay (ELISA) in the present example.

Detection procedure for ELISA is as follows.

1) $1\times10^5$ effector cells and $1\times10^5$ target cells were seeded at 200 μL/well. A 96-well cell culture plate was co-cultured overnight, and centrifuged at 300 g for 5 min, and 150 μL of the supernatant/well was pipetted into a new 96-well cell culture plate using a multichannel pipette, and cytokine detection was performed using IFN-γ (Invitrogen, 88-7316-88)/IL-2 (Invitrogen, 88-7025-88)/TNF-α (Invitrogen, 88-7346-88) assay kit, respectively.
2) The ELISA plate was coated with Human anti-IFN-γ/IL-2/TNF-α antibodies one day in advance. Human anti-IFN-γ/IL-2/TNF-α antibodies were diluted with PBS (1:250), 100 μL of the antibody was added to each well, and the ELISA plate was sealed with a microplate sealer at 4° C. overnight.
3) Plate washing: liquid in the plate was quickly removed, Wash Buffer was added with a multichannel pipette at 200 μL/well, and the plate washing was repeated for five times.
4) 200 μL of 1×ELISA/ELISASPOT diluent was added to each well, covered with a microplate sealer, and blocked at room temperature for 60 min.
5) Plate washing: liquid in the plate was quickly removed, Wash Buffer was added with a multichannel pipette at 200 μL/well, and the plate washing was repeated for five times.
6) Human IFN-γ ELISA Standard was prepared, and 8 gradients (in pg/mL) were set: 1000, 500, 250, 125, 62.5, 31.25, 15.625, and 7.8125.
7) The standard and the sample were added to the ELISA plate at 100 μL/well, and the sample and the standard were both diluted to the desired concentration with 1×1×ELISA/ELISASPOT diluent, covered with a microplate sealer and incubated for 2 h at room temperature.
8) Plate washing: liquid in the plate was quickly removed, Wash Buffer was added with a multichannel pipette at 200 μL/well, and the plate washing was repeated for four times.
9) The Human IFN-γ/IL-2/TNF-α detection antibody was diluted with PBS (1:250), 100 μL of the antibody was added to each well, and the ELISA plate was sealed with a microplate sealer and incubated for 1 h at room temperature.
10) HRP-conjugated Streptavidin was prepared by diluting with PBS (1:250), and added at 100 μL/well to the ELISA plate, which was covered with a microplate sealer and incubated for 30 min at room temperature.
11) Plate washing: liquid in the plate was quickly removed, Wash Buffer was added with a multichannel pipette at 200 μL/well, and the plate washing was repeated for five times.
12) TMB Substrate was warmed to room temperature 30 minutes in advance, and added at 100 μL/well to the ELISA plate. After reaction for 5-10 min at room temperature, 50 μL/well of Stop solution was added.
13) The absorbance was read in a microplate reader at the detection wavelength of OD=450 nm.
14) A standard curve was calculated according to the concentration and OD value of the standard, and the concentration of the sample to be tested was calculated according to the standard curve. The plot was made by GraphPad Prism mapping software.

Figure 7:
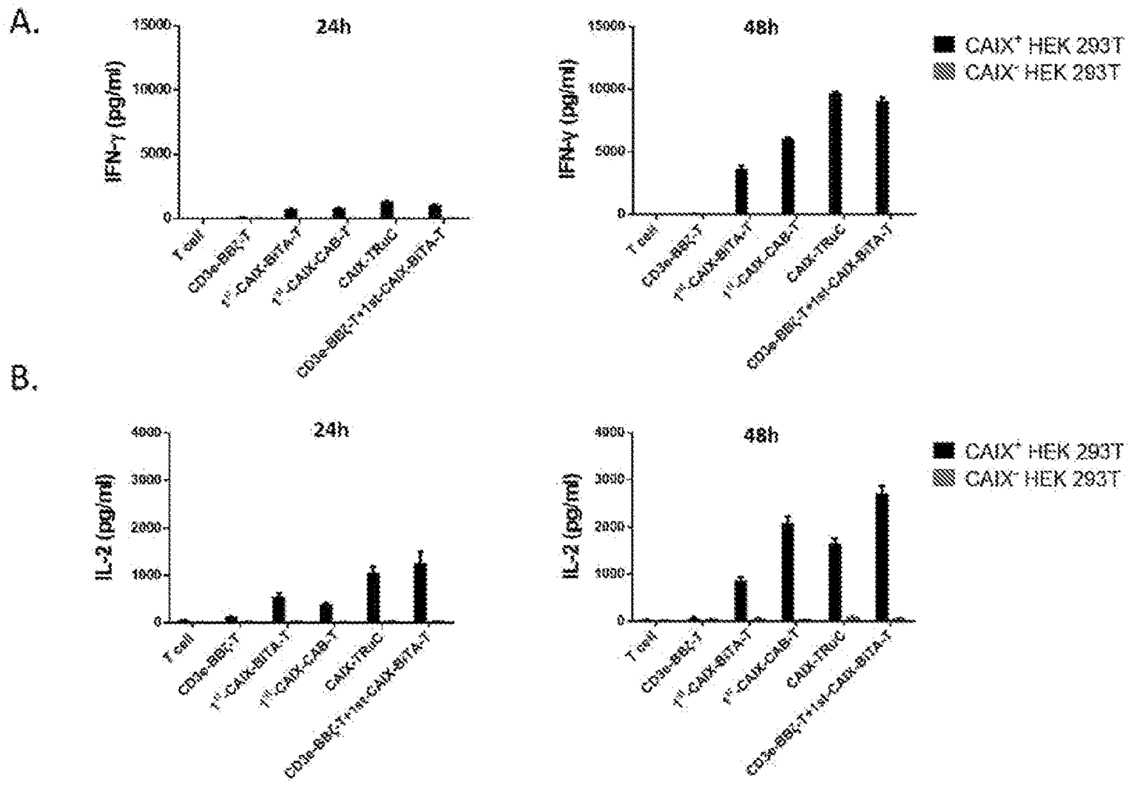
FIG. 7 shows a CAIX-CAB-T cytokine release assay (of the constructs from the first group of experiments).

Results:

In the first group of experiments, after the CAIX-CAB-T cells or their control group cells were co-cultured with CAIX+ HEK 293T cells or CAIX-HEK293T, respectively, the release levels of inflammatory cytokines IL-2 and IFN-γ in the supernatant were detected. The results were shown in FIG. 7. When CAIX-CAB-T and its control groups were co-cultured with CAIX-HEK 293T cells, respectively, none of the immune cells showed significant cytokine release. When CAIX-CAB-T and its control were co-cultured with CAIX+ HEK 293T cells, T cells engineered by 1st-CAIX-BiTA, 1st-CAIX-CAB and CAIX-TRuc all exhibited co-culture time-dependent cytokine release levels. The cytokines accumulated in co-culture for 48 h were significantly higher than the cytokine levels accumulated in co-culture for 24 h. When non-engineered T cells and T cells engineered by CD3e-BBζ were co-cultured with CAIX+ HEK 293T cells, respectively, no significant release of IL-2 and IFN-γ cytokines was detected. At the same time, it was unexpectedly found that the level of cytokine released by 1st-CAIX-CAB-T cells was significantly higher than that of 1st-CAIX-BiTA-T cells after 48 hours of co-culture; after T cells engineered by CD3e-BBζ and 1st-CAIX-BiTA were mixed in a ratio of 1:1 and then co-cultured with CAIX+ HEK 293T cells, the levels of cytokines released were found to be comparable to those of 1st-CAIX-CAB-T cells. The above results indicated that CAIX-CAB-T cell activation was dependent on CAIX antigen, and the BiTA and CD3e-BBζ synergistically promoted T cell activation; it was also demonstrated that CAB-T cells had comparable in vitro activation ability as compared to control group TRuC-T cells.

Figure 8:
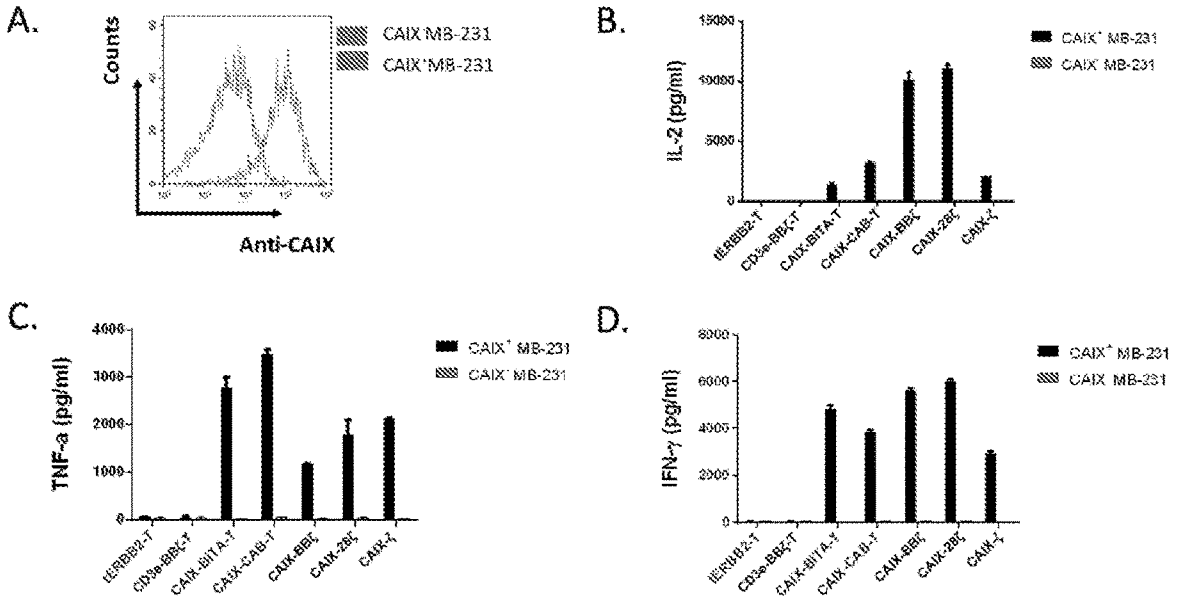
FIG. 8 shows a CAIX-CAB-T cytokine release assay (of the constructs from the second group of experiments).

In the second group of experiments, after CAIX-CAB-T and its control group cells were co-cultured with CAIX+ MB-231 or CAIX-MB-231 cells (CAIX expression levels were shown in FIG. 8. A), respectively, the release levels of the inflammatory cytokines IL-2, IFN-γ, and TNF-α in the supernatant were detected. The results were shown in FIG. 8. When CAIX-CAB-T cells and their controls were co-cultured with CAIX-MB-231 cells, respectively, none of the cells showed significant cytokine release. After CAIX-CAB-T and its control groups were co-cultured with CAIX+ MB-231 cells for 48 h, respectively, the T cells engineered by CAIX-BiTA, CAIX-CAB, CAIX-BBζ, CAIX-28ζ and CAIX-ζ had varying degrees of activation levels. From the data, it can be found that CAIX-CAB-T and CAIX-BiTA, and T cells structurally modified by first and second generation CAR had almost the same release ability in IFN-γ and TNF-α; while in terms of IL-2 release, CAIX-CAB-T was weaker than second generation CAR cells, but slightly higher than CAIX-BiTA and first generation CAR-modified T cells. The results of the second group of experiments indicated the dependence of CAIX-CAB-T cell activation on CAIX antigen and the difference in cytokine release compared to second generation CAR, that is, IFN-γ and TNF-α released by CAIX-BiTA-T and CAIX-CAB-T were substantially equivalent to the release by the second generation CAR, and CAIX-BiTA-T and CAIX-CAB-T were weaker than the second generation CAR in IL-2 release.

Example 6

Antigen Dependent T Cell Activation Marker Upregulation of CAB-T

When CAB-T cells are co-cultured with tumor cells, CAB-T can recognize and activate target antigens on the surface of tumor cells. The expression levels of T cell activation marker proteins including CD137, CD25, CD27 and the like on membrane surface are significantly up-regulated. The cell proliferation ability represented by the expression level of Ki67 is increased, and the killing ability of T cells represented by CD107a is also enhanced. Based on this, the above-described staining method and flow cytometry were used to detect changes in the expression level of the above-mentioned membrane surface proteins in activated CAB-T cells in the present example.

A specific cell staining procedure was as follows:

1) $1\times10^5$ effector cells and $1\times10^5$ target cells were seeded at 200 μL/well. A 96-well cell culture plate was co-cultured overnight and centrifuged at 300 g for 5 min, and each well was added with 200 μL FACS buffer, and centrifuged at 300 g for 5 min.
2) The supernatant centrifuged was removed, and the cells were resuspended by adding 200 μL FACS buffer and centrifuged at 300 g for 5 min.
3) The antibody was diluted with FACS buffer (100 μL/well)

BV421 Mouse Anti-Human CD3 (BD Bioscience, 562426) 1:500 dilution

PE Mouse Anti-Human CD137 (BD Bioscience, 555956) 1:200 dilution

APC Mouse Anti-Human CD27 (BD Bioscience, 561786) 1:200 dilution

PE-cy7 Mouse Anti-Human CD25 (BD Bioscience, 557741) 1:200 dilution

4) The supernatant centrifuged was removed, and 100 μL of the antibody was added to each well, mixed, and incubated at 4° C. for 30 min in the dark.
5) 200 μL FACS buffer was added to each well and centrifuged at 300 g for 5 min, and the supernatant was removed.
6) The supernatant centrifuged was removed and step 2.5 was repeated.
7) The supernatant was discarded, and 200 μL Fixation/Permeabilization solution (BD bioscience, 554715) was added and incubated at 4° C. for 20 min.
8) Centrifugation was performed at 300 g for 5 min. The supernatant centrifuged was removed, 200 μL 1×Perm/Wash buffer (BD bioscience, 554715) was added for resuspending, and centrifugation was performed at 400 g for 5 min.
9) Washing was performed twice and the antibody FITC Mouse Anti-Flag (Biolegend, 637318) was diluted with FACS buffer by 1:1000 dilution.
10) Centrifugation was performed at 400 g for 5 min. the supernatant centrifuged was removed, and washing was performed twice.
11) Flow cytometry detection was performed using FSC/SSC gating to obtain a desired lymphocyte population (PBMCs), CD3 BV421+ and Flag FITC+ cell populations were selected to obtain live CAR-T cells, and then gated by using PBMCs not subjected to virus transduction as standard to obtain the percentage of CAR-T cells CD137 PE+ cells.

Figure 9:
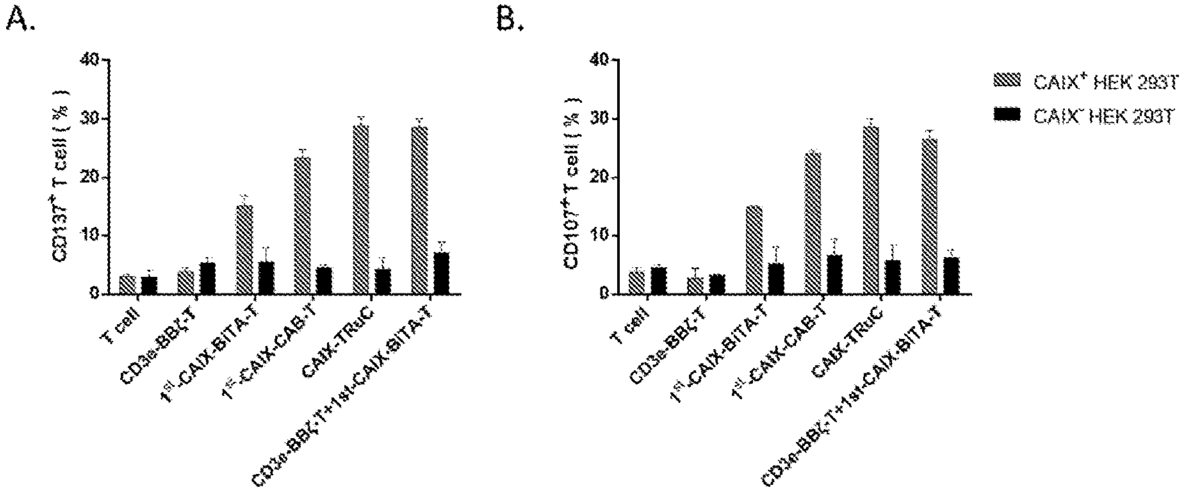
FIG. 9 shows a CAIX-CAB-T cell activation level assay (of the constructs from the first group of experiments).

Results:

In the first group of experiments, after CAIX-CAB-T cells or their control group cells were co-cultured with CAIX+ HEK 293T cells or CAIX-HEK293T, respectively, changes in the expression levels of CD137 and CD107a on the surface of T cell membranes were detected. The results were shown in FIG. 9. When CAIX-CAB-T and its control groups were co-cultured with CAIX-HEK 293T cells, the expression levels of CD137 and CD107a in CAB-T and its control group immune cells were not significantly changed. After CAIX-CAB-T and its control groups were co-cultured with CAIX+ HEK 293T cells for 24 h, respectively, the expression levels of CD137 and CD107a in T cells engineered by 1st-CAIX-BiTA, 1st-CAIX-CAB and CAIX-TRuC were significantly up-regulated, and 1st-CAIX-CAB-T demonstrated a much higher up-regulation level as compared to 1st-CAIX-BiTA. When non-engineered T cells and T cells engineered by CD3e-BBζ were co-cultured with CAIX+ HEK 293T cells, respectively, no significant up-regulation of CD137 and CD107a was detected. After T cells engineered by CD3e-BBζ and 1st-CAIX-BiTA were mixed in a ratio of 1:1 and then co-cultured with CAIX+ HEK 293T cells for 24 h, the expression levels of CD137 and CD107a were found to be significantly higher than those of CD3e-BBζ-T and 1st-CAIX-BiTA-T individually co-cultured with CAIX+ HEK 293T. The above results indicated that CAIX-CAB-T cell activation was dependent on CAIX antigen, and the BiTA and CD3e-BBζ synergistically promoted T cell activation; it was also demonstrated that CAB-T cells had comparable in vitro activation ability to control group TRuC-T cells.

Figure 10:
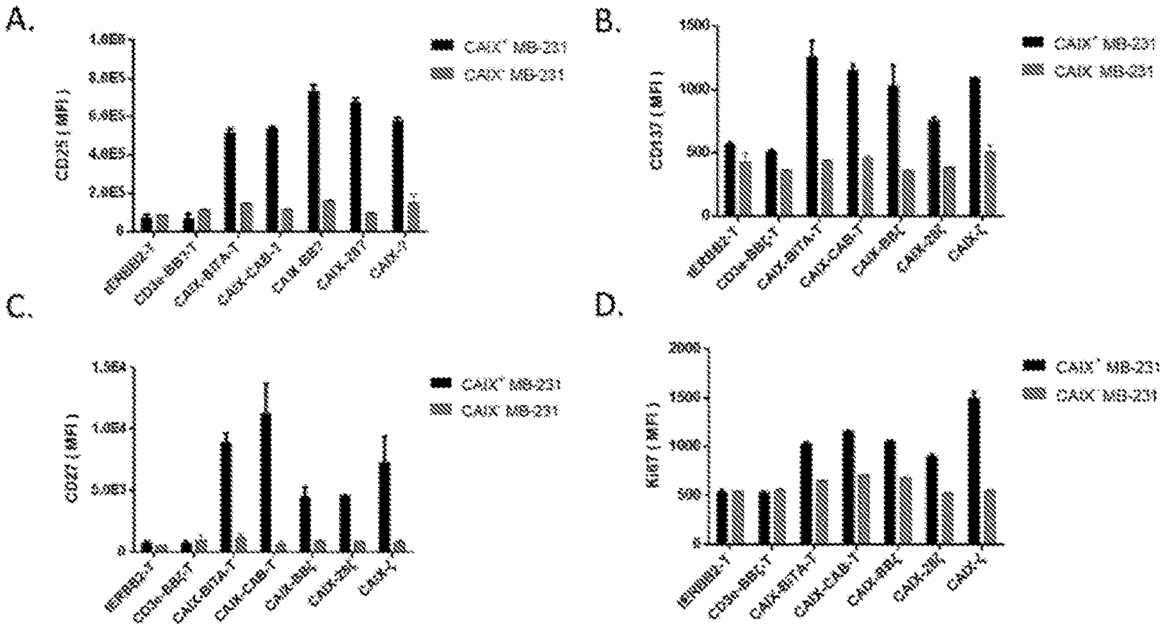
FIG. 10 shows a CAIX-CAB-T cell activation level assay (of the constructs from the second group of experiments).

In the second group of experiments, after CAIX-CAB-T cells and their control group cells were co-cultured with CAIX+ MB-231 cells or CAIX-MB-231 for 48 h, respectively, the changes in expression levels of CD137, CD25, CD27 and Ki67 on the surface of a T cell membrane were detected. The results were shown in FIG. 10. When CAIX-CAB-T and its control groups were co-cultured with CAIX-MB-231 cells, respectively, the expression levels of CD137, CD25, CD27 and Ki67 in CAIX-CAB-T and its control group immune cells were not significantly changed. After CAIX-CAB-T and its control groups were co-cultured with CAIX+ MB-231 cells, the expression levels of CD137, CD25, CD27 and Ki67 in T cells engineered by CAIX-BiTA, CAIX-CAB, first generation CAR and second generation CAR were significantly up-regulated. When T cells engineered by tERBB2 and CD3e-BBζ were co-cultured with CAIX+ MB-231 cells, respectively, no significant up-regulation of CD137, CD25, CD27 and Ki67 was detected. The above results indicated that the CAIX-CAB-T cell activation was dependent on CAIX antigen, and it was also demonstrated that CAB-T cells had comparable in vitro activation ability to the control group BiTA-T, the first generation CAR and the second generation CAR cells.

Figure 11:
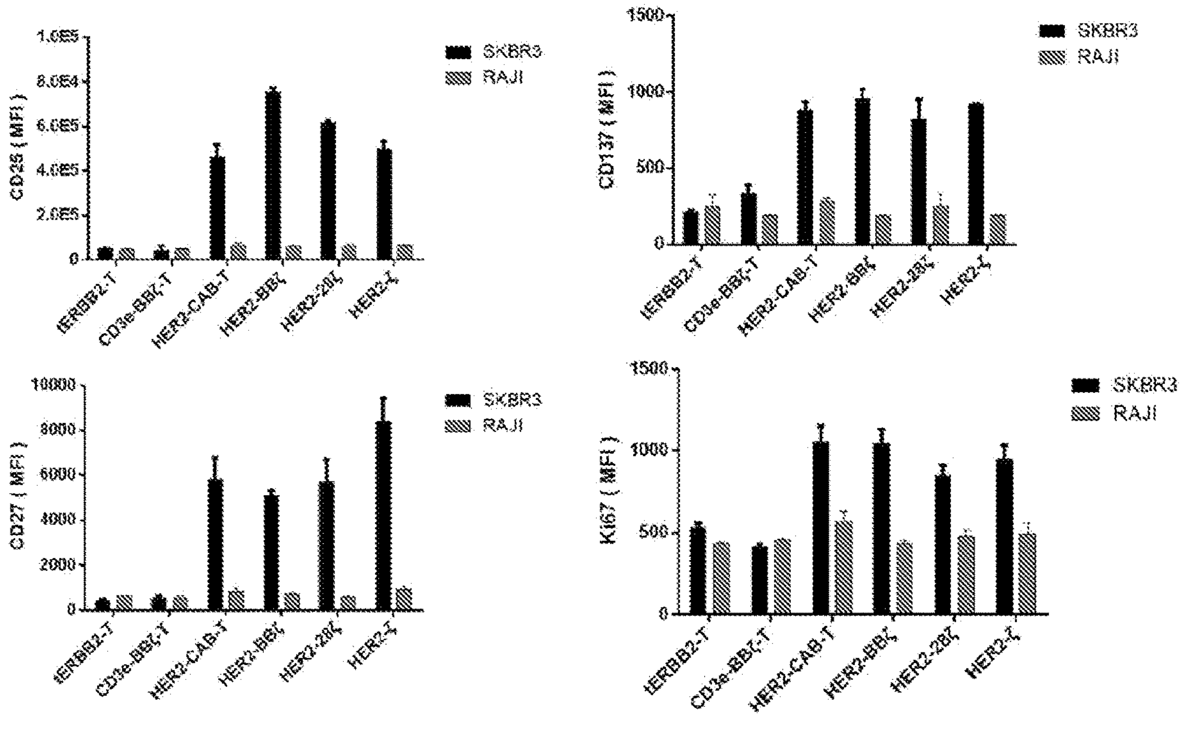
FIG. 11 shows an HER2-CAB-T cell activation level assay (of the constructs from the third group of experiments).
Figure 12:
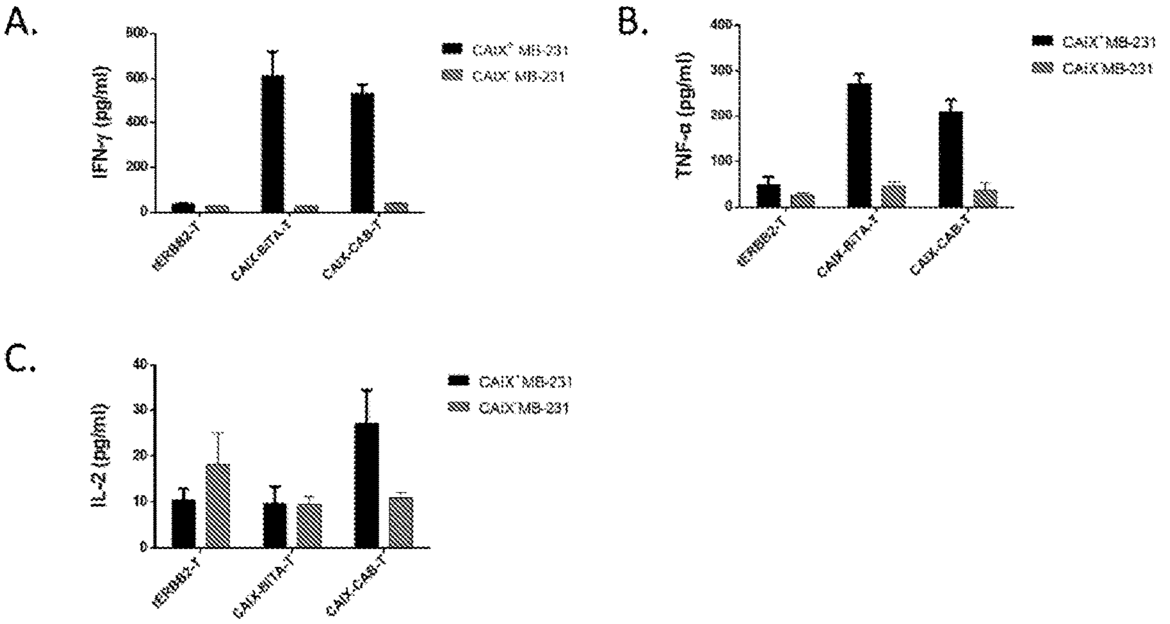
FIG. 12 shows a CAIX-CAB-T paracrine activated T cell level assay (of the constructs from the second group).

In a third group of experiments, we detected the in vitro activation ability of the HER2-CAB structure constructed using the Trastuzumab-derived scFv sequence. The results were shown in FIG. 11. After HER2-CAB-T cells and their control group cells were co-cultured with HER2-positive SKBR3 cell line or HER2-negative RAJI cell line for 48 h, respectively, the changes in the expression levels of CD137, CD25, CD27 and Ki67 on the surface of a T cell membrane were detected. The results were shown in FIG. 12. When HER2-CAB-T and its control groups were co-cultured with RAJI cells, respectively, the expression levels of CD137, CD25, CD27 and Ki67 in HER2-CAB-T and its control group immune cells were not significantly changed. After HER2-CAB-T and its control groups were co-cultured with HER2-positive SKBR3 cells, the expression levels of CD137, CD25, CD27 and Ki67 in T cells engineered by HER2-CAB, first generation CAR and second generation CAR were significantly up-regulated. When T cells engineered by tERBB2 and CD3e-BBζ were co-cultured with SKBR3 cells, respectively, no significant up-regulation of CD137, CD25, CD27 and Ki67 was detected. The above results indicated that HER2-CAB-T cell activation was dependent on HER2 antigen and it was also demonstrated that CAB-T cells had comparable in vitro activation ability to the control group BiTA-T, first generation CAR and second generation CAR cells.

Example 7

Analysis of Non-Engineered T Cells Activated by Paracrine CAB-T

The original intention for designing the CAB structure is to achieve the following effects: when encountering tumor cells, CAB-T activates its own anti-tumor activity, and meanwhile non-engineered T cells around CAB-T are activated by BiTA drugs secreted by CAB-T to achieve paracrine activation. In order to detect the paracrine activation function of CAB-T in T cells, we made a verification using a transwell experiment. Specifically, the experiment was performed by separating the CAB-T and non-engineered T cells using a physical barrier through a 0.4 μm Transwell system, CAB-T cells were placed in an upper chamber, and non-engineered T cells and tumor cells were placed in a lower chamber. Soluble BiTA secreted by CAB-T can enter the lower chamber freely through a 0.4 μm grid to activate the ability of the underlying non-engineered T cells to activate by recognizing tumor cells.

A specific experimental procedure was as follows:

1) $1\times10^6$ BiTA-T cells and $1\times10^6$ CAB-T were resuspended in 200 μL of X-VIVO 15 medium, respectively, and then added to the upper chamber of 0.4-μm Transwell (Coning, 3413).
2) $1\times10^6$ non-engineered T cells and $1\times10^6$ target cells were resuspended in 500 μL of X-VIVO-15 medium and added to the lower chamber of Transwell.
3) The upper chamber was carefully placed into the lower chamber and incubated in an incubator for 48 hours.
4) A culture plate co-cultured overnight was taken out, and 500 μL of cell supernatant in the lower chamber was taken out. After centrifugation at 300 g for 5 min, 150 μL of supernatant/well was pipetted using a multichannel pipette and transferred to a new 96-well cell culture plate for ELISA detection of IFN-γ/IL-2/TNF-α.

Results:

In the second group of experiments (FIG. 12), both BiTAs secreted by CAIX-BiTA-T and CAIX-CAB-T were able to activate the ability of the underlying non-engineered T cells to recognize CAIX-positive MB-231 tumor cells by Transwell pores, which exhibited high release levels of IFN-γ and TNF-α. At the same time, we found no significant change in IL-2 release levels, which was consistent with the results of the study in Example 9.

Figure 13:
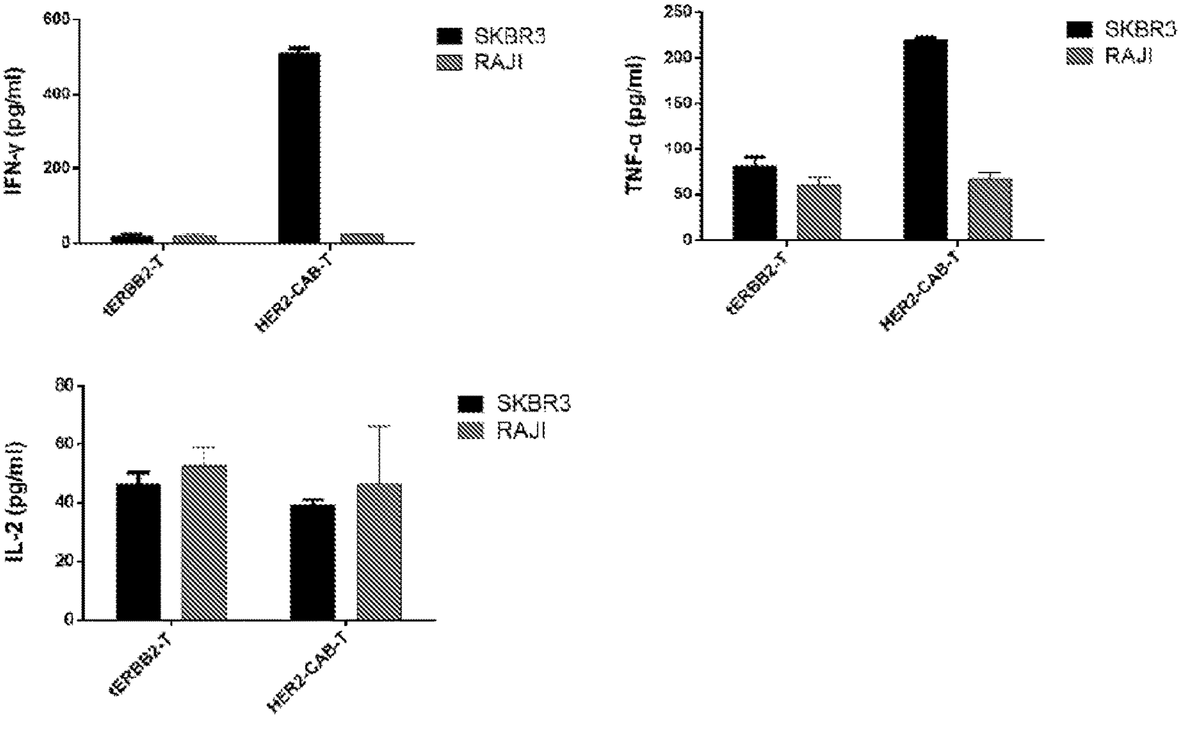
FIG. 13 shows an HER2-CAB-T paracrine activated T cell level assay (of the constructs from the third group).

It can be seen from the results shown in the third group of experiments (FIG. 13) that HER2-CAB-T also showed the same paracrine activation for the ability of non-engineered T cells to recognize tumor antigens. HER2-CAB-T cells, but not control tERBB2-T cells, can activate the underlying non-engineered T cells in Transwell to recognize HER2-positive SKBR3 tumor cells. HER2-CAB-T did not help the non-engineered T cells to recognize HER2-negative RAJI cells.

Both the second and third groups of experiments demonstrated that the CAB-T structure can activate the ability of non-engineered T cells to recognize tumor cells via paracrine BiTA.

Example 8

Analysis of Immune Checkpoint Expression Levels and Cell Differentiation Phenotypes of CAB-T Cell The expression level of immune checkpoint proteins on immune cells and the differentiation phenotype of immune cells have a great relationship with the therapeutic effect of adoptive T cells. Therefore, lower expression levels of immune checkpoints and higher proportions of memory T cells both predict better clinical response rates. We used flow cytometry to detect the effect of the CAB structure on the immune checkpoint expression levels and cell phenotypes of T cells engineered by the CAB structure.

A specific analysis procedure was as follows:

1) 96-well cell culture plates co-cultured overnight was centrifuged at 300 g for 5 min, 200 μL FACS buffer was added to each well, and centrifuged at 300 g for 5 min.
2) The supernatant centrifuged was removed, and the cells were resuspended with 200 μL FACS buffer, and centrifuged at 300 g for 5 min.
3) The antibody was diluted with FACS buffer to prepare antibody mix (100 μL/well)

| | |
|---|---|
| BV421 Mouse Anti-Human CD3 (BD Bioscience, 562426) | 1:500 dilution |
| APC Mouse Anti-Human TIM-3 (Biolegend, 345012) | 1:200 dilution |
| Alexa Fluor 647 Mouse Anti-Human LAG-3 (Biolegend, 369304) | 1:200 dilution |
| APC Mouse Anti-Human CD279 (BD Bioscience, 558694) | 1:200 dilution |
| PE-cy5 Mouse Anti-Human CD45RA (BD Bioscience, 555490) | 1:200 dilution |
| BV605 Mouse Anti-Human CCR7 (BD Bioscience, 563711) | 1:200 dilution |

4) The supernatant centrifuged was removed, and 100 μL of the antibody mix was added to each well, and incubated at 4° C. for 30 min in the dark.
5) 200 μL FACS buffer was added to each well, and centrifuged at 300 g for 5 min, and the supernatant was discarded.
6) The supernatant centrifuged was removed and step 2.5 was repeated.
7) 200 μL of Fixation/Permeabilization solution (BD bioscience, 554715) was added and incubated at 4° C. for 20 min.
8) Centrifugation was performed at 300 g for 5 min; the supernatant centrifuged was removed, 200 μL of 1×Perm/Wash buffer (BD bioscience, 554715) was added, resuspended, and centrifuged at 400 g for 5 min; and washing was performed twice.
9) The antibody FITC Mouse Anti-Flag (Biolegend, 637318) was diluted with FACS buffer by 1:1000 dilution.
10) Centrifugation was performed at 400 g for 5 min; the supernatant centrifuged was removed, and washing was performed twice.
11) Flow cytometry detection was performed using FSC/SSC gating to obtain desired lymphocyte populations, and CD3 BV421+ and Flag FITC+ cell populations were selected to obtain live CAR-T cells.

Figure 14:
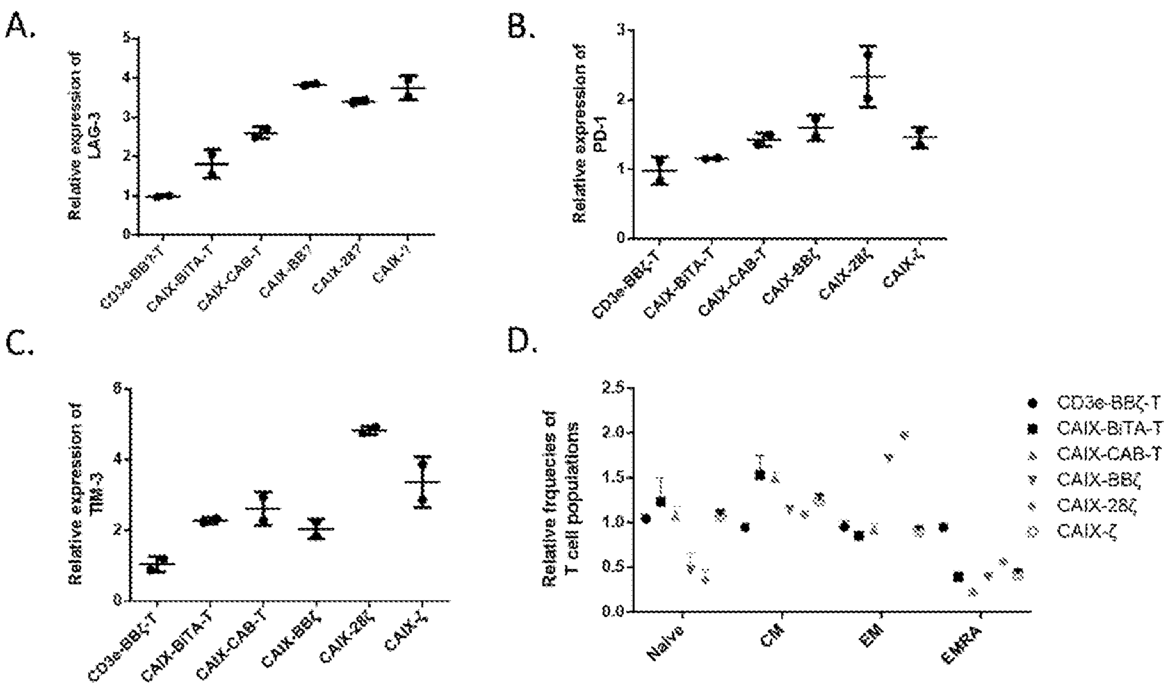
FIG. 14 shows CAIX-CAB-T and its control cellular immune checkpoint expression level and cell differentiation phenotype analysis (of the constructs from the second group).

Results:

It can be seen from the results of the second group of experiments (FIG. 14) that after co-culture with CAIX-positive MB-231 cells, the expression levels of immune checkpoint protein on the surface of CAIX-CAB-T cells, including LAG-3, PD-1 and TIM-3, were at lower levels than second generation CAR-T engineered by CAIX-28ζ, the expression levels of PD-1 and TIM-3 on CAB-T cells were basically the same as the CAIX-BBζ second generation CAR-T, and the expression level of LAG-3 in CAB-T cells was slightly lower than that in second generation CAR-T engineered by CAIX-BBζ. Lower expression levels of immune checkpoint indicated the clinical advantage of CAB-T cells compared to second generation CAR-T.

In addition, in the second group of experiments, we also used CD45RA and CCR7 for differentiation phenotype analysis of immune cells. Differentiation marker proteins were: initial T cells ($CD45RA^{+}$, $CCR7^{+}$), central memory T cells ($CD45RA^{-}$, CCR7+), effector memory T cells ($CD45RA^{-}$, $CCR7^{-}$), and effector T cells for terminal differentiation ($CD45RA^{+}$, $CCR7^{-}$), respectively. It can be seen from the results shown in FIG. 14.D that compared with the second generation CAR-T, the cell proportion of the initial differentiated T cell phenotype and the central memory T cell phenotype of CAIX-CAB-T was significantly higher than that of the second generation CAR-T cells, while the proportion of effector memory T cells of second generation CAR-T cells was significantly higher than that of CAB-T cells. The more central memory T cell phenotype predicted better clinical efficacy, showing the advantage of CAB-T in the differentiated state compared to the second generation CAR-T.

Figure 15:
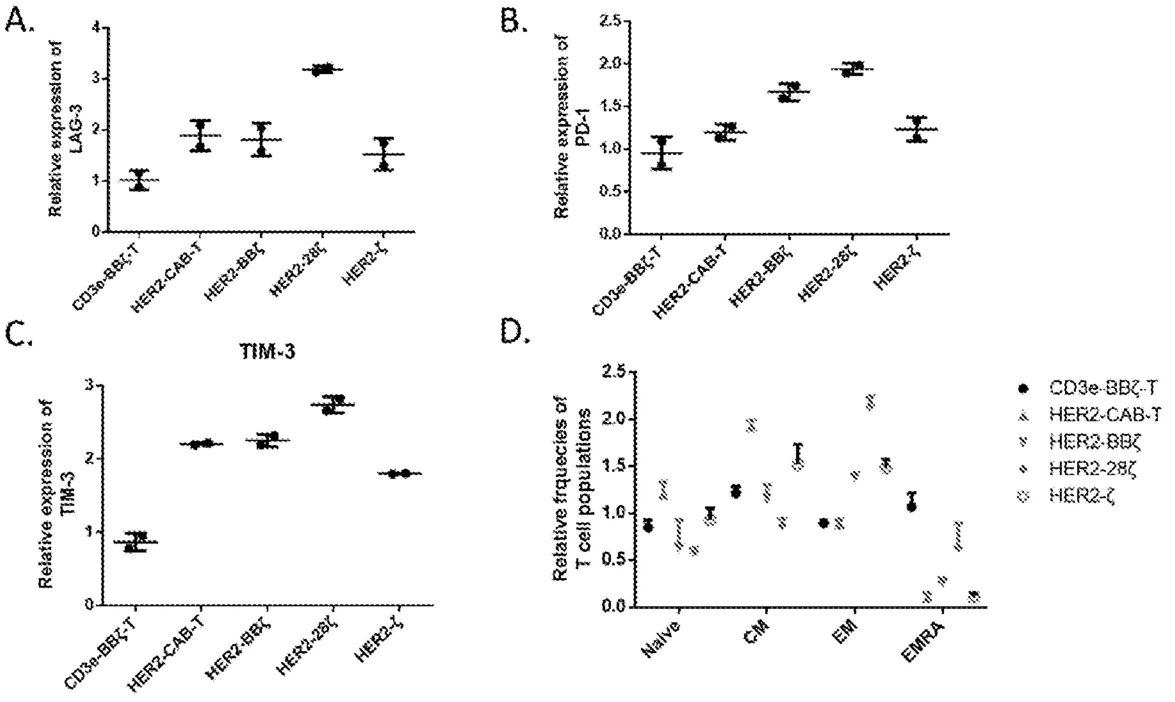
FIG. 15 shows HER2-CAB-T and its control cellular immune checkpoint expression level and cell differentiation phenotype analysis (of the constructs from the third group of experiments).

It can be seen from the results shown in the third group of experiments (FIG. 15) that the expression status of the immune checkpoint and the differentiation result of the cell phenotype for HER2-CAB-T were basically consistent with the analysis result of CAIX-CAB-T. Namely, the expression level of the immune checkpoint of HER2-CAB-T was lower than that of second generation CAR-T engineered by CAIX-28ζ, and was basically equal to or slightly lower than that of second generation CAR-T engineered by CAIX-BBζ. The differentiation state of HER2-CAB-T also had a higher proportion of central memory T cell phenotype than the second generation CAR-T.

Example 9

Antigen Dependent Killing Activity of CAB-T

Whether CAB-T cells have in vitro killing activity is the key basis for judging the potential clinical efficacy of CAB-T. To verify the tumor killing activity of CAB-T, we used an LDH method for detection.

A specific experimental procedure was as follows:

1) Experimental wells, effector cell control wells, target cell control wells, target cell maximum release wells, medium control wells, and volume control wells were arranged, respectively; the experimental procedure was performed according to the CytoTox 96® Non-Radioactive Cytotoxicity Assay kit (Promega, G1781) standard procedure.
2) Different target-effector ratios were set, i.e. number of effector cells:number of target cells=0:1, 1:1, 5:1, 10:1, and 20:1
3) Number of cells: $1\times10^{4}$ target cells, 50 μL/well.
4) For experimental wells, 100 ul of cells at different dilution ratios of effector cells:target cells=0:1, 1:1, 5:1, 10:1, and 20:1 (effector cells 50 μL+target cells 50 μL) were added to cell culture plate in triplicate;
5) For effector cell control wells, effector cells: target cells=0:0, 1:0, 5:0, 10:0, and 20:0, in duplicate;
6) For target cell control wells, 50 μL of target cells at $1\times10^{4}$/well and 50 μL of medium were added;
7) For target cell maximum release wells, 50 μL of target cells at $1\times10^{4}$ and 50 μL of medium were added, and 10 μL of lysate was added 1 h before the sample was collected;
8) For medium control well, 100 μL of medium was added;
9) For volume control wells, 100 μL of medium was added, 10 μL of the lysate was added to the target cell maximum release wells 1 h before the sample was collected, meanwhile 10 μL of lysate was added, and incubation was performed at 37° C.

10) According to the designed layout, the samples were added into a plate, and incubated at 37° C. with 5% $CO_2$ for 24 h, or 36 h, or 48 h;

11) Assay buffer was taken from a refrigerator at −20° C. and dissolved in a refrigerator at 4° C. in the dark. During use, 12 ml of assay buffer was added to a flask of substrate mix and mixed.

12) The culture plate was centrifuged at 250 g for 4 min, and 50 μL/well of cellular supernatant was transferred to a new ELISA plate.

13) 50 μL/well of substrate mix was added to the new ELISA plate (12 mL of assay buffer was added to a flask of mix and mixed in the dark).

14) Incubation was performed at room temperature for 30 min in the dark, and 50 μL/well stop solution was added.

15) The absorbance was read in a microplate reader at the detection wavelength of OD=490 nm in 1 h.

16) The cell killing ratio (%) was calculated based on an OD value

Experimental well=effector-target ratio−medium control (mean)

Spontaneous release of target cell=target cell control−medium control (mean)

Spontaneous release of effector cell=effector cell control−medium control (mean)

Maximum release of target cell=maximum release of target cells (mean)−volume control (mean)

Cell killing ratio (%)=(experiment−spontaneous release of target cell−spontaneous release of effector cell)/(maximal release of target cell−spontaneous release of target cell).

Results:

BiTA secreted by CAB-T can activate CAB-T cells themselves and their surrounding non-engineered T cells in a target antigen-dependent manner, and kill target antigen-positive tumor cells; meanwhile, CAB-T cells express CD3e-BBζ, so that CAB-T can rely on endogenous TCR activation, furthermore CD3e-BBζ can enhance the activation level of CAB-T cells, and in turn promotes CAB-T to release more BiTA, and these effects reinforce each other. Therefore, in theory, CAB-T should have a stronger killing effect on tumor cells than BiTA-T.

Figure 16:
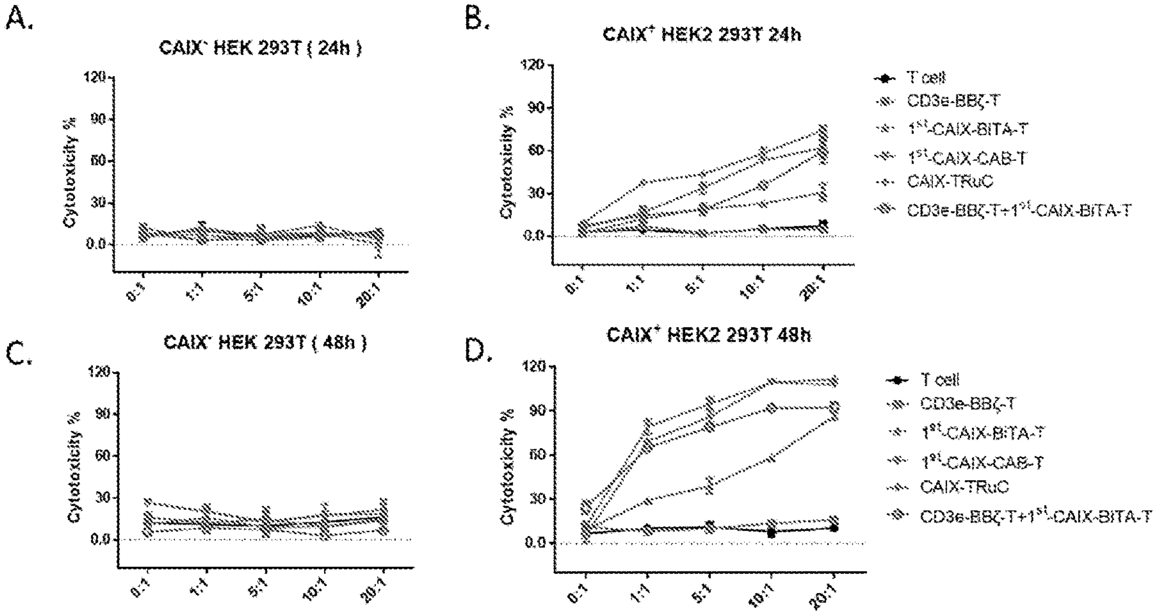
FIG. 16 shows a CAIX-CAB-T and its control cell-mediated tumor killing ability assay (of the constructs from the first group of experiments).

In the first group of experiments, in order to detect the killing effect of CAIX-CAB-T cells on CAIX$^+$ HEK 293T target cells, we chose CAIX-CAB-T cells as effector cells of the experimental group for killing effect detection. The effector cells were co-cultured with the target cells for 24 and 48 h at an effector-target ratio of 0:1, 1:1, 5:1, 10:1, and 20:1, respectively, and the supernatant was taken to determine the ability of T cells to kill target cells at different effector-target ratios. It can be seen from the results of FIG. 16 that 1st-CAIX-CAB-T cells and their control group T cells had no killing effect on CAIX-HEK293T; while 1st-BiTA-T cells, 1st-CAIX-CAB-T, CAIX-TRuC-T, and mixed T cells of CD3e-BBζ-T and 1st-BiTA-T showed different degrees of killing ability on CAIX+ HEK 293T cells, and this killing ability increased with the increase of the effector-target ratio. Moreover, the killing on target cells by CAIX-CAB-T and its control group T cells became more significant with the prolongation of co-culture time, and the killing effect of co-culture for 48 h was significantly stronger than that of co-culture for 24 h. The CD3e-BBζ-T and non-engineered T cell control groups showed no killing effect on CAIX+ HEK 293T cells. In addition, 1st-CAIX-CAB-T, CAIX-TRuC-T, and mixed T cells of CD3e-BBζ-T and 1st-BiTA-T had comparable killing ability on CAIX+ HEK 293T cells and were superior to 1st-BiTA-T in killing ability. From this, we can determine that the killing ability of CAIX-CAB-T on tumor cells depended on the expression of its target antigen, and its killing ability was comparable to that of the control group CAIX-TRuC-T cells. In addition, BiTA-T and CD3e-BBζ-T also showed synergistic effects on target cells killing.

Figure 17:
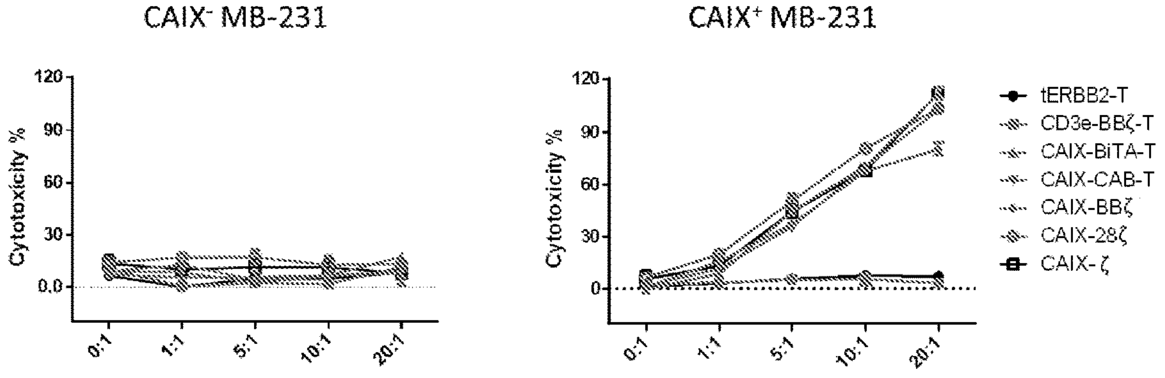
FIG. 17 shows a CAIX-CAB-T and its control cell-mediated tumor killing ability assay (of the constructs from the second group of experiments).

The method for the second group of experiments was identical to that of the first group of experiments. We detected the killing ability of CAIX-CAB-T and its control cells on CAIX$^+$MB-231 or CAIX-MB-231 tumor cells. The effector cells were co-cultured with the target cells for 36 h at an effector-target ratio of 0:1, 1:1, 5:1, 10:1, and 20:1, respectively, and the supernatant was taken to determine the ability of T cells to kill target cells at different effector-target ratios. It can be seen from the results shown in FIG. 17 that CAIX-CAB-T and its control cells had no killing effect on CAIX$^-$MB-231 control tumor cells, and CAIX-CAB-T and first and second generation CAR-T cells targeting CAIX exhibited comparable killing ability on CAIX$^+$MB-231 cells. At the same time, tERBB2-T and CD3e-BBζ-T control group cells had no killing ability on CAIX$^+$MB-231 cells. CAIX-CAB-T was shown to have comparable killing ability on tumor cells as first and second generation CAR-T, and this killing ability was target antigen-dependent. It should be noted that CAIX-CAB-T and CAIX-BiTA-T did not show differences in killing ability on target cells in this group of experiments due to higher transduction or different donor cell sources or the like.

Figure 18:
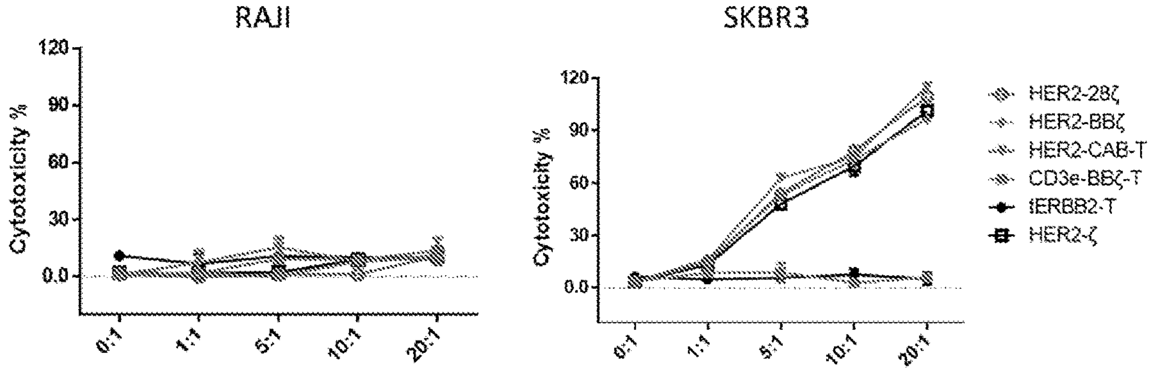
FIG. 18 shows an HER2-CAB-T and its control cell-mediated tumor killing ability assay (of the constructs from the third group of experiments).

The third group of experiments was identical to the first and second groups of experiments. We detected the ability of HER2-CAB-T and its control cells to kill HER2 positive tumor cells SKBR3 or HER2 negative tumor cells RAJI. The effector cells were co-cultured with the target cells for 36 h at an effector-target ratio of 0:1, 1:1, 5:1, 10:1, and 20:1, respectively, and the supernatant was taken to determine the ability of T cells to kill target cells at different effector-target ratios. It can be seen from the results shown in FIG. 18 that HER2-CAB-T and its control cells had no killing effect on HER2-negative RAJI cells; and HER2-CAB-T and HER2-targeted first and second generation CAR-T cells exhibited comparable killing ability on SKBR3. At the same time, tERBB2-T and CD3e-BBζ-T control cells had no killing ability on SKBR3 cells. HER2-CAB-T was shown to have comparable killing ability on tumor cells as first and second generation CAR-T, and this killing ability was target antigen-dependent.

Example 10

Figure 19:
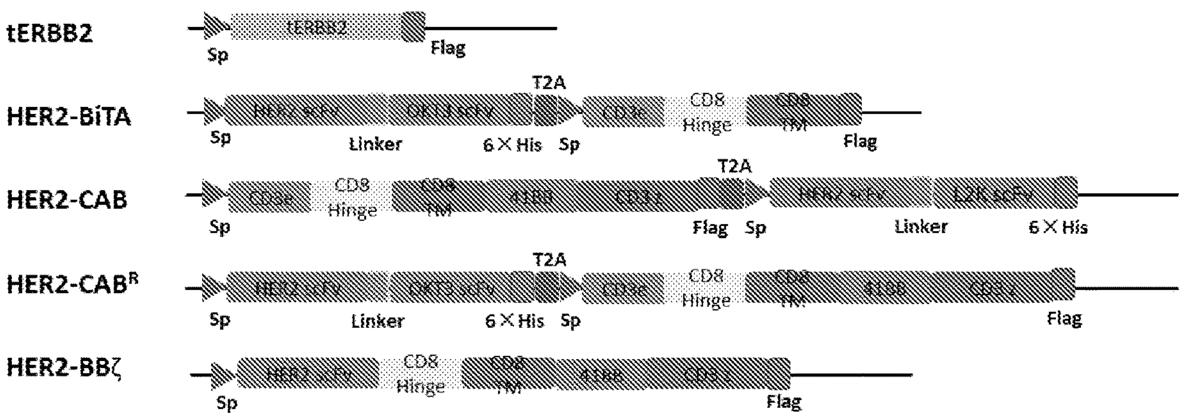
FIG. 19 shows the structures of the CAB-T according to the fourth group of experiments and its control group.
Figure 20:
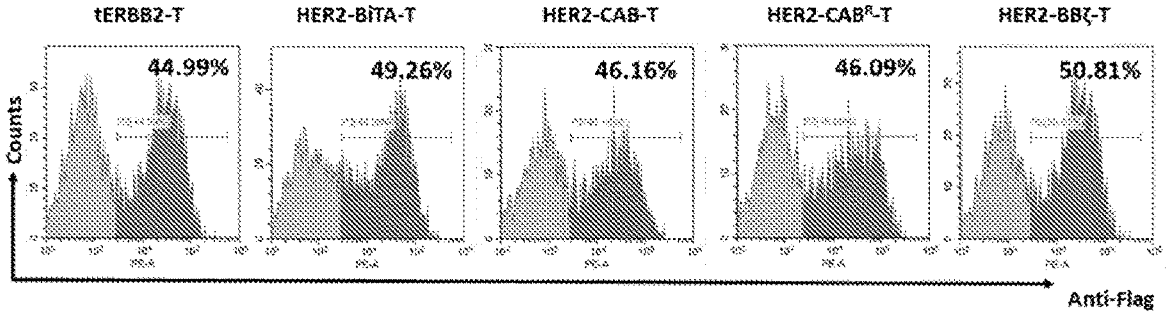
FIG. 20 shows the transduction frequency results of T cell engineered by the fourth group of structures.

In Vitro Activity Comparison of Different CAB Structures With BiTA and Second Generation CAR Due to the different expression levels of CD3e-BBζ and BiTA in cells, we attempted to analyze the differences between different structures of CAB and BiTA and second generation CAR. We first designed a group of CAB and its control structures as shown in FIG. 19, including: tERBB2, HER2-BiTA, HER2-CAB, HER2-CAB$^R$ (DNA SEQ ID NO.: SEQ 67, AA SEQ ID NO.: SEQ 68) and HER2-BBζ. The lentivirus was packaged according to the method described in Example 2 using the vectors carrying the above structures and the T cells were infected according to the method described in Example 3. The positive frequency of the infected cells was detected according to the method described in Example 4, and the detection results were shown in FIG. 20. The positive frequencies of engineered T cells were basically equal.

Figure 21:
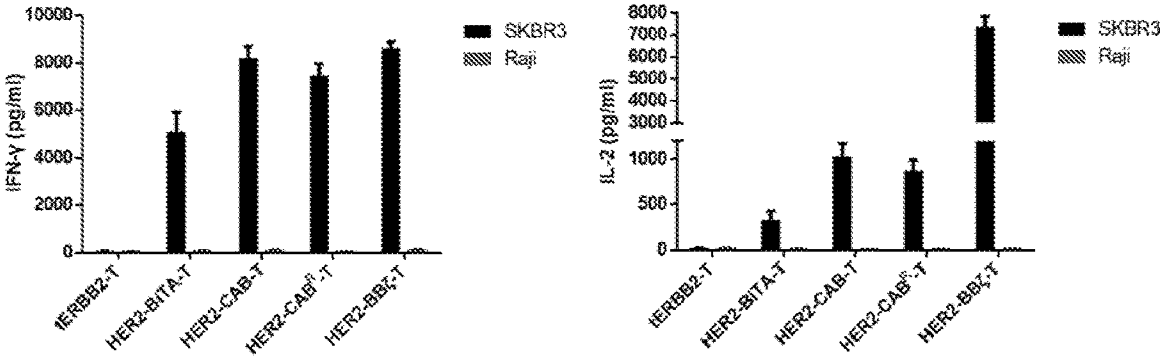
FIG. 21 shows an HER2-CAB-T cell activation level assay of the constructs from (the fourth group of experiments).

To identify the in vitro activation ability of the engineered T cells, according to the method described in Example 5, after the engineered T cells were co-cultured with HER2-negative RAJI cells and HER2-positive SKBR3 cells, respectively, release levels of cytokines IL-2 and IFNγ were detected. The results were shown in FIG. 21. The levels of cytokine release after activation of HER2-CAB-T and HER2-$CAB^R$-T cells were basically equal.

Figure 22:
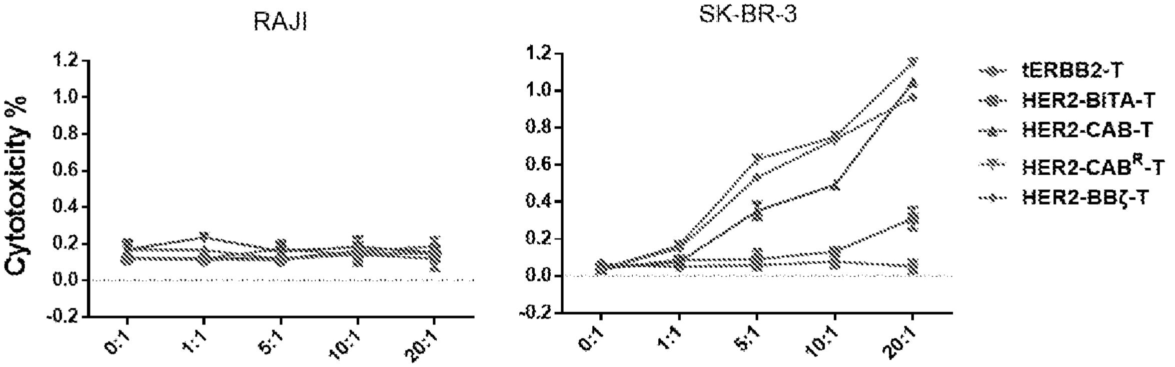
FIG. 22 shows an HER2-CAB-T and its control cell-mediated tumor killing ability assay (of the constructs from the fourth group of experiments).

To identify differences in the in vitro killing ability of the engineered T cells, we detected the in vitro killing ability of each of the engineered T cells on RAJI and SKBR3 cells according to the method described in Example 9. Compared with the HER2-CAB structure, since the HER2-$CAB^R$ structure had BiTA in the front and the CD3e-BBζ structure in the back, theoretically, HER2-$CAB^R$-T can secrete higher levels of BiTA. We speculated that HER2-$CAB^R$-T had better in vitro killing ability than HER2-CAB-T cells. As shown in FIG. 22, the results were consistent with our hypothesis, namely, HER2-$CAB^R$-T demonstrated superior in vitro killing ability over HER2-CAB-T cells.

Example 11

In Vivo Efficacy of CAIX CAB-T

The anti-tumor activity of CAB-T in mouse tumor models is the key basis for judging the potential clinical efficacy of CAB-T. To verify the anti-tumor activity of CAB-T in a mouse tumor model, the following validation experiments were performed.

A specific experimental procedure was as follows.

$CAIX^+$MDA-MB-231 Cell Expansion Culture and Inoculation

1) Enough $CAIX^+$MDA-MB-231 cells were cultured and expanded in vitro, the cells were collected after trypsin digestion, washed with PBS for 3 times and counted, the cell density was adjusted to $15\times10^6$ cells/ml with a 80% RPMI-1640 basic medium containing 20% Matrigel, the cells were placed into a 50 ml centrifuge tube, the opening of the centrifuge tube was tightly covered and sealed with a sealing film, and the centrifuge tube was passed into an SPF grade animal room through a transfer window.
2) 68 female 8-week-old NCG severe immunodeficient mice purchased in advance were fed adaptively for 1 week, and then the hair at right abdomen of each mouse was removed with a razor. $CAIX^+$MDA-MB-231 cells with a density of $15\times10^6$ cells/ml were dissociated and thoroughly mixed with a 1 ml pipette, and 0.2 ml of cells were subcutaneously inoculated with a 1 ml syringe to the right abdomen of each NCG mouse, namely, each NCG mouse was inoculated with $3\times10^6$ $CAIX^+$MDA-MB-231 cells, and the cells were observed daily for subcutaneous tumor formation in NCG mice, and each NCG mouse was numbered 6 days after inoculation using an ear tag with a number;

Grouping, Administration, and Measurement of $CAIX^+$ MDA-MB-231 Tumor-Bearing Mice 3) 10 days after inoculation, the maximum broad axis W and the maximum long axis L of the subcutaneous tumor at the right abdomen of each NCG mouse were measured using a vernier caliper, and the body weight of each mouse was weighed using an electronic balance. The subcutaneous tumor volume at the right abdomen of each NCG mouse was calculated according to the tumor volume T=½×W×W×L. The mice with oversized and undersized tumors were excluded, and NCG mice were averagely divided into 11 groups according to the average tumor volume with 6 mice in each group;
4) The grouping was performed according to the following administration scheme for each group and the corresponding reagents or cells were injected. In hCAIX-BiTA (DNA SEQ ID NO.: SEQ 71, AA SEQ ID NO.: SEQ 72), hCAIX-CAB (DNA SEQ ID NO.: SEQ 73, AA SEQ ID NO.: SEQ 74), and hCAIX-BBζ (DNA SEQ ID NO.: SEQ 75, AA SEQ ID NO.: SEQ 76) structures for engineering T cells, the antibody sequences for recognizing CAIX are all derived from the humanized sequence of the VHH amino acid sequence SEQ ID NO. 18.

Administration Scheme For Each Group

| Group | Testing sample | Dosage of administration | Times of administration | Mode of administration |
|---|---|---|---|---|
| PBS | PBS | N/A | Once on Day 10 and Once on Day 13 | Tail vein injection |
| NT cell 2.5 × 10^6/mouse | NT | 2.5 × $10^6$/mouse | Once on Day 10 and Once on Day 13 | Tail vein injection |
| hCAIX-BiTA-T cell 2.5 × 10^6/mouse | hCAIX-BiTA-T | 2.5 × $10^6$/mouse | Once on Day 10 and Once on Day 13 | Tail vein injection |
| hCAIX -BiTA-T cell 0.75 × $10^6$/mouse | hCAIX -BiTA-T | 0.75 × $10^6$/mouse | Once on Day 10 and Once on Day 13 | Tail vein injection |
| hCAIX -BiTA-T cell 0.25 × $10^6$/mouse | hCAIX -BiTA-T | 0.25 × $10^6$/mouse | Once on Day 10 and Once on Day 13 | Tail vein injection |
| hCAIX -CAB-T cell 2.5 × $10^6$/mouse | hCAIX -CAB-T | 2.5 × $10^6$/mouse | Once on Day 10 and Once on Day 13 | Tail vein injection |
| hCAIX -CAB-T cell 0.75 × $10^6$/mouse | hCAIX -CAB-T | 0.75 × $10^6$/mouse | Once on Day 10 and Once on Day 13 | Tail vein injection |

-continued

| Group | Testing sample | Dosage of administration | Times of administration | Mode of administration |
|---|---|---|---|---|
| hCAIX -CAB-T cell 0.25 × 10⁶/mouse | hCAIX -CAB-T | 0.25 × 10⁶/mouse | Once on Day 10 and Once on Day 13 | Tail vein injection |
| hCAIX -BBζ-T cell 2.5 × 10⁶/mouse | hCAIX -BBζ-T | 2.5 × 10⁶/mouse | Once on Day 10 and Once on Day 13 | Tail vein injection |
| hCAIX -BBζ-T cell 0.75 × 10⁶/mouse | hCAIX -BBζ-T | 0.75 × 10⁶/mouse | Once on Day 10 and Once on Day 13 | Tail vein injection |
| hCAIX -BBζ-T cell 0.25 × 10⁶/mouse | hCAIX -BBζ-T | 0.25 × 10⁶/mouse | Once on Day 10 and Once on Day 13 | Tail vein injection |

5) Tumor volume and body weight of the mice were measured twice a week. The body weight and tumor volume of the mice were measured for the last time 37 days after inoculation of the tumor cells. After the mice were euthanized, the tumors of each mouse were dissected, the tumor weight was weighed, and the tumors were photographed.

Results and Discussion

Figure 23A:
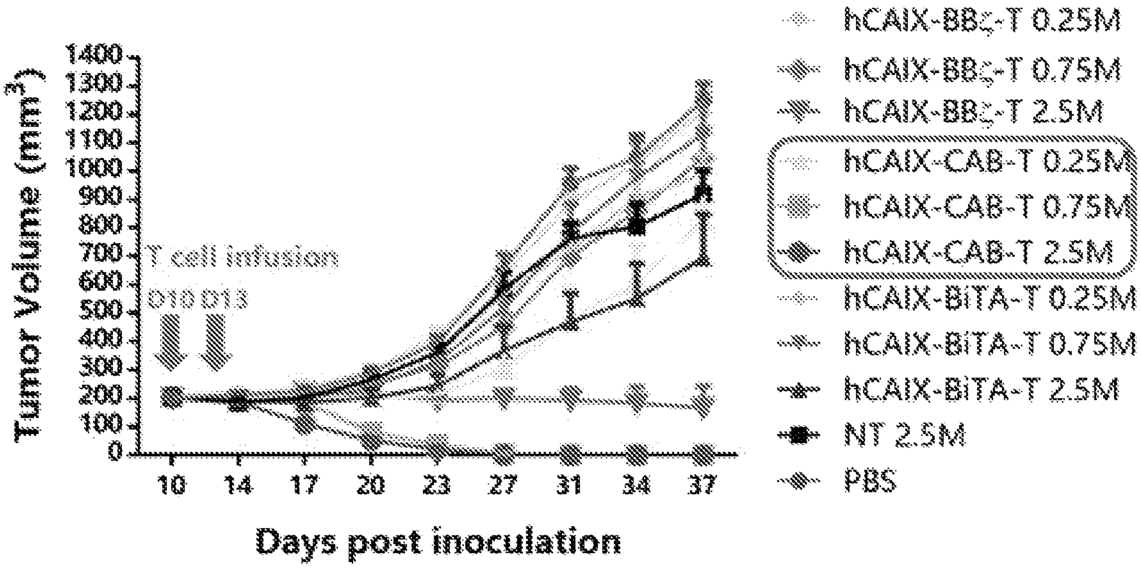
FIG. 23A shows a CAIX$^{+}$MDA-MB231 tumor growth inhibition assay in NCG humanized mice at different doses for CAIX-CAB-T and its control group cells.
Figure 23B:
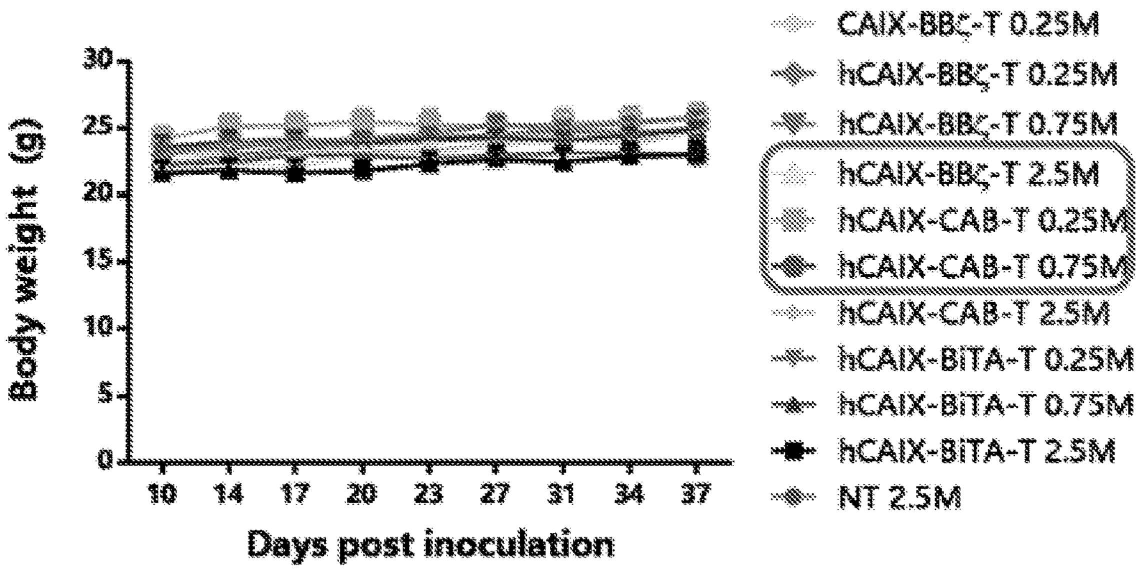
FIG. 23B shows the body weight change of the mice in the assay as shown in FIG. 23A.
Figure 23C:
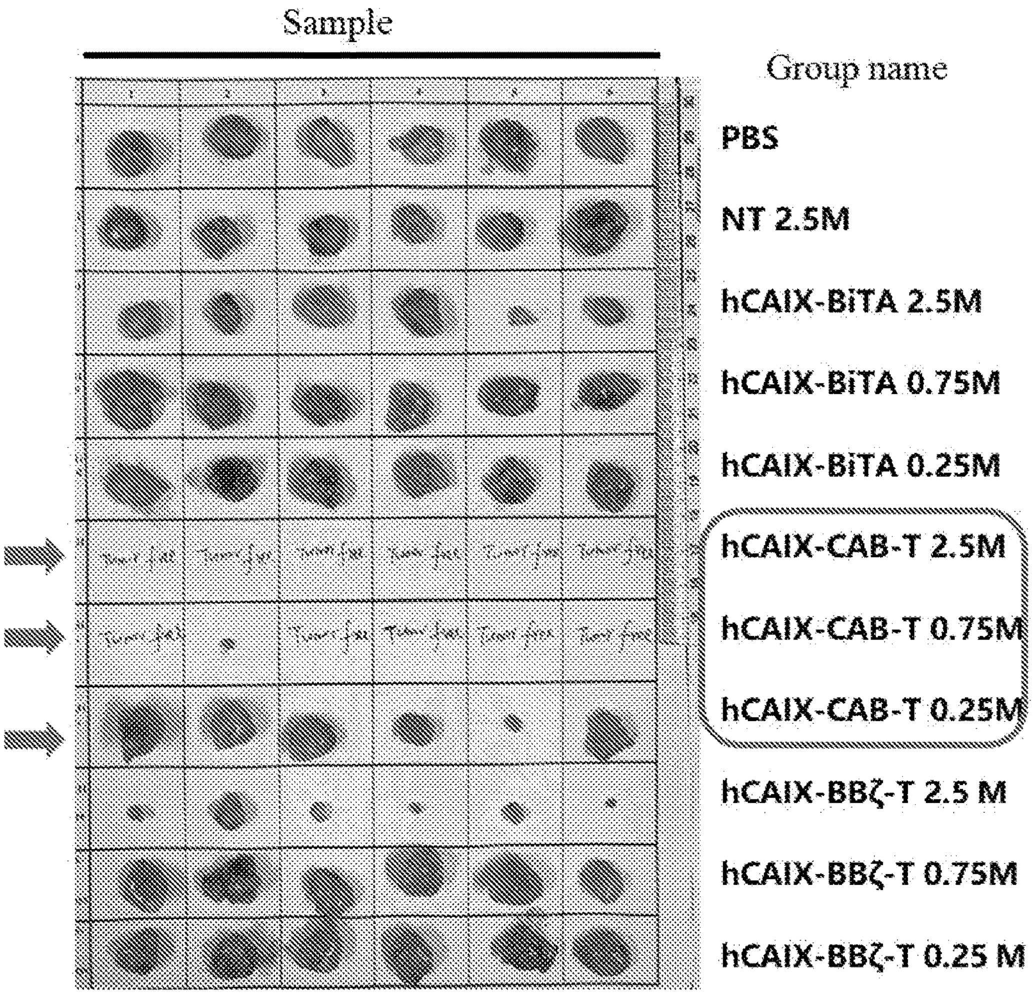
FIG. 23C shows the images of tumors from mice in the assay as shown in FIG. 23A.
Figure 23D:
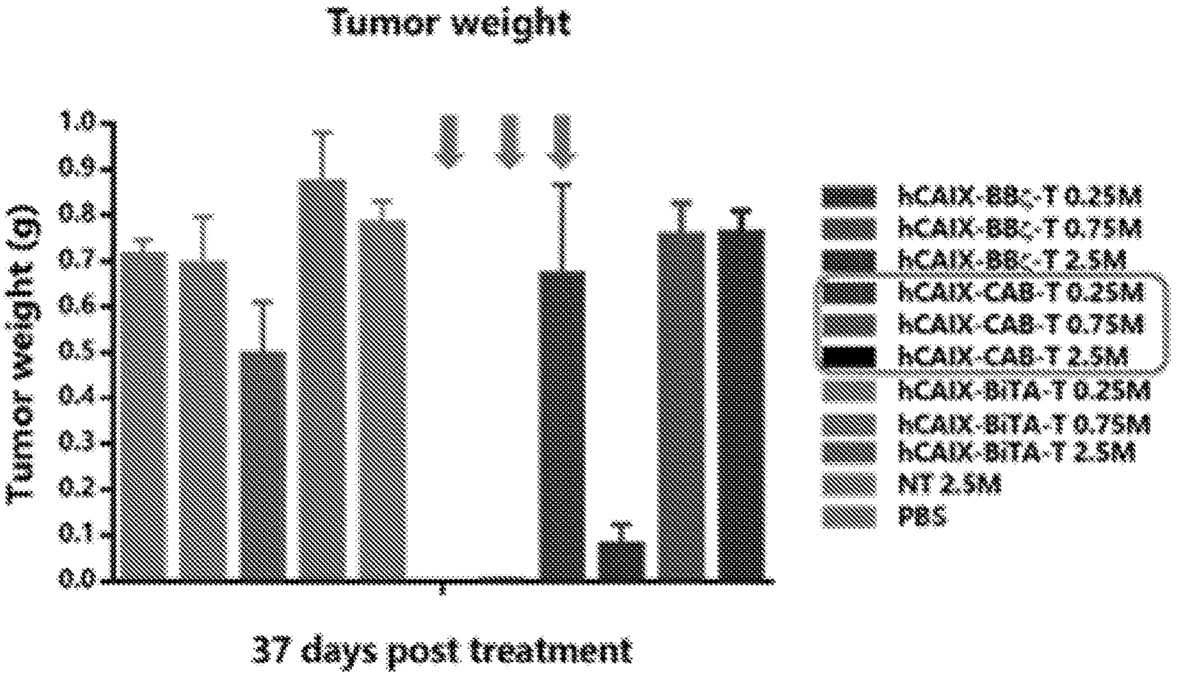
FIG. 23D shows tumor weight of the mice in the assay as shown in FIG. 23A.

The tumor growth curve, tumor picture and tumor weight of each group of mice are shown in the figures, the tumors of mice in the PBS group and the NT group increased rapidly with the prolongation of the inoculation time, indicating that the CDX transplantation model was successfully established in this experiment; compared with the PBS group and NT group, the hCAIX-BiTA-T cell group and the hCAIX-BBζ-T cell group showed the inhibition effect on tumor growth only at $2.5\times10^6$/mouse, while the hCAIX-CAB-T cell group had certain effects for three dose groups and these effects were dose-dependent, in which all tumors in the $2.5\times10^6$/mouse group regressed, and 5 mice in the $0.75\times10^6$/mouse group had tumor regression; the hCAIX-CAB-T cell group was significantly superior to the hCAIX-BiTA-T cell group and the hCAIX-BBζ-T cell group at the same dose. The result trends of tumor growth curve, tumor picture, and tumor weights of each group were consistent (FIG. 23A, C, and D). There was no significant decrease in body weight of the mice in each group throughout the experimental period (FIG. 23B), indicating the safety of each test sample.

Example 12

In Vivo Efficacy of HER2 CAB-T

The anti-tumor activity of HER2 CAB-T was verified in M-NSG immune-deficient mice tumor model by the following experiments.

NCI-N87 Cell Expansion Culture and Inoculation

1) NCI-N87 cells were cultured and expanded in vitro, the cells were collected after trypsin digestion, washed with PBS for 3 times and counted, the cell density was adjusted to $10\times10^6$ cells/ml with a 80% RPMI-1640 basic medium containing 20% Matrigel, the cells were placed into a 50 ml centrifuge tube, the opening of the centrifuge tube was tightly covered and sealed with a sealing film, and the centrifuge tube was passed into an SPF grade animal room through a transfer window.
2) 32 female 8-week-old NSG severe immuno-deficient mice were fed adaptively, and the hair at right abdomen of each mouse was removed with a razor. NCI-N87 cells with a density of $10\times10^6$ cells/ml were dissociated and thoroughly mixed with a 1 ml pipette, and 0.2 ml of cells were subcutaneously inoculated with a 1 ml syringe to the right abdomen of each NSG mouse, namely, each NSG mouse was inoculated with $3\times10^6$ NCI-N87 cells, and the cells were observed daily for subcutaneous tumor formation in NSG mice, and each NSG mouse was numbered 6 days after inoculation using an ear tag with a number.

Grouping, Administration, and Measurement of NCI-N87 Tumor-Bearing Mice 3) 6 days after inoculation, the maximum broad axis W and the maximum long axis L of the subcutaneous tumor at the right abdomen of each NSG mouse were measured using a vernier caliper, and the body weight of each mouse was weighed using an electronic balance. The subcutaneous tumor volume at the right abdomen of each NCG mouse was calculated according to the tumor volume $T=\frac{1}{2}\times W\times W\times L$. The mice with oversized and undersized tumors were excluded, and NSG mice were averagely divided into 4 groups according to the average tumor volume with 6 mice in each group;
4) The grouping was performed according to the following administration scheme for each group and the corresponding reagents or cells were injected. In NT (DNA SEQ ID NO.: SEQ 33, AA SEQ ID NO.: SEQ 34), HER2 CAB$^R$-T (DNA SEQ ID NO.: SEQ 67, AA SEQ ID NO.: SEQ 68), HER2 CAB-T (DNA SEQ ID NO.: SEQ 49, AA SEQ ID NO.: SEQ 50), and HER2 CAR-T structures for engineering T cells, the scFv antibody sequences for recognizing HER2 are all derived from Trastuzumab amino acid sequence SEQ ID NO. 66.

Administration Scheme For Each Group

| Group | Day 0 Dosage of administration | Day 2 Dosage of administration | Mode of administration |
|---|---|---|---|
| NT cell | 5.0 × 10⁶/mouse | 3.0 × 10⁶/mouse | Tail vein injection |
| HER2 CAB$^R$-T | 5.0 × 10⁶/mouse | 3.0 × 10⁶/mouse | Tail vein injection |
| HER2 CAB-T | 5.0 × 10⁶/mouse | 3.0 × 10⁶/mouse | Tail vein injection |
| HER2 CAR-T | 5.0 × 10⁶/mouse | 3.0 × 10⁶/mouse | Tail vein injection |

5) Tumor volume and body weight of the mice were measured twice a week. The body weight and tumor volume of the mice were measured for the last time 48 days after inoculation of the tumor cells. After the mice were euthanized, the tumors of each mouse were dissected, the tumor weight was weighed, and the tumors were photographed.

Results and Discussion

The tumor growth curve and tumor picture of each group of mice are shown in the figures, the tumors of mice in the NT group increased rapidly with the prolongation of the inoculation time, indicating that the CDX transplantation model was successfully established in this experiment; compared with the NT group, all other 3 engineered T cell treated group showed certain tumor growth inhibition. In contrast to the mild tumor growth inhibition and 2 tumor-free mice in HER2 CAR-T treated group, both HER2-CAB$^R$-T and HER2-CAB-T showed a much better tumor growth inhibition, and with 5 tumor-free mice and 2 tumor-free mice respectively.

Figure 24A:
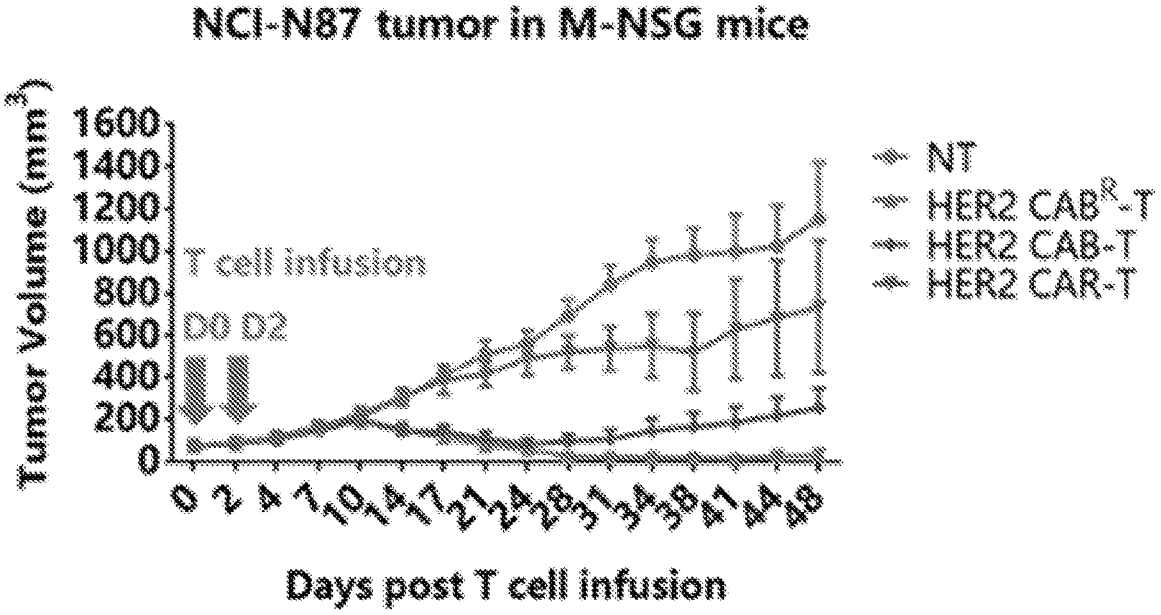
FIG. 24A shows a NCI-N87 tumor growth inhibition in M-NSG humanized mice treated with HER2-CAB-T and its control T cells.
Figure 24B:
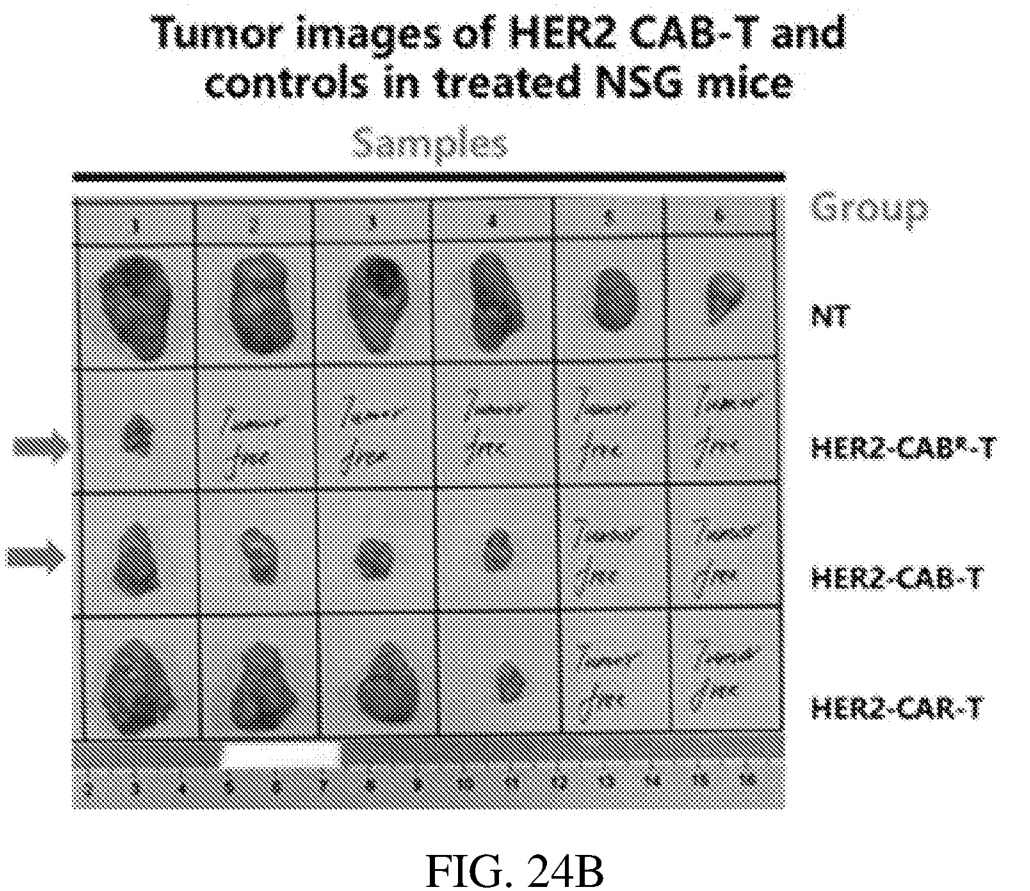
FIG. 24B shows the images of tumors from mice in the assay as shown in FIG. 24A.
Figure 24C:
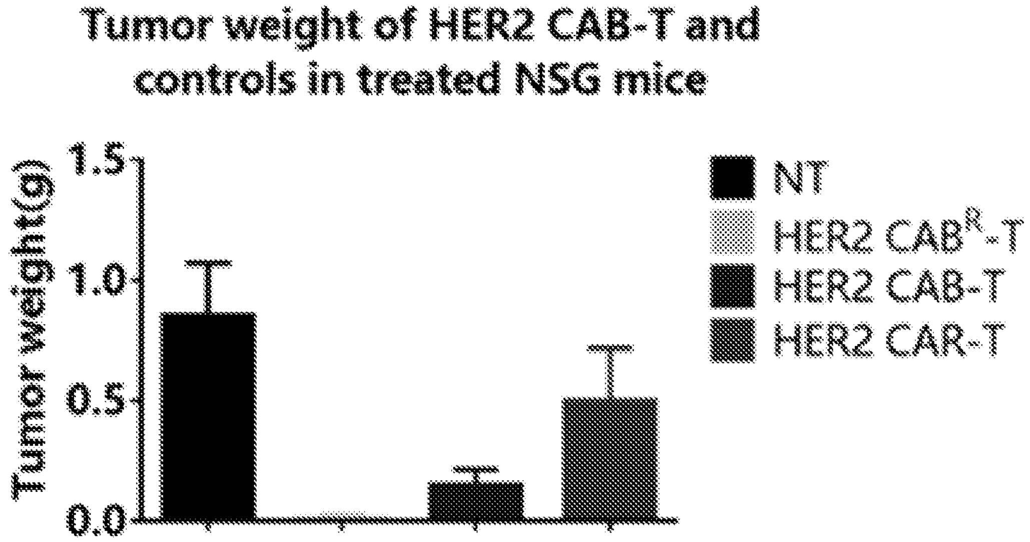
FIG. 24C shows a statistical tumor weight of the mice in the assay as shown in FIG. 24A.

The result trends of tumor growth curve, tumor picture, and tumor weights of each group were consistent (FIG. 24A, C, and D). There was no significant decrease in body weight of the mice in each group throughout the experimental period, indicating that each test sample had good safety.

Example 13

Dasatinib Works as a Safety-Switch and Inhibits Cytokine Release of CAB-T

As a live cell therapy, CAB-T may lead to cytokine release syndrome (CRS) and on-target, off-tumor toxicities etc. and clinical management of CRS includes the anti-IL-6R agonist Tocilizumab and steroids treatment. Here, we developed the method to manage potential toxicities using Dasatinib.

Dasatinib has been developed as an inhibitor of BCR-ABL fusion protein, and is clinically approved for chronic myelogenous leukemia and acute lymphoblastic leukemia treatment. In addition, dasatinib was also reported can blocks the lymphocyte-specific protein tyrosine kinase (LCK) and thereby inhibits phosphorylation of CD3ζ and ZAP70, thereby ablating signaling in CAR and TCR signaling. The following example demonstrate that dasatinib is able to inhibit cytokine release of CAB-T dramatically.

$1\times10^5$ effector cells (CAIX CAB-T or HER2 CAB-T) and $1\times10^5$ target cells (CAIX+MDA-MB231 or SKBR3) were seeded at 200 μL/well with a gradient concentration of dasatinib (100 nM, 50 nM, 25 nM, 12.5 nM, 6.25 nM, 0 nM) in 96-well cell culture plate, the plate were centrifuged at 300 g for 5 min after co-cultured overnight, and then 150 μL of the supernatant/well was pipetted into a new 96-well cell culture plate using a multichannel pipette, and cytokine detections were performed as showed in Example 5.

Result and Discussion

As shown in FIG. 25A, 25B and FIG. 26A, 26B, dasatinib inhibited IFNγ and IL-2 secretion effectively in both activated CAIX CAB-T and HER2 CAB-T at a low dose around 25 nM. The result imply that dasatinib could be used as a safety-switch to control the potential CRS syndrome and on-target, off-tumor toxicity of CAB-T in clinical treatment.

Example 14

Dasatinib Works as a Safety-Switch and Inhibits Killing Activity of CAB-T

As described in Example 13, T cell therapy has on-target, off-tumor toxicity potential issues clinically. To manage the potential toxicity of CAB-T, inhibition of the killing activity of CAB-T was evaluated using dasatinib.

We used LDH cytotoxicity assay method to detect the killing inhibition capability of dasatinib. The detailed protocol was described in Example 9. Briefly, $5\times10^4$ effector cells (CAIX CAB-T or HER2 CAB-T) and $1\times10^4$ target cells (CALX+MDA-MB231 or SKBR3) were co-cultured with a gradient concentration of dasatinib (100 nM, 50 nM, 25 nM, 12.5 nM, 6.25 nM, 0 nM), Cytotoxicity of CAB-T to its target cells were determined in 2-hour intervals over a period of 12 hours [effector-to-target cell (E:T) ratio, 5:1].

Result and Discussion

Figure 25A:
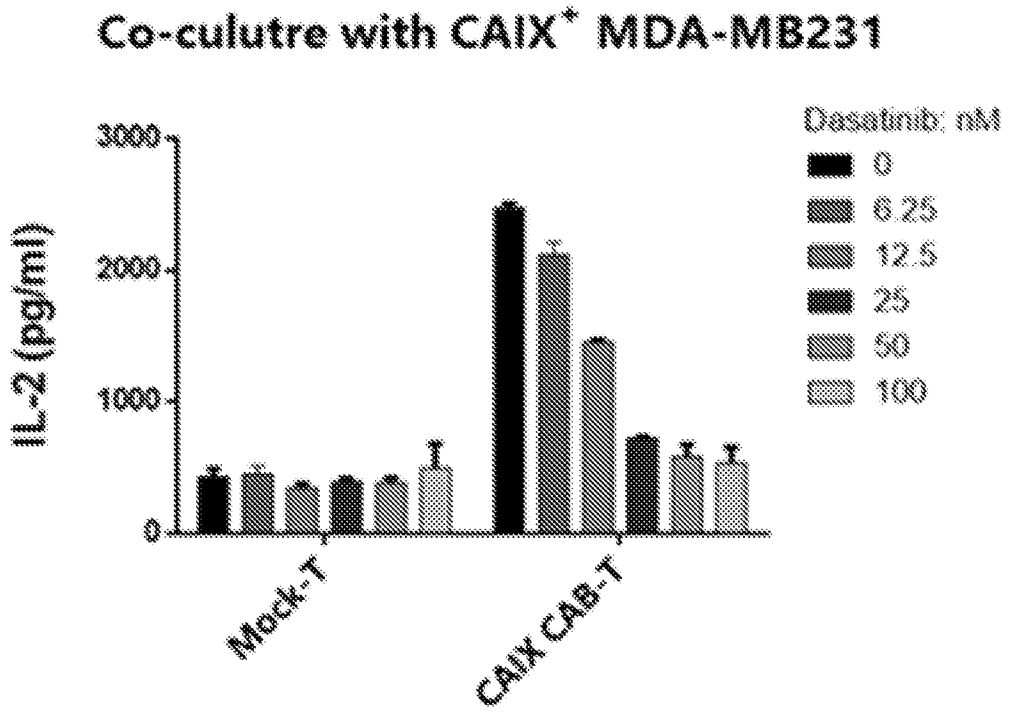
FIG. 25A shows Dasatinib inhibits IL-2 secretion of activated CAIX CAB-T at low concentrations.
Figure 25B:
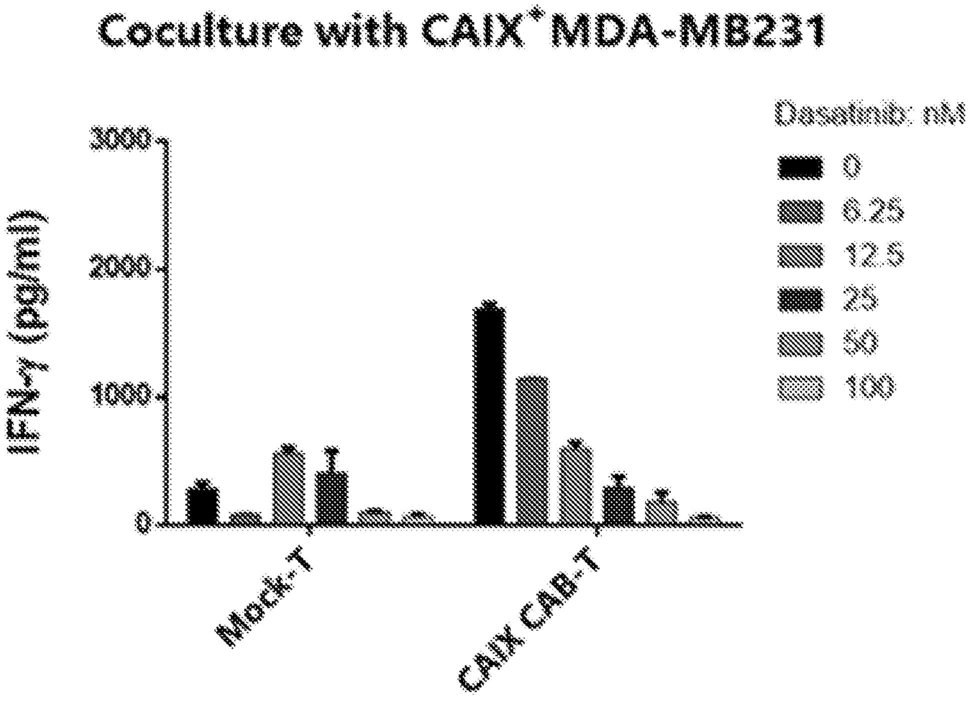
FIG. 25B shows Dasatinib inhibits IFN-γ secretion of activated CAIX CAB-T at low concentrations.
Figure 25C:
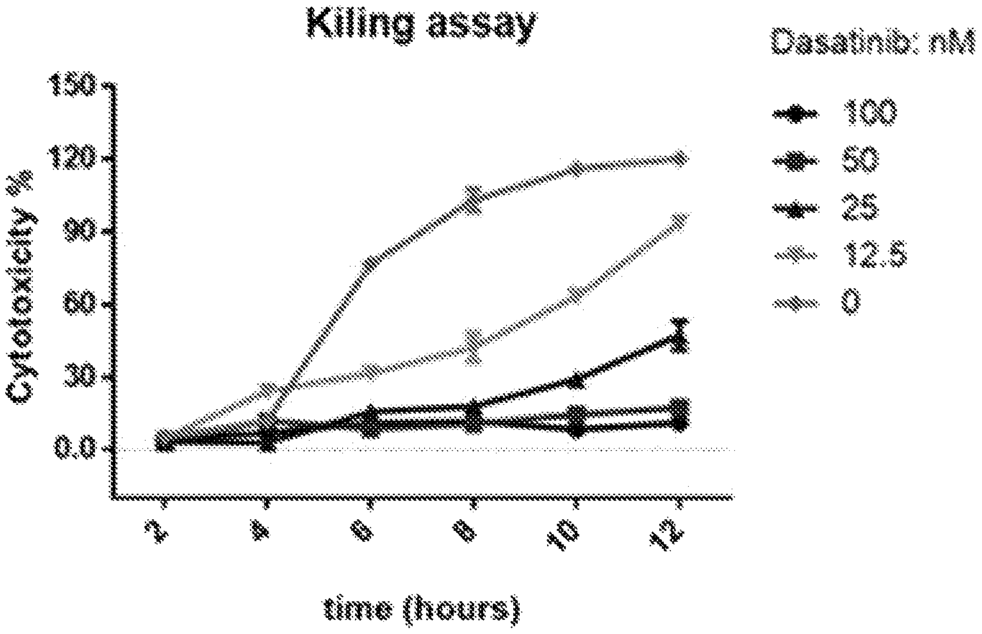
FIG. 25C shows Dasatinib inhibits the killing activity of CAIX CAB-T at low concentrations.
Figure 26A:
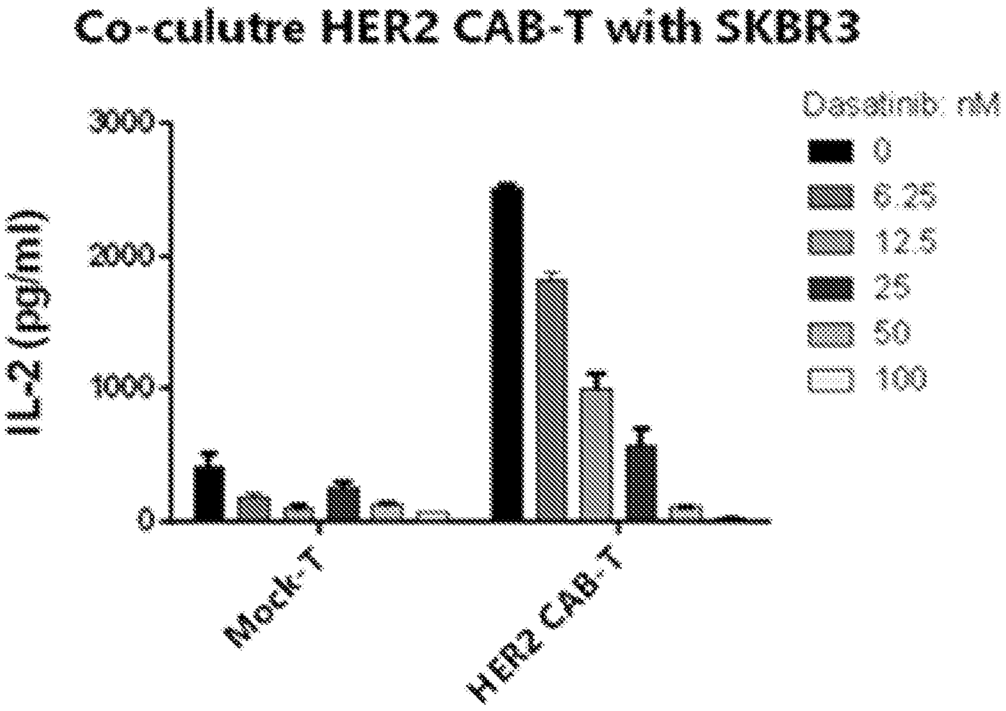
FIG. 26A shows Dasatinib inhibits IL-2 secretion of activated HER2 CAB-T at low concentrations.
Figure 26B:
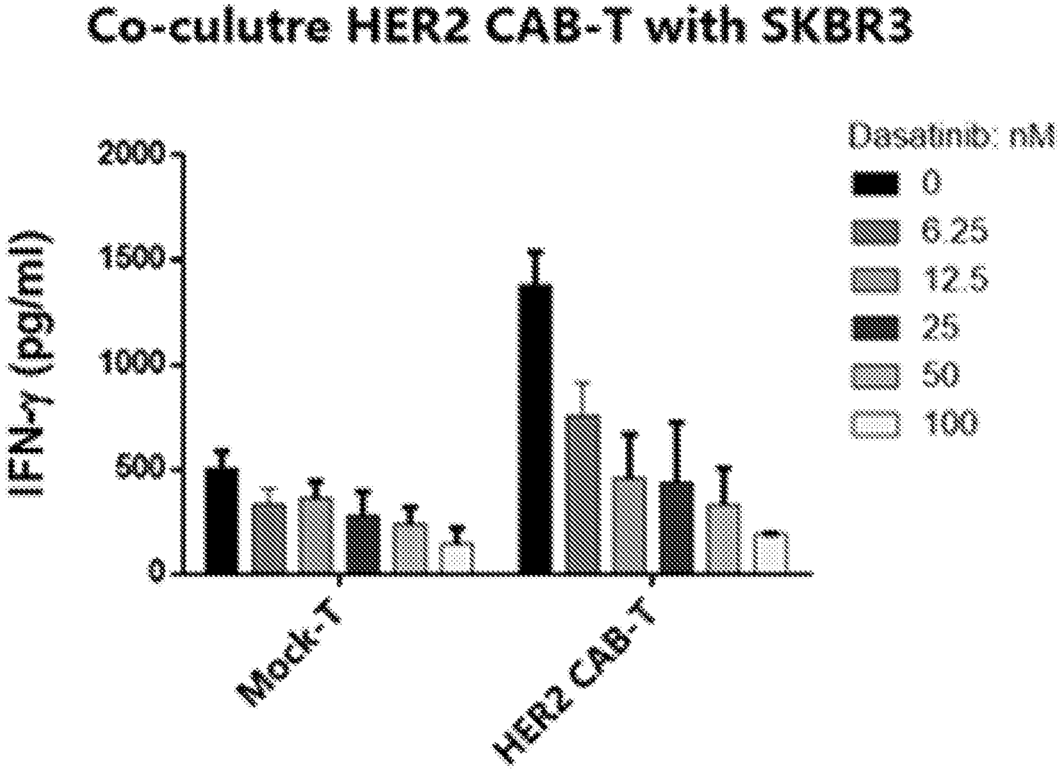
FIG. 26B shows Dasatinib inhibits IFN-γ secretion of activated HER2 CAB-T at low dose concentrations.
Figure 26C:
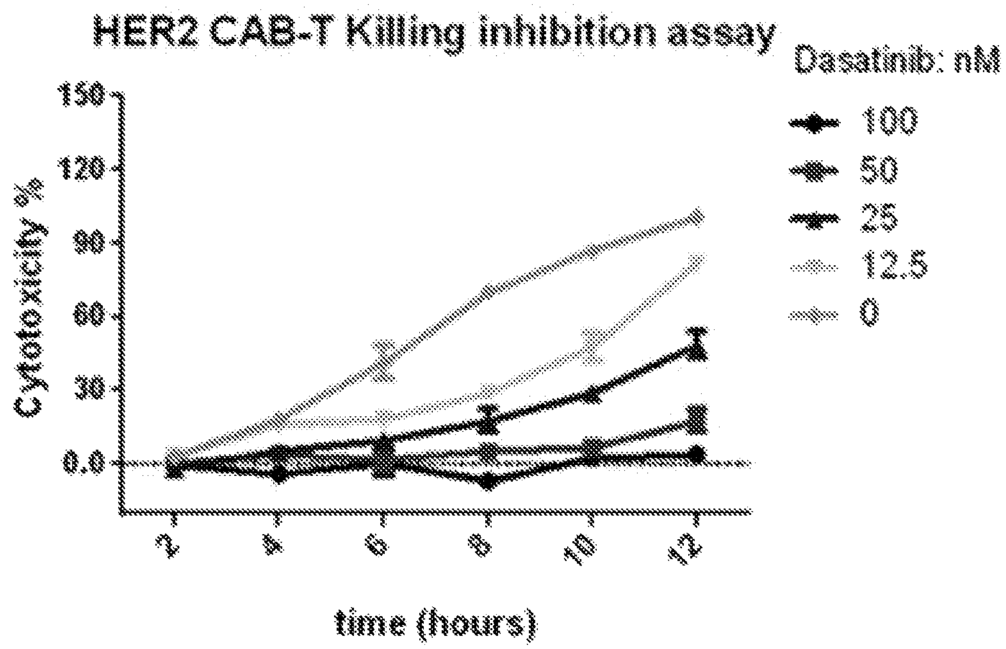
FIG. 26C shows Dasatinib inhibits the killing activity of HER2 CAB-T at low concentrations.

As shown in FIG. 25C and FIG. 26C, dasatinib inhibited cytotoxicity of CAIX CAB-T and HER2 CAB-T effectively to their target cells at a low dose around 50 nM. The result imply that dasatinib could be used as a safety-with to control the potential on-target, off-tumor toxicity of CAB-T in clinical treatment.

Summary and Discussion:

The CAB-T technology utilizes BiTA secreted by itself to simultaneously recognize chimeric CD3 or tumor antigen and endogenous CD3 in T cells, and thereafter induces tumor antigen-dependent endogenous TCR activation and chimeric CD3 activation. Both activations of endogenous TCR complexes and chimeric CD3 are dependent on the level of expression and secretion of BiTA by CAB-T cells. Thus, BiTA can induce CAB-T cells by the way of autocrine and induce non-engineered T cell activation in the tumor microenvironment by the way of paracrine; meanwhile, CAB-T cells can release higher levels of BiTA in tumor tissues after activation in tumor tissues, thereby mobilizing the activation and anti-tumor effects of more non-engineered T cells in tumor tissues.

Therefore, compared with TRuC-T and TAC-T, CAB-T does not only have the advantage of activating endogenous TCR signals, but also mobilizes the anti-tumor activity of infiltrating T cells in tumor tissues, and theoretically has better therapeutic potential for solid tumors. In addition, unlike BiTE drugs, BiTA drugs that are continuously secreted by CAB-T cells solve the clinical application problem of short half-life of the single drug of BiTE. In addition, since BiTA targeting the target antigen will exert the maximum effect in the tumor microenvironment where the CAB-T cells reach, and will not be enriched at a high concentration in a non-tumor tissue site, it has better safety and greater clinical application potential, compared with the systemic administration of the single drug of BiTE.

The mechanism of action and clinical application potential of CAB-T are stated as follows.

1) In tumor tissues, BiTA, which is underexpressed in CAB-T cells, can bind to its own endogenous TCR complex or CD3e-BBζ in an autocrine fashion (FIG. 27B), thereby stimulating CAB-T to release more BiTA to achieve a local activation loop (FIG. 27C). This allows CAB-T to achieve the maximum activation levels at the local tumor site, exerting its greatest anti-tumor effect, and achieving safety and effectiveness similar to the local administration of drugs at the tumor site. It is anticipated that CD3e-BBζ would form heterodimers with endogenous CDδ or CD3γ chains on T cell membranes, and hence further enhancing CD3-based signaling.
2) Binding and activation of chimeric CD3e in CAB-T by autocrine BiTA (FIG. 27A) confers sensitivity-enhanced proliferation and activation capacity on CAB-T compared to non-engineered T cells, further enhancing antitumor activity of CAB-T.
3) Activation of CAB-T (FIG. 27A, B, and C) and non-engineered T cells (FIG. 27D) by autocrine and paracrine of BiTA, respectively, solves the problem where CAR-T cells cannot activate endogenous TCR signals, conferring a potential for treating solid tumors with CAB-T cells.

4) CAB-T can be used as a drug synthesis plant for BiTA, which solves the problem of the short in vivo half-life of BiTA; the activation of CAB-T depends on the release level of BiTA, and the two rely on each other and cooperate with each other to collectively determine the safety and effectiveness of CAB-T for clinical application.

Figure 27:
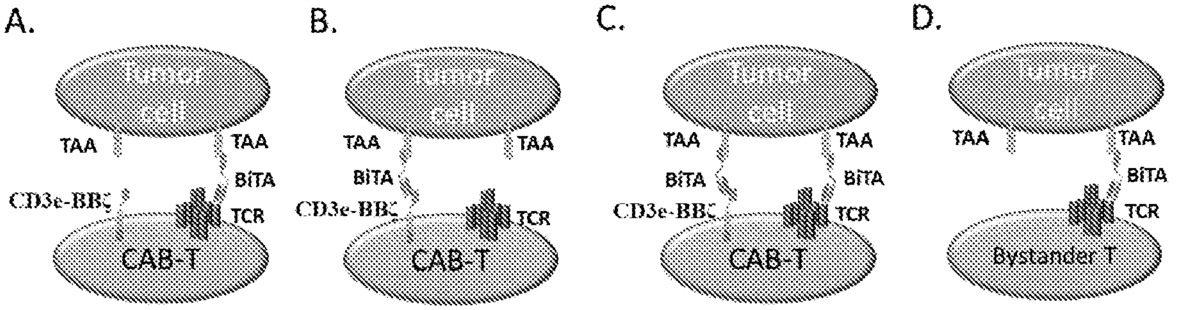
FIG. 27 shows a schematic diagram of the mechanism of action of CAB-T.

The schematic diagram of the mechanism of action of CAB-T is shown in FIG. 27.

All documents mentioned in the present disclosure are cited as references herein, as if each document is cited separately as a reference. In addition, it should be understood that various modifications or alterations of the present disclosure can be made by those skilled in the art after having read the above teachings of the present disclosure, and these equivalent forms also fall within the scope defined by the claims appended hereto.

The invention claimed is:

1. A nucleic acid molecule encoding a chimeric CD3 fusion protein and a bispecific T cell activating element;

wherein the chimeric CD3 fusion protein comprises one or more polypeptide(s) recognizable by an anti-CD3 antibody (EC), wherein EC is polypeptide from or derived from CD3e; and optionally one or more of the following domains: hinge or linker regions, transmembrane domains (TM), co-stimulatory domains and CD3 signal activation domains; and the bispecific T cell activating element is a fusion protein which comprises one or more tumor antigen recognition region(s) and one or more CD3 antigen-binding antibody fragment(s);

wherein the fusion protein has a structure shown in the following formula I:

L-EC-H-TM-C-CD3ζ (I)

wherein in the formula,

L is absent or a signal peptide sequence;

EC is a polypeptide binding domain recognizable by an anti-CD3 antibody and binds to the anti-CD3 antibody;

H is absent or a linker or a hinge region;

TM is a transmembrane domain;

C is absent or a costimulatory signaling molecule;

CD3ζ is absent or a cytoplasmic signaling sequence derived from CD3ζ;

each "—" is independently a linker peptide or a peptide bond;

wherein the bispecific T cell activating element has a structure shown in the following formula II:

L'-T1-B1-B2-T2 (II)

wherein:

L' is absent or a signal peptide sequence;

T1 is absent or a tag element;

B1 is a tumor antigen recognition region or a CD3 antigen-binding antibody fragment;

B2 is a CD3 antigen-binding antibody fragment or a tumor antigen recognition region; T2 is absent or a tag element;

each "—" is independently a linker peptide or peptide bond.

2. The nucleic acid molecule according to claim 1, wherein EC comprises position 1 to 104 of a CD3e protein, having an amino acid sequence as set forth by SEQ ID NO: 4 and/or a nucleotide sequence as set forth by SEQ ID NO.: 3.

3. The nucleic acid molecule according to claim 1, wherein C when present is a costimulatory signal molecule of a protein selected from the following group: OX40, CD2, CD7, CD27, CD28, CD30, CD40, CD70, CD134, 4-1BB (CD137), PD1, Dap10, CDS, ICAM-1, LFA-1 (CD 11 a/CD 18), ICOS (CD278), NKG2D, GITR, TLR2, or a combination thereof.

4. The nucleic acid molecule according to claim 1, wherein C when present comprises a 4-1BB-derived costimulatory signal molecule having an amino acid sequence as set forth by SEQ ID NO: 10 and/or a nucleotide sequence as set forth by SEQ ID NO: 9, and/or a CD28-derived costimulatory signal molecule having an amino acid sequence as set forth by SEQ ID NO: 62 and/or a nucleotide sequence as set forth by SEQ ID NO: 61.

5. The nucleic acid molecule according to claim 1, wherein CD3ζ when present is a cytoplasmic signaling sequence having an amino acid sequence as set forth by SEQ ID NO: 12 and/or a nucleotide sequence as set forth by SEQ ID NO: 11.

6. The nucleic acid molecule according to claim 1, wherein the construct is co-expressed with polypeptides from or derived from Caspase 9 (iCasp9), CD19, CD20, EGFR, HER2, CD30, CD19, c-Met, Claudin 18.2, or a combination thereof.

7. The nucleic acid molecule according to claim 1, wherein B1 is a tumor antigen recognition region and B2 is a CD3 antigen recognition region.

8. The nucleic acid molecule according to claim 1, wherein the tumor antigen recognition region comprises of receptor or ligand binding domain, an antibody fragment, and/or a T-cell receptor (TCR) sequence.

9. The nucleic acid molecule according to claim 1, wherein the tumor antigen recognition region targets tumor antigen CAIX and/or HER2.

10. The nucleic acid molecule according to claim 1, wherein the tumor antigen recognition region is an antibody fragment, and having an amino acid sequence as set forth by SEQ ID NO: 18 and/or a nucleotide sequence as set forth by SEQ ID NO: 17.

11. The nucleic acid molecule according to claim 1, wherein the tumor antigen recognition region is an antibody fragment, targeting HER2 and having an amino acid sequence as set forth by SEQ ID NO: 66 and/or a nucleotide sequence as set forth by SEQ ID NO: 65.

12. The nucleic acid molecule according to claim 1, wherein the CD3 antigen-binding antibody fragment(s) comprises of a single domain antibody sequence (VHH), a single-chain antibody variable region sequence (scFv), and/or an antigen-binding fragment (Fab) that targets CD3.

13. The nucleic acid molecule according to claim 1, wherein the CD3 antigen-binding antibody fragment is derived from anti-CD3 Ab clones of L2K, UCHT, OKT3, F6A, SP34 etc.

14. The nucleic acid molecule according to claim 1, comprising the sequence as set forth by SEQ ID NO.: 73.

15. The nucleic acid molecule according to claim 1, comprising the sequence as set forth by SEQ ID. NO.: 67.

16. The nucleic acid molecule according to claim 1, wherein the nucleic acid molecule encoding the chimeric CD3 fusion protein and the nucleic acid molecule encoding the bispecific T cell activating element are encoded by separate nucleic acid molecules.

17. The nucleic acid molecule according to claim 16, wherein the nucleic acid molecule encoding the chimeric CD3 fusion protein and the nucleic acid molecule encoding the bispecific T cell activating element are co-expressed in the same immune cell.

18. A vector, wherein the vector comprises the nucleic acid molecule according to claim 1.

19. A genetically engineered immune cell, wherein the immune cell expresses the nucleic acid molecule according to claim 1.

20. The genetically engineered immune cell according to claim 19, wherein the immune cell is T cell.

21. The genetically engineered immune cell according to claim 20, wherein the immune cell is engineered to express the chimeric CD3 fusion protein and the bispecific T cell activating element, whereby the nucleic acid molecule encoding chimeric CD3 fusion protein and the nucleic acid molecule encoding the bispecific T cell activating element are not provided on the same DNA construct.

22. A non-naturally occurring T cell population, comprising the genetically engineered immune cell according to claim 20, wherein the T cells are present in the T cell population at a ratio C1 of 10% or more, based on the total number of T cells in the T cell population.

23. A composition, comprising: (a) the genetically engineered immune cell according to claim 20 and/or a T cell population comprising the genetically engineered immune cell, and (b) a pharmaceutically acceptable carrier, diluent and/or excipient.

24. A method of preventing and/or treating cancer or tumor, comprising administering the genetically engineered immune cell according to claim 20 and/or a T cell population comprising the genetically engineered immune cell to a subject in need thereof.

25. The method according to claim 24, wherein the tumor is selected from the following group: a hematological tumor, a solid tumor, or a combination thereof.

26. The method according to claim 24, wherein the method further comprises the administration of dasatinib.

* * * * *

SEQUENCE LISTING

```
<160> NUMBER OF SEQ ID NOS: 76

<210> SEQ ID NO 1
<211> LENGTH: 66
<212> TYPE: DNA
<213> ORGANISM: Artificial Sequence
<220> FEATURE:
<223> OTHER INFORMATION: GM-CSFRsp

<400> SEQUENCE: 1

atgctgctgc tggtgacctc cctgctgctg tgcgagctgc cccaccccgc tttcctgctg      60

atcccc                                                                 66


<210> SEQ ID NO 2
<211> LENGTH: 22
<212> TYPE: PRT
<213> ORGANISM: Artificial Sequence
<220> FEATURE:
<223> OTHER INFORMATION: GM-CSFRsp

<400> SEQUENCE: 2

Met Leu Leu Leu Val Thr Ser Leu Leu Leu Cys Glu Leu Pro His Pro
1               5                   10                  15

Ala Phe Leu Leu Ile Pro
            20


<210> SEQ ID NO 3
<211> LENGTH: 312
<212> TYPE: DNA
<213> ORGANISM: Artificial Sequence
<220> FEATURE:
<223> OTHER INFORMATION: CD3e ECD

<400> SEQUENCE: 3

gacggcaacg aggagatggg cggcatcacc cagacccccct acaaggtgtc catctccggc      60

accaccgtga tcctgacctg ccctcagtac cccggctccg agatcctgtg gcagcacaac     120

gataagaaca tcggcggaga cgaggacgac aagaacatcg gaagtgacga ggaccacctg     180

agcctgaagg aattcagcga actggagcag agcggctatt acgtctgcta ccccagagga     240

agcaaaccag aggacgccaa cttctatctg tacctgagag ccagagtgtg cgagaactgc     300

atggaaatgg ac                                                         312


<210> SEQ ID NO 4
<211> LENGTH: 104
<212> TYPE: PRT
<213> ORGANISM: Artificial Sequence
<220> FEATURE:
<223> OTHER INFORMATION: CD3e ECD

<400> SEQUENCE: 4

Asp Gly Asn Glu Glu Met Gly Gly Ile Thr Gln Thr Pro Tyr Lys Val
1               5                   10                  15
```

Ser Ile Ser Gly Thr Thr Val Ile Leu Thr Cys Pro Gln Tyr Pro Gly
20 25 30

Ser Glu Ile Leu Trp Gln His Asn Asp Lys Asn Ile Gly Gly Asp Glu
35 40 45

Asp Asp Lys Asn Ile Gly Ser Asp Glu Asp His Leu Ser Leu Lys Glu
50 55 60

Phe Ser Glu Leu Glu Gln Ser Gly Tyr Tyr Val Cys Tyr Pro Arg Gly
65 70 75 80

Ser Lys Pro Glu Asp Ala Asn Phe Tyr Leu Tyr Leu Arg Ala Arg Val
85 90 95

Cys Glu Asn Cys Met Glu Met Asp
100

<210> SEQ ID NO 5
<211> LENGTH: 135
<212> TYPE: DNA
<213> ORGANISM: Artificial Sequence
<220> FEATURE:
<223> OTHER INFORMATION: CD8 Hinge

<400> SEQUENCE: 5
acaaccaccc ccgcccccag acccccaacc cctgctccta ccattgccag ccagccactg 60
tccctgaggc ccgaagcctg cagaccagca gccggcggag ccgtgcacac cagaggactg 120
gacttcgcct gcgac 135

<210> SEQ ID NO 6
<211> LENGTH: 45
<212> TYPE: PRT
<213> ORGANISM: Artificial Sequence
<220> FEATURE:
<223> OTHER INFORMATION: CD8 Hinge

<400> SEQUENCE: 6

Thr Thr Thr Pro Ala Pro Arg Pro Pro Thr Pro Ala Pro Thr Ile Ala
1 5 10 15

Ser Gln Pro Leu Ser Leu Arg Pro Glu Ala Cys Arg Pro Ala Ala Gly
20 25 30

Gly Ala Val His Thr Arg Gly Leu Asp Phe Ala Cys Asp
35 40 45

<210> SEQ ID NO 7
<211> LENGTH: 72
<212> TYPE: DNA
<213> ORGANISM: Artificial Sequence
<220> FEATURE:
<223> OTHER INFORMATION: CD8 TM

<400> SEQUENCE: 7
atctacatct gggcccccct ggccgggacc tgcggagtgc tgctgctgag cctggtgatt 60
actctgtact gt 72

<210> SEQ ID NO 8
<211> LENGTH: 24
<212> TYPE: PRT
<213> ORGANISM: Artificial Sequence
<220> FEATURE:
<223> OTHER INFORMATION: CD8 TM

<400> SEQUENCE: 8

Ile Tyr Ile Trp Ala Pro Leu Ala Gly Thr Cys Gly Val Leu Leu Leu 1 5 10 15

Ser Leu Val Ile Thr Leu Tyr Cys
20

<210> SEQ ID NO 9
<211> LENGTH: 126
<212> TYPE: DNA
<213> ORGANISM: Artificial Sequence
<220> FEATURE:
<223> OTHER INFORMATION: 4-1BB costimulatory domain

<400> SEQUENCE: 9
aagaggggaa gaaagaaact gctgtatatc ttcaagcagc cctttatgag acccgtgcag 60
accacccagg aggaggacgg ctgctcctgt agattccccg aggaggagga gggcggctgc 120
gagctg 126

<210> SEQ ID NO 10
<211> LENGTH: 42
<212> TYPE: PRT
<213> ORGANISM: Artificial Sequence
<220> FEATURE:
<223> OTHER INFORMATION: 4-1BB costimulatory domain

<400> SEQUENCE: 10

Lys Arg Gly Arg Lys Lys Leu Leu Tyr Ile Phe Lys Gln Pro Phe Met
1 5 10 15

Arg Pro Val Gln Thr Thr Gln Glu Glu Asp Gly Cys Ser Cys Arg Phe
20 25 30

Pro Glu Glu Glu Glu Gly Gly Cys Glu Leu
35 40

<210> SEQ ID NO 11
<211> LENGTH: 336
<212> TYPE: DNA
<213> ORGANISM: Artificial Sequence
<220> FEATURE:
<223> OTHER INFORMATION: CD3z

<400> SEQUENCE: 11
agagtgaagt tctccaggag cgccgacgcc cccgcctacc agcagggaca gaaccagctg 60
tacaacgagc tgaacctggg cagaagagag gagtatgacg tgctggacaa gagaagagga 120
agagaccccg agatgggagg aaagccaaga agaaagaacc cccaggaggg cctgtacaat 180
gagctgcaga aggacaagat ggcagaggca tatagcgaga tcggaatgaa gggagagaga 240
agaagaggaa agggacacga cggactgtac cagggcctga gcacagctac aaaggacaca 300
tacgacgcac tgcacatgca ggcactgcca ccaaga 336

<210> SEQ ID NO 12
<211> LENGTH: 112
<212> TYPE: PRT
<213> ORGANISM: Artificial Sequence
<220> FEATURE:
<223> OTHER INFORMATION: CD3z

<400> SEQUENCE: 12

Arg Val Lys Phe Ser Arg Ser Ala Asp Ala Pro Ala Tyr Gln Gln Gly
1 5 10 15

Gln Asn Gln Leu Tyr Asn Glu Leu Asn Leu Gly Arg Arg Glu Glu Tyr
20 25 30

Asp Val Leu Asp Lys Arg Arg Gly Arg Asp Pro Glu Met Gly Gly Lys

```
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110


<210> SEQ ID NO 13
<211> LENGTH: 24
<212> TYPE: DNA
<213> ORGANISM: Artificial Sequence
<220> FEATURE:
<223> OTHER INFORMATION: FLAG

<400> SEQUENCE: 13

gactacaagg acgatgacga caag                                             24


<210> SEQ ID NO 14
<211> LENGTH: 8
<212> TYPE: PRT
<213> ORGANISM: Artificial Sequence
<220> FEATURE:
<223> OTHER INFORMATION: FLAG

<400> SEQUENCE: 14

Asp Tyr Lys Asp Asp Asp Asp Lys
1               5


<210> SEQ ID NO 15
<211> LENGTH: 1074
<212> TYPE: DNA
<213> ORGANISM: Artificial Sequence
<220> FEATURE:
<223> OTHER INFORMATION: CD3e-BBzeta

<400> SEQUENCE: 15

atgctgctgc tggtgacctc cctgctgctg tgcgagctgc cccaccccgc tttcctgctg      60

atccccgacg gcaacgagga gatgggcggc atcacccaga ccccctacaa ggtgtccatc     120

tccggcacca ccgtgatcct gacctgccct cagtaccccg gctccgagat cctgtggcag     180

cacaacgata agaacatcgg cggagacgag gacgacaaga acatcggaag tgacgaggac     240

cacctgagcc tgaaggaatt cagcgaactg gagcagagcg gctattacgt ctgctacccc     300

agaggaagca aaccagagga cgccaacttc tatctgtacc tgagagccag agtgtgcgag     360

aactgcatgg aaatggacac aaccaccccc gcccccagac ccccaacccc tgctcctacc     420

attgccagcc agccactgtc cctgaggccc gaagcctgca gaccagcagc cggcggagcc     480

gtgcacacca gaggactgga cttcgcctgc gacatctaca tctgggcccc cctggccggg     540

acctgcggag tgctgctgct gagcctggtg attactctgt actgtaagag gggaagaaag     600

aaactgctgt atatcttcaa gcagcccttt atgagacccg tgcagaccac ccaggaggag     660

gacggctgct cctgtagatt ccccgaggag gaggagggcg gctgcgagct gagagtgaag     720

ttctccagga gcgccgacgc ccccgcctac cagcagggac agaaccagct gtacaacgag     780

ctgaacctgg gcagaagaga ggagtatgac gtgctggaca agagaagagg aagagacccc     840

gagatgggag gaaagccaag aagaaagaac ccccaggagg gcctgtacaa tgagctgcag     900
```

aaggacaaga tggcagaggc atatagcgag atcggaatga agggagagag aagaagagga 960
aagggacacg acggactgta ccagggcctg agcacagcta caaaggacac atacgacgca 1020
ctgcacatgc aggcactgcc accaagagac tacaaggacg atgacgacaa gtaa 1074

<210> SEQ ID NO 16
<211> LENGTH: 357
<212> TYPE: PRT
<213> ORGANISM: Artificial Sequence
<220> FEATURE:
<223> OTHER INFORMATION: CD3e-BBzeta

<400> SEQUENCE: 16

Met Leu Leu Leu Val Thr Ser Leu Leu Leu Cys Glu Leu Pro His Pro
1 5 10 15

Ala Phe Leu Leu Ile Pro Asp Gly Asn Glu Glu Met Gly Gly Ile Thr
20 25 30

Gln Thr Pro Tyr Lys Val Ser Ile Ser Gly Thr Thr Val Ile Leu Thr
35 40 45

Cys Pro Gln Tyr Pro Gly Ser Glu Ile Leu Trp Gln His Asn Asp Lys
50 55 60

Asn Ile Gly Gly Asp Glu Asp Asp Lys Asn Ile Gly Ser Asp Glu Asp
65 70 75 80

His Leu Ser Leu Lys Glu Phe Ser Glu Leu Glu Gln Ser Gly Tyr Tyr
85 90 95

Val Cys Tyr Pro Arg Gly Ser Lys Pro Glu Asp Ala Asn Phe Tyr Leu
100 105 110

Tyr Leu Arg Ala Arg Val Cys Glu Asn Cys Met Glu Met Asp Thr Thr
115 120 125

Thr Pro Ala Pro Arg Pro Pro Thr Pro Ala Pro Thr Ile Ala Ser Gln
130 135 140

Pro Leu Ser Leu Arg Pro Glu Ala Cys Arg Pro Ala Ala Gly Gly Ala
145 150 155 160

Val His Thr Arg Gly Leu Asp Phe Ala Cys Asp Ile Tyr Ile Trp Ala
165 170 175

Pro Leu Ala Gly Thr Cys Gly Val Leu Leu Leu Ser Leu Val Ile Thr
180 185 190

Leu Tyr Cys Lys Arg Gly Arg Lys Lys Leu Leu Tyr Ile Phe Lys Gln
195 200 205

Pro Phe Met Arg Pro Val Gln Thr Thr Gln Glu Glu Asp Gly Cys Ser
210 215 220

Cys Arg Phe Pro Glu Glu Glu Glu Gly Gly Cys Glu Leu Arg Val Lys
225 230 235 240

Phe Ser Arg Ser Ala Asp Ala Pro Ala Tyr Gln Gln Gly Gln Asn Gln
245 250 255

Leu Tyr Asn Glu Leu Asn Leu Gly Arg Arg Glu Glu Tyr Asp Val Leu
260 265 270

Asp Lys Arg Arg Gly Arg Asp Pro Glu Met Gly Gly Lys Pro Arg Arg
275 280 285

Lys Asn Pro Gln Glu Gly Leu Tyr Asn Glu Leu Gln Lys Asp Lys Met
290 295 300

Ala Glu Ala Tyr Ser Glu Ile Gly Met Lys Gly Glu Arg Arg Arg Gly
305 310 315 320

Lys Gly His Asp Gly Leu Tyr Gln Gly Leu Ser Thr Ala Thr Lys Asp
325 330 335

```
Thr Tyr Asp Ala Leu His Met Gln Ala Leu Pro Pro Arg Asp Tyr Lys
            340                 345                 350

Asp Asp Asp Asp Lys
        355


<210> SEQ ID NO 17
<211> LENGTH: 351
<212> TYPE: DNA
<213> ORGANISM: Artificial Sequence
<220> FEATURE:
<223> OTHER INFORMATION: CAIX VHH

<400> SEQUENCE: 17

caggtgcagc tgcaggagtc tggcggcggc ctggtgcagc ctggaggatc tctgagactg      60

agctgcgccg cctccggcaa cagcgctaac atcttttcct ttgcttccgt ggcctggtat     120

aggcaggccc cagggaagca gagagagctg gtggccgtca ttacatccgc cggcggcaca     180

aagtactccg actctgtgaa gggaagattc accattagcc gggacaatgc caagaacacc     240

attctgctgc agatgaactc actgaaacct gaggataccg ccgtgtatta ttgtaacgtg     300

gactacctgc aggactactg gggcagggc acccaggtga cagtgagcag c              351


<210> SEQ ID NO 18
<211> LENGTH: 117
<212> TYPE: PRT
<213> ORGANISM: Artificial Sequence
<220> FEATURE:
<223> OTHER INFORMATION: CAIX VHH

<400> SEQUENCE: 18

Gln Val Gln Leu Gln Glu Ser Gly Gly Gly Leu Val Gln Pro Gly Gly
1               5                   10                  15

Ser Leu Arg Leu Ser Cys Ala Ala Ser Gly Asn Ser Ala Asn Ile Phe
            20                  25                  30

Ser Phe Ala Ser Val Ala Trp Tyr Arg Gln Ala Pro Gly Lys Gln Arg
        35                  40                  45

Glu Leu Val Ala Val Ile Thr Ser Ala Gly Gly Thr Lys Tyr Ser Asp
    50                  55                  60

Ser Val Lys Gly Arg Phe Thr Ile Ser Arg Asp Asn Ala Lys Asn Thr
65                  70                  75                  80

Ile Leu Leu Gln Met Asn Ser Leu Lys Pro Glu Asp Thr Ala Val Tyr
                85                  90                  95

Tyr Cys Asn Val Asp Tyr Leu Gln Asp Tyr Trp Gly Gln Gly Thr Gln
            100                 105                 110

Val Thr Val Ser Ser
        115


<210> SEQ ID NO 19
<211> LENGTH: 729
<212> TYPE: DNA
<213> ORGANISM: Artificial Sequence
<220> FEATURE:
<223> OTHER INFORMATION: L2K scFv

<400> SEQUENCE: 19

gatatcaagc tgcagcagag cggagccgag ctggccaggc ctggagctag cgtgaagatg      60

agctgcaaaa ccagcggcta cacattcacc agatacacca tgcattgggt gaagcagaga     120

cccggacagg gactggagtg gattggatac attaacccca gtcgaggcta caccaactac     180

aaccagaagt tcaaagacaa agccaccctg accaccgaca aaagcagcag caccgcatat     240
```

atgcagctga gctctctgac cagcgaggac agcgccgtgt actactgcgc cagatactac 300
gacgaccact actgcctgga ctactggggc cagggaacca ccctgacagt gtctagcgtg 360
gagggcggat ctggcggctc aggcggaagc ggagggagcg gaggagtgga cgatatccag 420
ctgacccaga gtcccgccat catgagtgca agtcccggcg aaaaagtgac catgacctgt 480
agagcttctt ctagtgtgag ttatatgaac tggtaccagc agaagagcgg gaccagcccc 540
aaaagatgga tctacgacac cagcaaggtg gccagcggcg tgccctaccg gttcagcgga 600
tctggcagcg gaacctcata cagcctgact atcagcagca tggaagcaga agacgccgca 660
acctactact gccagcagtg gagctctaac ccactgacct tcggcgctgg caccaagctg 720
gagctgaag 729

<210> SEQ ID NO 20
<211> LENGTH: 243
<212> TYPE: PRT
<213> ORGANISM: Artificial Sequence
<220> FEATURE:
<223> OTHER INFORMATION: L2K scFv

<400> SEQUENCE: 20

Asp Ile Lys Leu Gln Gln Ser Gly Ala Glu Leu Ala Arg Pro Gly Ala
1 5 10 15

Ser Val Lys Met Ser Cys Lys Thr Ser Gly Tyr Thr Phe Thr Arg Tyr
20 25 30

Thr Met His Trp Val Lys Gln Arg Pro Gly Gln Gly Leu Glu Trp Ile
35 40 45

Gly Tyr Ile Asn Pro Ser Arg Gly Tyr Thr Asn Tyr Asn Gln Lys Phe
50 55 60

Lys Asp Lys Ala Thr Leu Thr Thr Asp Lys Ser Ser Ser Thr Ala Tyr
65 70 75 80

Met Gln Leu Ser Ser Leu Thr Ser Glu Asp Ser Ala Val Tyr Tyr Cys
85 90 95

Ala Arg Tyr Tyr Asp Asp His Tyr Cys Leu Asp Tyr Trp Gly Gln Gly
100 105 110

Thr Thr Leu Thr Val Ser Ser Val Glu Gly Gly Ser Gly Gly Ser Gly
115 120 125

Gly Ser Gly Gly Ser Gly Gly Val Asp Asp Ile Gln Leu Thr Gln Ser
130 135 140

Pro Ala Ile Met Ser Ala Ser Pro Gly Glu Lys Val Thr Met Thr Cys
145 150 155 160

Arg Ala Ser Ser Ser Val Ser Tyr Met Asn Trp Tyr Gln Gln Lys Ser
165 170 175

Gly Thr Ser Pro Lys Arg Trp Ile Tyr Asp Thr Ser Lys Val Ala Ser
180 185 190

Gly Val Pro Tyr Arg Phe Ser Gly Ser Gly Ser Gly Thr Ser Tyr Ser
195 200 205

Leu Thr Ile Ser Ser Met Glu Ala Glu Asp Ala Ala Thr Tyr Tyr Cys
210 215 220

Gln Gln Trp Ser Ser Asn Pro Leu Thr Phe Gly Ala Gly Thr Lys Leu
225 230 235 240

Glu Leu Lys

<210> SEQ ID NO 21
<211> LENGTH: 1164

<212> TYPE: DNA
<213> ORGANISM: Artificial Sequence
<220> FEATURE:
<223> OTHER INFORMATION: 1st-CAIX-BiTA

<400> SEQUENCE: 21

```
atgctgctgc tggtgacctc cctgctgctg tgcgagctgc cccaccccgc tttcctgctg     60

atcccccagg tgcagctgca ggagtctggc ggcggcctgg tgcagcctgg aggatctctg    120

agactgagct gcgccgcctc cggcaacagc gctaacatct tttcctttgc ttccgtggcc    180

tggtataggc aggccccagg gaagcagaga gagctggtgg ccgtcattac atccgccggc    240

ggcacaaagt actccgactc tgtgaaggga agattcacca ttagccggga caatgccaag    300

aacaccattc tgctgcagat gaactcactg aaacctgagg ataccgccgt gtattattgt    360

aacgtggact acctgcagga ctactggggg cagggcaccc aggtgacagt gagcagcggc    420

ggcggcggaa gcgatatcaa gctgcagcag agcggagccg agctggccag gcctggagct    480

agcgtgaaga tgagctgcaa aaccagcggc tacacattca ccagatacac catgcattgg    540

gtgaagcaga gacccggaca gggactggag tggattggat acattaaccc cagtcgaggc    600

tacaccaact acaaccagaa gttcaaagac aaagccaccc tgaccaccga caaaagcagc    660

agcaccgcat atatgcagct gagctctctg accagcgagg acagcgccgt gtactactgc    720

gccagatact acgacgacca ctactgcctg gactactggg gccagggaac caccctgaca    780

gtgtctagcg tggagggcgg atctggcggc tcaggcggaa gcggagggag cggaggagtg    840

gacgatatcc agctgaccca gagtcccgcc atcatgagtg caagtcccgg cgaaaaagtg    900

accatgacct gtagagcttc ttctagtgtg agttatatga actggtacca gcagaagagc    960

gggaccagcc ccaaaagatg gatctacgac accagcaagg tggccagcgg cgtgccctac   1020

cggttcagcg gatctggcag cggaacctca tacagcctga ctatcagcag catggaagca   1080

gaagacgccg caacctacta ctgccagcag tggagctcta acccactgac cttcggcgct   1140

ggcaccaagc tggagctgaa gtaa                                          1164
```

<210> SEQ ID NO 22
<211> LENGTH: 387
<212> TYPE: PRT
<213> ORGANISM: Artificial Sequence
<220> FEATURE:
<223> OTHER INFORMATION: 1st-CAIX-BiTA

<400> SEQUENCE: 22

```
Met Leu Leu Leu Val Thr Ser Leu Leu Leu Cys Glu Leu Pro His Pro
1               5                   10                  15

Ala Phe Leu Leu Ile Pro Gln Val Gln Leu Gln Glu Ser Gly Gly Gly
            20                  25                  30

Leu Val Gln Pro Gly Gly Ser Leu Arg Leu Ser Cys Ala Ala Ser Gly
        35                  40                  45

Asn Ser Ala Asn Ile Phe Ser Phe Ala Ser Val Ala Trp Tyr Arg Gln
    50                  55                  60

Ala Pro Gly Lys Gln Arg Glu Leu Val Ala Val Ile Thr Ser Ala Gly
65                  70                  75                  80

Gly Thr Lys Tyr Ser Asp Ser Val Lys Gly Arg Phe Thr Ile Ser Arg
                85                  90                  95

Asp Asn Ala Lys Asn Thr Ile Leu Leu Gln Met Asn Ser Leu Lys Pro
            100                 105                 110

Glu Asp Thr Ala Val Tyr Tyr Cys Asn Val Asp Tyr Leu Gln Asp Tyr
```

```
        115                 120                 125

Trp Gly Gln Gly Thr Gln Val Thr Val Ser Ser Gly Gly Gly Gly Ser
    130                 135                 140

Asp Ile Lys Leu Gln Gln Ser Gly Ala Glu Leu Ala Arg Pro Gly Ala
145                 150                 155                 160

Ser Val Lys Met Ser Cys Lys Thr Ser Gly Tyr Thr Phe Thr Arg Tyr
                165                 170                 175

Thr Met His Trp Val Lys Gln Arg Pro Gly Gln Gly Leu Glu Trp Ile
            180                 185                 190

Gly Tyr Ile Asn Pro Ser Arg Gly Tyr Thr Asn Tyr Asn Gln Lys Phe
        195                 200                 205

Lys Asp Lys Ala Thr Leu Thr Thr Asp Lys Ser Ser Ser Thr Ala Tyr
    210                 215                 220

Met Gln Leu Ser Ser Leu Thr Ser Glu Asp Ser Ala Val Tyr Tyr Cys
225                 230                 235                 240

Ala Arg Tyr Tyr Asp Asp His Tyr Cys Leu Asp Tyr Trp Gly Gln Gly
                245                 250                 255

Thr Thr Leu Thr Val Ser Ser Val Glu Gly Gly Ser Gly Gly Ser Gly
            260                 265                 270

Gly Ser Gly Gly Ser Gly Gly Val Asp Asp Ile Gln Leu Thr Gln Ser
        275                 280                 285

Pro Ala Ile Met Ser Ala Ser Pro Gly Glu Lys Val Thr Met Thr Cys
    290                 295                 300

Arg Ala Ser Ser Ser Val Ser Tyr Met Asn Trp Tyr Gln Gln Lys Ser
305                 310                 315                 320

Gly Thr Ser Pro Lys Arg Trp Ile Tyr Asp Thr Ser Lys Val Ala Ser
                325                 330                 335

Gly Val Pro Tyr Arg Phe Ser Gly Ser Gly Ser Gly Thr Ser Tyr Ser
            340                 345                 350

Leu Thr Ile Ser Ser Met Glu Ala Glu Asp Ala Ala Thr Tyr Tyr Cys
        355                 360                 365

Gln Gln Trp Ser Ser Asn Pro Leu Thr Phe Gly Ala Gly Thr Lys Leu
    370                 375                 380

Glu Leu Lys
385
```

<210> SEQ ID NO 23
<211> LENGTH: 54
<212> TYPE: DNA
<213> ORGANISM: Artificial Sequence
<220> FEATURE:
<223> OTHER INFORMATION: T2A

<400> SEQUENCE: 23

```
gagggcagag gaagcctgct gacatgcgga gacgtggagg agaacccagg accc           54
```

<210> SEQ ID NO 24
<211> LENGTH: 18
<212> TYPE: PRT
<213> ORGANISM: Artificial Sequence
<220> FEATURE:
<223> OTHER INFORMATION: T2A

<400> SEQUENCE: 24

```
Glu Gly Arg Gly Ser Leu Leu Thr Cys Gly Asp Val Glu Glu Asn Pro
1               5                   10                  15

Gly Pro
```

<210> SEQ ID NO 25
<211> LENGTH: 2298
<212> TYPE: DNA
<213> ORGANISM: Artificial Sequence
<220> FEATURE:
<223> OTHER INFORMATION: 1st-CAIX-CAB

<400> SEQUENCE: 25
atgctgctgc tggtgacctc cctgctgctg tgcgagctgc cccaccccgc tttcctgctg 60
atccccgacg gcaacgagga gatgggcggc atcacccaga ccccctacaa ggtgtccatc 120
tccggcacca ccgtgatcct gacctgccct cagtaccccg gctccgagat cctgtggcag 180
cacaacgata agaacatcgg cggagacgag gacgacaaga acatcggaag tgacgaggac 240
cacctgagcc tgaaggaatt cagcgaactg gagcagagcg gctattacgt ctgctacccc 300
agaggaagca aaccagagga cgccaacttc tatctgtacc tgagagccag agtgtgcgag 360
aactgcatgg aaatggacac aaccaccccc gcccccagac cccccaacccc tgctcctacc 420 attgccagcc agccactgtc cctgaggccc gaagcctgca gaccagcagc cggcggagcc 480
gtgcacacca gaggactgga cttcgcctgc gacatctaca tctgggcccc cctggccggg 540
acctgcggag tgctgctgct gagcctggtg attactctgt actgtaagag gggaagaaag 600
aaactgctgt atatcttcaa gcagcccttt atgagacccg tgcagaccac ccaggaggag 660
gacggctgct cctgtagatt ccccgaggag gaggagggcg gctgcgagct gagagtgaag 720
ttctccagga gcgccgacgc ccccgcctac cagcagggac agaaccagct gtacaacgag 780
ctgaacctgg gcagaagaga ggagtatgac gtgctggaca agagaagagg aagagacccc 840
gagatgggag gaaagccaag aagaaagaac ccccaggagg gcctgtacaa tgagctgcag 900
aaggacaaga tggcagaggc atatagcgag atcggaatga agggagagag aagaagagga 960
aagggacacg acggactgta ccagggcctg agcacagcta caaaggacac atacgacgca 1020
ctgcacatgc aggcactgcc accaagagac tacaaggacg atgacgacaa gggaagcgga 1080
gagggcagag gaagcctgct gacatgcgga gacgtggagg agaacccagg acccatgctg 1140
ctgctggtga cctccctgct gctgtgcgag ctgccccacc ccgctttcct gctgatcccc 1200
caggtgcagc tgcaggagtc tggcggcggc ctggtgcagc ctggaggatc tctgagactg 1260
agctgcgccg cctccggcaa cagcgctaac atcttttcct ttgcttccgt ggcctggtat 1320
aggcaggccc cagggaagca gagagagctg gtggccgtca ttacatccgc cggcggcaca 1380
aagtactccg actctgtgaa gggaagattc accattagcc gggacaatgc caagaacacc 1440
attctgctgc agatgaactc actgaaacct gaggataccg ccgtgtatta ttgtaacgtg 1500
gactacctgc aggactactg gggcagggc acccaggtga cagtgagcag cggcggcggc 1560
ggaagcgata tcaagctgca gcagagcgga gccgagctgg ccaggcctgg agctagcgtg 1620
aagatgagct gcaaaaccag cggctacaca ttcaccagat acaccatgca ttgggtgaag 1680
cagagacccg gacagggact ggagtggatt ggatacatta accccagtcg aggctacacc 1740
aactacaacc agaagttcaa agacaaagcc accctgacca ccgacaaaag cagcagcacc 1800
gcatatatgc agctgagctc tctgaccagc gaggacagcg ccgtgtacta ctgcgccaga 1860
tactacgacg accactactg cctggactac tggggccagg gaaccaccct gacagtgtct 1920
agcgtggagg gcggatctgg cggctcaggc ggaagcggag ggagcggagg agtggacgat 1980
atccagctga cccagagtcc cgccatcatg agtgcaagtc ccggcgaaaa agtgaccatg 2040
acctgtagag cttcttctag tgtgagttat atgaactggt accagcagaa gagcgggacc 2100
agccccaaaa gatggatcta cgacaccagc aaggtggcca gcggcgtgcc ctaccggttc 2160
agcggatctg gcagcggaac ctcatacagc ctgactatca gcagcatgga agcagaagac 2220
gccgcaacct actactgcca gcagtggagc tctaacccac tgaccttcgg cgctggcacc 2280
aagctggagc tgaagtaa 2298

<210> SEQ ID NO 26
<211> LENGTH: 765
<212> TYPE: PRT
<213> ORGANISM: Artificial Sequence
<220> FEATURE:
<223> OTHER INFORMATION: 1st-CAIX-CAB

<400> SEQUENCE: 26

Met Leu Leu Leu Val Thr Ser Leu Leu Leu Cys Glu Leu Pro His Pro
1 5 10 15

Ala Phe Leu Leu Ile Pro Asp Gly Asn Glu Glu Met Gly Gly Ile Thr
20 25 30

Gln Thr Pro Tyr Lys Val Ser Ile Ser Gly Thr Thr Val Ile Leu Thr
35 40 45

Cys Pro Gln Tyr Pro Gly Ser Glu Ile Leu Trp Gln His Asn Asp Lys
50 55 60

Asn Ile Gly Gly Asp Glu Asp Asp Lys Asn Ile Gly Ser Asp Glu Asp
65 70 75 80

His Leu Ser Leu Lys Glu Phe Ser Glu Leu Glu Gln Ser Gly Tyr Tyr
85 90 95

Val Cys Tyr Pro Arg Gly Ser Lys Pro Glu Asp Ala Asn Phe Tyr Leu
100 105 110

Tyr Leu Arg Ala Arg Val Cys Glu Asn Cys Met Glu Met Asp Thr Thr
115 120 125

Thr Pro Ala Pro Arg Pro Pro Thr Pro Ala Pro Thr Ile Ala Ser Gln
130 135 140

Pro Leu Ser Leu Arg Pro Glu Ala Cys Arg Pro Ala Ala Gly Gly Ala
145 150 155 160

Val His Thr Arg Gly Leu Asp Phe Ala Cys Asp Ile Tyr Ile Trp Ala
165 170 175

Pro Leu Ala Gly Thr Cys Gly Val Leu Leu Leu Ser Leu Val Ile Thr
180 185 190

Leu Tyr Cys Lys Arg Gly Arg Lys Lys Leu Leu Tyr Ile Phe Lys Gln
195 200 205

Pro Phe Met Arg Pro Val Gln Thr Thr Gln Glu Glu Asp Gly Cys Ser
210 215 220

Cys Arg Phe Pro Glu Glu Glu Gly Gly Cys Glu Leu Arg Val Lys
225 230 235 240

Phe Ser Arg Ser Ala Asp Ala Pro Ala Tyr Gln Gln Gly Gln Asn Gln
245 250 255

Leu Tyr Asn Glu Leu Asn Leu Gly Arg Arg Glu Glu Tyr Asp Val Leu
260 265 270

Asp Lys Arg Arg Gly Arg Asp Pro Glu Met Gly Gly Lys Pro Arg Arg
275 280 285

Lys Asn Pro Gln Glu Gly Leu Tyr Asn Glu Leu Gln Lys Asp Lys Met
290 295 300

Ala Glu Ala Tyr Ser Glu Ile Gly Met Lys Gly Glu Arg Arg Arg Gly
305 310 315 320

```
Lys Gly His Asp Gly Leu Tyr Gln Gly Leu Ser Thr Ala Thr Lys Asp
                325                 330                 335

Thr Tyr Asp Ala Leu His Met Gln Ala Leu Pro Pro Arg Asp Tyr Lys
            340                 345                 350

Asp Asp Asp Asp Lys Gly Ser Gly Glu Gly Arg Gly Ser Leu Leu Thr
        355                 360                 365

Cys Gly Asp Val Glu Glu Asn Pro Gly Pro Met Leu Leu Leu Val Thr
    370                 375                 380

Ser Leu Leu Leu Cys Glu Leu Pro His Pro Ala Phe Leu Leu Ile Pro
385                 390                 395                 400

Gln Val Gln Leu Gln Glu Ser Gly Gly Gly Leu Val Gln Pro Gly Gly
                405                 410                 415

Ser Leu Arg Leu Ser Cys Ala Ala Ser Gly Asn Ser Ala Asn Ile Phe
            420                 425                 430

Ser Phe Ala Ser Val Ala Trp Tyr Arg Gln Ala Pro Gly Lys Gln Arg
        435                 440                 445

Glu Leu Val Ala Val Ile Thr Ser Ala Gly Gly Thr Lys Tyr Ser Asp
    450                 455                 460

Ser Val Lys Gly Arg Phe Thr Ile Ser Arg Asp Asn Ala Lys Asn Thr
465                 470                 475                 480

Ile Leu Leu Gln Met Asn Ser Leu Lys Pro Glu Asp Thr Ala Val Tyr
                485                 490                 495

Tyr Cys Asn Val Asp Tyr Leu Gln Asp Tyr Trp Gly Gln Gly Thr Gln
            500                 505                 510

Val Thr Val Ser Ser Gly Gly Gly Gly Ser Asp Ile Lys Leu Gln Gln
        515                 520                 525

Ser Gly Ala Glu Leu Ala Arg Pro Gly Ala Ser Val Lys Met Ser Cys
    530                 535                 540

Lys Thr Ser Gly Tyr Thr Phe Thr Arg Tyr Thr Met His Trp Val Lys
545                 550                 555                 560

Gln Arg Pro Gly Gln Gly Leu Glu Trp Ile Gly Tyr Ile Asn Pro Ser
                565                 570                 575

Arg Gly Tyr Thr Asn Tyr Asn Gln Lys Phe Lys Asp Lys Ala Thr Leu
            580                 585                 590

Thr Thr Asp Lys Ser Ser Ser Thr Ala Tyr Met Gln Leu Ser Ser Leu
        595                 600                 605

Thr Ser Glu Asp Ser Ala Val Tyr Tyr Cys Ala Arg Tyr Tyr Asp Asp
    610                 615                 620

His Tyr Cys Leu Asp Tyr Trp Gly Gln Gly Thr Thr Leu Thr Val Ser
625                 630                 635                 640

Ser Val Glu Gly Gly Ser Gly Gly Ser Gly Gly Ser Gly Gly Ser Gly
                645                 650                 655

Gly Val Asp Asp Ile Gln Leu Thr Gln Ser Pro Ala Ile Met Ser Ala
            660                 665                 670

Ser Pro Gly Glu Lys Val Thr Met Thr Cys Arg Ala Ser Ser Ser Val
        675                 680                 685

Ser Tyr Met Asn Trp Tyr Gln Gln Lys Ser Gly Thr Ser Pro Lys Arg
    690                 695                 700

Trp Ile Tyr Asp Thr Ser Lys Val Ala Ser Gly Val Pro Tyr Arg Phe
705                 710                 715                 720

Ser Gly Ser Gly Ser Gly Thr Ser Tyr Ser Leu Thr Ile Ser Ser Met
                725                 730                 735
```

Glu Ala Glu Asp Ala Ala Thr Tyr Tyr Cys Gln Gln Trp Ser Ser Asn
740 745 750

Pro Leu Thr Phe Gly Ala Gly Thr Lys Leu Glu Leu Lys
755 760 765

<210> SEQ ID NO 27
<211> LENGTH: 45
<212> TYPE: DNA
<213> ORGANISM: Artificial Sequence
<220> FEATURE:
<223> OTHER INFORMATION: Linker

<400> SEQUENCE: 27
ggcggcggcg gaagcggagg aggaggatct ggcggcggag gaagc 45

<210> SEQ ID NO 28
<211> LENGTH: 15
<212> TYPE: PRT
<213> ORGANISM: Artificial Sequence
<220> FEATURE:
<223> OTHER INFORMATION: Linker

<400> SEQUENCE: 28

Gly Gly Gly Gly Ser Gly Gly Gly Gly Ser Gly Gly Gly Gly Ser
1 5 10 15

<210> SEQ ID NO 29
<211> LENGTH: 555
<212> TYPE: DNA
<213> ORGANISM: Artificial Sequence
<220> FEATURE:
<223> OTHER INFORMATION: CD3e

<400> SEQUENCE: 29
gatggaaacg aggagatggg gggaattaca cagacacctt acaaggtgag tatcagcggc 60
accaccgtga tcctgacatg ccctcagtat ccaggaagcg agatcctgtg gcagcacaac 120
gacaaaaaca tcggcgggga cgaggacgac aaaaacattg gcagcgacga ggaccacctg 180
agcctgaagg aattcagcga actggagcag agcggatact acgtgtgcta ccccagagga 240
agcaagcccg aggacgccaa cttctacctg tacctgagag ccagagtctg cgagaactgt 300
atggagatgg acgtgatgag cgtggccaca attgtgatcg tggacatctg catcaccggc 360
ggactgctgc tgctggtcta ctactggagc aaaaacagaa aagccaaggc caagcccgtg 420
acaagaggag ccggcgccgg aggaagacag agaggccaga acaaggagcg gccccccccc 480
gtgcctaacc ctgattacga gcccatcaga aagggccaga gagacctgta cagcggcctg 540
aaccagagaa gaatc 555

<210> SEQ ID NO 30
<211> LENGTH: 185
<212> TYPE: PRT
<213> ORGANISM: Artificial Sequence
<220> FEATURE:
<223> OTHER INFORMATION: CD3e

<400> SEQUENCE: 30

Asp Gly Asn Glu Glu Met Gly Gly Ile Thr Gln Thr Pro Tyr Lys Val
1 5 10 15

Ser Ile Ser Gly Thr Thr Val Ile Leu Thr Cys Pro Gln Tyr Pro Gly
20 25 30

Ser Glu Ile Leu Trp Gln His Asn Asp Lys Asn Ile Gly Gly Asp Glu
35 40 45

```
Asp Asp Lys Asn Ile Gly Ser Asp Glu Asp His Leu Ser Leu Lys Glu
    50                  55                  60

Phe Ser Glu Leu Glu Gln Ser Gly Tyr Tyr Val Cys Tyr Pro Arg Gly
65                  70                  75                  80

Ser Lys Pro Glu Asp Ala Asn Phe Tyr Leu Tyr Leu Arg Ala Arg Val
                85                  90                  95

Cys Glu Asn Cys Met Glu Met Asp Val Met Ser Val Ala Thr Ile Val
            100                 105                 110

Ile Val Asp Ile Cys Ile Thr Gly Gly Leu Leu Leu Leu Val Tyr Tyr
        115                 120                 125

Trp Ser Lys Asn Arg Lys Ala Lys Ala Lys Pro Val Thr Arg Gly Ala
    130                 135                 140

Gly Ala Gly Gly Arg Gln Arg Gly Gln Asn Lys Glu Arg Pro Pro Pro
145                 150                 155                 160

Val Pro Asn Pro Asp Tyr Glu Pro Ile Arg Lys Gly Gln Arg Asp Leu
                165                 170                 175

Tyr Ser Gly Leu Asn Gln Arg Arg Ile
            180                 185
```

<210> SEQ ID NO 31
<211> LENGTH: 1020
<212> TYPE: DNA
<213> ORGANISM: Artificial Sequence
<220> FEATURE:
<223> OTHER INFORMATION: CAIX-TRuC

<400> SEQUENCE: 31

```
atgctgctgc tggtgacctc cctgctgctg tgcgagctgc cccacccgc tttcctgctg      60

atcccccagg tgcagctgca ggagtctggc ggcggcctgg tgcagcctgg aggatctctg    120

agactgagct gcgccgcctc cggcaacagc gctaacatct tttcctttgc ttccgtggcc    180

tggtataggc aggccccagg gaagcagaga gagctggtgg ccgtcattac atccgccggc    240

ggcacaaagt actccgactc tgtgaaggga agattcacca ttagccggga caatgccaag    300

aacaccattc tgctgcagat gaactcactg aaacctgagg ataccgccgt gtattattgt    360

aacgtggact acctgcagga ctactggggg cagggcaccc aggtgacagt gagcagcggc    420

ggcggcggaa gcggaggagg aggatctggc ggcggaggaa gcgatggaaa cgaggagatg    480

gggggaatta cacagacacc ttacaaggtg agtatcagcg gcaccaccgt gatcctgaca    540

tgccctcagt atccaggaag cgagatcctg tggcagcaca acgacaaaaa catcggcggg    600

gacgaggacg acaaaaacat tggcagcgac gaggaccacc tgagcctgaa ggaattcagc    660

gaactggagc agagcggata ctacgtgtgc taccccagag gaagcaagcc cgaggacgcc    720

aacttctacc tgtacctgag agccagagtc tgcgagaact gtatggagat ggacgtgatg    780

agcgtggcca caattgtgat cgtggacatc tgcatcaccg gcggactgct gctgctggtc    840

tactactgga gcaaaaacag aaaagccaag gccaagcccg tgacaagagg agccggcgcc    900

ggaggaagac agagaggcca gaacaaggag cggccccccc ccgtgcctaa ccctgattac    960

gagcccatca gaaagggcca gagagacctg tacagcggcc tgaaccagag aagaatctaa   1020
```

<210> SEQ ID NO 32
<211> LENGTH: 339
<212> TYPE: PRT
<213> ORGANISM: Artificial Sequence
<220> FEATURE:
<223> OTHER INFORMATION: CAIX-TRuC

<400> SEQUENCE: 32

```
Met Leu Leu Leu Val Thr Ser Leu Leu Leu Cys Glu Leu Pro His Pro
1               5                   10                  15

Ala Phe Leu Leu Ile Pro Gln Val Gln Leu Gln Glu Ser Gly Gly Gly
            20                  25                  30

Leu Val Gln Pro Gly Gly Ser Leu Arg Leu Ser Cys Ala Ala Ser Gly
        35                  40                  45

Asn Ser Ala Asn Ile Phe Ser Phe Ala Ser Val Ala Trp Tyr Arg Gln
    50                  55                  60

Ala Pro Gly Lys Gln Arg Glu Leu Val Ala Val Ile Thr Ser Ala Gly
65                  70                  75                  80

Gly Thr Lys Tyr Ser Asp Ser Val Lys Gly Arg Phe Thr Ile Ser Arg
                85                  90                  95

Asp Asn Ala Lys Asn Thr Ile Leu Leu Gln Met Asn Ser Leu Lys Pro
            100                 105                 110

Glu Asp Thr Ala Val Tyr Tyr Cys Asn Val Asp Tyr Leu Gln Asp Tyr
        115                 120                 125

Trp Gly Gln Gly Thr Gln Val Thr Val Ser Ser Gly Gly Gly Gly Ser
    130                 135                 140

Gly Gly Gly Gly Ser Gly Gly Gly Gly Ser Asp Gly Asn Glu Glu Met
145                 150                 155                 160

Gly Gly Ile Thr Gln Thr Pro Tyr Lys Val Ser Ile Ser Gly Thr Thr
                165                 170                 175

Val Ile Leu Thr Cys Pro Gln Tyr Pro Gly Ser Glu Ile Leu Trp Gln
            180                 185                 190

His Asn Asp Lys Asn Ile Gly Gly Asp Glu Asp Asp Lys Asn Ile Gly
        195                 200                 205

Ser Asp Glu Asp His Leu Ser Leu Lys Glu Phe Ser Glu Leu Glu Gln
    210                 215                 220

Ser Gly Tyr Tyr Val Cys Tyr Pro Arg Gly Ser Lys Pro Glu Asp Ala
225                 230                 235                 240

Asn Phe Tyr Leu Tyr Leu Arg Ala Arg Val Cys Glu Asn Cys Met Glu
                245                 250                 255

Met Asp Val Met Ser Val Ala Thr Ile Val Ile Val Asp Ile Cys Ile
            260                 265                 270

Thr Gly Gly Leu Leu Leu Leu Val Tyr Tyr Trp Ser Lys Asn Arg Lys
        275                 280                 285

Ala Lys Ala Lys Pro Val Thr Arg Gly Ala Gly Ala Gly Gly Arg Gln
    290                 295                 300

Arg Gly Gln Asn Lys Glu Arg Pro Pro Pro Val Pro Asn Pro Asp Tyr
305                 310                 315                 320

Glu Pro Ile Arg Lys Gly Gln Arg Asp Leu Tyr Ser Gly Leu Asn Gln
                325                 330                 335

Arg Arg Ile
```

<210> SEQ ID NO 33
<211> LENGTH: 639
<212> TYPE: DNA
<213> ORGANISM: Artificial Sequence
<220> FEATURE:
<223> OTHER INFORMATION: Truncated ERBB2

<400> SEQUENCE: 33

```
atgctgctcc tcgtcaccag cctcctcctc tgcgaactcc cccaccccgc cttcctgctg      60
```

```
attcccgctt gccaccagct gtgcgcccgg ggacactgct ggggaccagg acctacccag    120

tgcgtgaact gcagccagtt cctccgcggt caggaatgcg tcgaagaatg ccgggttctg    180

cagggactgc ccagagaata cgttaacgcc agacactgcc tgccctgcca ccccgaatgt    240

cagccccaga acggctccgt cacctgtttc ggccccgagg cagaccaatg cgtggcctgc    300

gctcactaca aggaccccc  cttctgcgtg gcccgttgcc cttccggcgt gaagcccgac    360

ctctcctaca tgcccatttg gaagttcccc gatgaggaag gcgcctgcca gccctgtccc    420

atcaactgca cccactcctg cgttgacctg gacgacaagg gctgtcccgc cgaacagaga    480

gccagccccc tcacctctat catctccgcc gtggtgggca ttctgctggt cgtggtcctg    540

ggcgttgtgt tcggcatcct gatcaaaaga agacaacaaa agatcagaaa gtacaccatg    600

cggcgcctcc tggactacaa ggacgatgat gataagtaa                           639
```

```
<210> SEQ ID NO 34
<211> LENGTH: 212
<212> TYPE: PRT
<213> ORGANISM: Artificial Sequence
<220> FEATURE:
<223> OTHER INFORMATION: Truncated ERBB2

<400> SEQUENCE: 34

Met Leu Leu Leu Val Thr Ser Leu Leu Leu Cys Glu Leu Pro His Pro
1               5                   10                  15

Ala Phe Leu Leu Ile Pro Ala Cys His Gln Leu Cys Ala Arg Gly His
            20                  25                  30

Cys Trp Gly Pro Gly Pro Thr Gln Cys Val Asn Cys Ser Gln Phe Leu
        35                  40                  45

Arg Gly Gln Glu Cys Val Glu Glu Cys Arg Val Leu Gln Gly Leu Pro
    50                  55                  60

Arg Glu Tyr Val Asn Ala Arg His Cys Leu Pro Cys His Pro Glu Cys
65                  70                  75                  80

Gln Pro Gln Asn Gly Ser Val Thr Cys Phe Gly Pro Glu Ala Asp Gln
                85                  90                  95

Cys Val Ala Cys Ala His Tyr Lys Asp Pro Pro Phe Cys Val Ala Arg
            100                 105                 110

Cys Pro Ser Gly Val Lys Pro Asp Leu Ser Tyr Met Pro Ile Trp Lys
        115                 120                 125

Phe Pro Asp Glu Glu Gly Ala Cys Gln Pro Cys Pro Ile Asn Cys Thr
    130                 135                 140

His Ser Cys Val Asp Leu Asp Asp Lys Gly Cys Pro Ala Glu Gln Arg
145                 150                 155                 160

Ala Ser Pro Leu Thr Ser Ile Ile Ser Ala Val Val Gly Ile Leu Leu
                165                 170                 175

Val Val Val Leu Gly Val Val Phe Gly Ile Leu Ile Lys Arg Arg Gln
            180                 185                 190

Gln Lys Ile Arg Lys Tyr Thr Met Arg Arg Leu Leu Asp Tyr Lys Asp
        195                 200                 205

Asp Asp Asp Lys
    210


<210> SEQ ID NO 35
<211> LENGTH: 18
<212> TYPE: DNA
<213> ORGANISM: Artificial Sequence
<220> FEATURE:
```

<223> OTHER INFORMATION: 6xHis

<400> SEQUENCE: 35
caccaccacc accatcac 18

<210> SEQ ID NO 36
<211> LENGTH: 6
<212> TYPE: PRT
<213> ORGANISM: Artificial Sequence
<220> FEATURE:
<223> OTHER INFORMATION: 6xHis

<400> SEQUENCE: 36

His His His His His His
1 5

<210> SEQ ID NO 37
<211> LENGTH: 1881
<212> TYPE: DNA
<213> ORGANISM: Artificial Sequence
<220> FEATURE:
<223> OTHER INFORMATION: CAIX-BiTA

<400> SEQUENCE: 37
atgctgctgc tggtgacctc cctgctgctg tgcgagctgc cccaccccgc tttcctgctg 60
atcccccagg tgcagctgca ggagtctggc ggcggcctgg tgcagcctgg aggatctctg 120
agactgagct gcgccgcctc cggcaacagc gctaacatct tttcctttgc ttccgtggcc 180
tggtataggc aggccccagg gaagcagaga gagctggtgg ccgtcattac atccgccggc 240
ggcacaaagt actccgactc tgtgaaggga agattcacca ttagccggga caatgccaag 300
aacaccattc tgctgcagat gaactcactg aaacctgagg ataccgccgt gtattattgt 360
aacgtggact acctgcagga ctactggggg cagggcaccc aggtgacagt gagcagcggc 420
ggcggcggaa gcgatatcaa gctgcagcag agcggagccg agctggccag gcctggagct 480
agcgtgaaga tgagctgcaa aaccagcggc tacacattca ccagatacac catgcattgg 540
gtgaagcaga gacccggaca gggactggag tggattggat acattaaccc cagtcgaggc 600
tacaccaact acaaccagaa gttcaaagac aaagccaccc tgaccaccga caaaagcagc 660
agcaccgcat atatgcagct gagctctctg accagcgagg acagcgccgt gtactactgc 720
gccagatact acgacgacca ctactgcctg gactactggg gccagggaac caccctgaca 780
gtgtctagcg tggagggcgg atctggcggc tcaggcggaa gcggagggag cggaggagtg 840
gacgatatcc agctgaccca gagtcccgcc atcatgagtg caagtcccgg cgaaaaagtg 900
accatgacct gtagagcttc ttctagtgtg agttatatga actggtacca gcagaagagc 960
gggaccagcc ccaaaagatg gatctacgac accagcaagg tggccagcgg cgtgccctac 1020
cggttcagcg gatctggcag cggaacctca tacagcctga ctatcagcag catggaagca 1080
gaagacgccg caacctacta ctgccagcag tggagctcta acccactgac cttcggcgct 1140
ggcaccaagc tggagctgaa gcaccaccac caccatcacg gcagcggcga aggcagaggc 1200
agcctcctga catgcggcga cgtcgaagaa aaccccggcc ccatgctgct cctcgtcacc 1260
agcctcctcc tctgcgaact cccccacccc gccttcctgc tgattcccgc ttgccaccag 1320
ctgtgcgccc ggggacactg ctggggacca ggacctaccc agtgcgtgaa ctgcagccag 1380
ttcctccgcg gtcaggaatg cgtcgaagaa tgccgggttc tgcagggact gcccagagaa 1440
tacgttaacg ccagacactg cctgccctgc caccccgaat gtcagcccca gaacggctcc 1500

-continued

```
gtcacctgtt tcggccccga ggcagaccaa tgcgtggcct gcgctcacta caaggacccc   1560

cccttctgcg tggcccgttg cccttccggc gtgaagcccg acctctccta catgcccatt   1620

tggaagttcc ccgatgagga aggcgcctgc cagccctgtc ccatcaactg cacccactcc   1680

tgcgttgacc tggacgacaa gggctgtccc gccgaacaga gagccagccc cctcacctct   1740

atcatctccg ccgtggtggg cattctgctg gtcgtggtcc tgggcgttgt gttcggcatc   1800

ctgatcaaaa gaagacaaca aaagatcaga aagtacacca tgcggcgcct cctggactac   1860

aaggacgatg atgataagta a                                              1881
```

<210> SEQ ID NO 38
<211> LENGTH: 626
<212> TYPE: PRT
<213> ORGANISM: Artificial Sequence
<220> FEATURE:
<223> OTHER INFORMATION: CAIX-BiTA

<400> SEQUENCE: 38

```
Met Leu Leu Leu Val Thr Ser Leu Leu Leu Cys Glu Leu Pro His Pro
1               5                   10                  15

Ala Phe Leu Leu Ile Pro Gln Val Gln Leu Gln Glu Ser Gly Gly Gly
            20                  25                  30

Leu Val Gln Pro Gly Gly Ser Leu Arg Leu Ser Cys Ala Ala Ser Gly
        35                  40                  45

Asn Ser Ala Asn Ile Phe Ser Phe Ala Ser Val Ala Trp Tyr Arg Gln
    50                  55                  60

Ala Pro Gly Lys Gln Arg Glu Leu Val Ala Val Ile Thr Ser Ala Gly
65                  70                  75                  80

Gly Thr Lys Tyr Ser Asp Ser Val Lys Gly Arg Phe Thr Ile Ser Arg
                85                  90                  95

Asp Asn Ala Lys Asn Thr Ile Leu Leu Gln Met Asn Ser Leu Lys Pro
            100                 105                 110

Glu Asp Thr Ala Val Tyr Tyr Cys Asn Val Asp Tyr Leu Gln Asp Tyr
        115                 120                 125

Trp Gly Gln Gly Thr Gln Val Thr Val Ser Ser Gly Gly Gly Gly Ser
    130                 135                 140

Asp Ile Lys Leu Gln Gln Ser Gly Ala Glu Leu Ala Arg Pro Gly Ala
145                 150                 155                 160

Ser Val Lys Met Ser Cys Lys Thr Ser Gly Tyr Thr Phe Thr Arg Tyr
                165                 170                 175

Thr Met His Trp Val Lys Gln Arg Pro Gly Gln Gly Leu Glu Trp Ile
            180                 185                 190

Gly Tyr Ile Asn Pro Ser Arg Gly Tyr Thr Asn Tyr Asn Gln Lys Phe
        195                 200                 205

Lys Asp Lys Ala Thr Leu Thr Thr Asp Lys Ser Ser Ser Thr Ala Tyr
    210                 215                 220

Met Gln Leu Ser Ser Leu Thr Ser Glu Asp Ser Ala Val Tyr Tyr Cys
225                 230                 235                 240

Ala Arg Tyr Tyr Asp Asp His Tyr Cys Leu Asp Tyr Trp Gly Gln Gly
                245                 250                 255

Thr Thr Leu Thr Val Ser Ser Val Glu Gly Gly Ser Gly Gly Ser Gly
            260                 265                 270

Gly Ser Gly Gly Ser Gly Gly Val Asp Asp Ile Gln Leu Thr Gln Ser
        275                 280                 285

Pro Ala Ile Met Ser Ala Ser Pro Gly Glu Lys Val Thr Met Thr Cys
```

```
    290                 295                 300

Arg Ala Ser Ser Ser Val Ser Tyr Met Asn Trp Tyr Gln Gln Lys Ser
305                 310                 315                 320

Gly Thr Ser Pro Lys Arg Trp Ile Tyr Asp Thr Ser Lys Val Ala Ser
                325                 330                 335

Gly Val Pro Tyr Arg Phe Ser Gly Ser Gly Ser Gly Thr Ser Tyr Ser
            340                 345                 350

Leu Thr Ile Ser Ser Met Glu Ala Glu Asp Ala Ala Thr Tyr Tyr Cys
        355                 360                 365

Gln Gln Trp Ser Ser Asn Pro Leu Thr Phe Gly Ala Gly Thr Lys Leu
    370                 375                 380

Glu Leu Lys His His His His His His Gly Ser Gly Glu Gly Arg Gly
385                 390                 395                 400

Ser Leu Leu Thr Cys Gly Asp Val Glu Glu Asn Pro Gly Pro Met Leu
                405                 410                 415

Leu Leu Val Thr Ser Leu Leu Leu Cys Glu Leu Pro His Pro Ala Phe
            420                 425                 430

Leu Leu Ile Pro Ala Cys His Gln Leu Cys Ala Arg Gly His Cys Trp
        435                 440                 445

Gly Pro Gly Pro Thr Gln Cys Val Asn Cys Ser Gln Phe Leu Arg Gly
    450                 455                 460

Gln Glu Cys Val Glu Glu Cys Arg Val Leu Gln Gly Leu Pro Arg Glu
465                 470                 475                 480

Tyr Val Asn Ala Arg His Cys Leu Pro Cys His Pro Glu Cys Gln Pro
                485                 490                 495

Gln Asn Gly Ser Val Thr Cys Phe Gly Pro Glu Ala Asp Gln Cys Val
            500                 505                 510

Ala Cys Ala His Tyr Lys Asp Pro Pro Phe Cys Val Ala Arg Cys Pro
        515                 520                 525

Ser Gly Val Lys Pro Asp Leu Ser Tyr Met Pro Ile Trp Lys Phe Pro
    530                 535                 540

Asp Glu Glu Gly Ala Cys Gln Pro Cys Pro Ile Asn Cys Thr His Ser
545                 550                 555                 560

Cys Val Asp Leu Asp Asp Lys Gly Cys Pro Ala Glu Gln Arg Ala Ser
                565                 570                 575

Pro Leu Thr Ser Ile Ile Ser Ala Val Val Gly Ile Leu Leu Val Val
            580                 585                 590

Val Leu Gly Val Val Phe Gly Ile Leu Ile Lys Arg Arg Gln Gln Lys
        595                 600                 605

Ile Arg Lys Tyr Thr Met Arg Arg Leu Leu Asp Tyr Lys Asp Asp Asp
    610                 615                 620

Asp Lys
625


<210> SEQ ID NO 39
<211> LENGTH: 2316
<212> TYPE: DNA
<213> ORGANISM: Artificial Sequence
<220> FEATURE:
<223> OTHER INFORMATION: CAIX-CAB

<400> SEQUENCE: 39

atgctgctgc tggtgacctc cctgctgctg tgcgagctgc cccaccccgc tttcctgctg      60

atccccgacg gcaacgagga gatgggcggc atcacccaga ccccctacaa ggtgtccatc     120
```

```
tccggcacca ccgtgatcct gacctgccct cagtaccccg gctccgagat cctgtggcag    180
cacaacgata agaacatcgg cggagacgag gacgacaaga acatcggaag tgacgaggac    240
cacctgagcc tgaaggaatt cagcgaactg gagcagagcg gctattacgt ctgctacccc    300
agaggaagca aaccagagga cgccaacttc tatctgtacc tgagagccag agtgtgcgag    360
aactgcatgg aaatggacac aaccaccccc gcccccagac ccccaacccc tgctcctacc    420
attgccagcc agccactgtc cctgaggccc gaagcctgca gaccagcagc cggcggagcc    480
gtgcacacca gaggactgga cttcgcctgc gacatctaca tctgggcccc cctggccggg    540
acctgcggag tgctgctgct gagcctggtg attactctgt actgtaagag gggaagaaag    600
aaactgctgt atatcttcaa gcagcccttt atgagacccg tgcagaccac ccaggaggag    660
gacggctgct cctgtagatt ccccgaggag gaggagggcg gctgcgagct gagagtgaag    720
ttctccagga gcgccgacgc ccccgcctac cagcagggac agaaccagct gtacaacgag    780
ctgaacctgg gcagaagaga ggagtatgac gtgctggaca agagaagagg aagagacccc    840
gagatgggag gaaagccaag aagaaagaac ccccaggagg gcctgtacaa tgagctgcag    900
aaggacaaga tggcagaggc atatagcgag atcggaatga agggagagag aagaagagga    960
aagggacacg acggactgta ccagggcctg agcacagcta caaaggacac atacgacgca   1020
ctgcacatgc aggcactgcc accaagagac tacaaggacg atgacgacaa gggaagcgga   1080
gagggcagag gaagcctgct gacatgcgga gacgtggagg agaacccagg acccatgctg   1140
ctgctggtga cctccctgct gctgtgcgag ctgccccacc ccgctttcct gctgatcccc   1200
caggtgcagc tgcaggagtc tggcggcggc ctggtgcagc ctggaggatc tctgagactg   1260
agctgcgccg cctccggcaa cagcgctaac atcttttcct ttgcttccgt ggcctggtat   1320
aggcaggccc cagggaagca gagagagctg gtggccgtca ttacatccgc cggcggcaca   1380
aagtactccg actctgtgaa gggaagattc accattagcc gggacaatgc caagaacacc   1440
attctgctgc agatgaactc actgaaacct gaggataccg ccgtgtatta ttgtaacgtg   1500
gactacctgc aggactactg gggcagggc acccaggtga cagtgagcag cggcggcggc   1560
ggaagcgata tcaagctgca gcagagcgga gccgagctgg ccaggcctgg agctagcgtg   1620
aagatgagct gcaaaaccag cggctacaca ttcaccagat acaccatgca ttgggtgaag   1680
cagagacccg gacagggact ggagtggatt ggatacatta accccagtcg aggctacacc   1740
aactacaacc agaagttcaa agacaaagcc accctgacca ccgacaaaag cagcagcacc   1800
gcatatatgc agctgagctc tctgaccagc gaggacagcg ccgtgtacta ctgcgccaga   1860
tactacgacg accactactg cctggactac tggggccagg gaaccaccct gacagtgtct   1920
agcgtggagg gcggatctgg cggctcaggc ggaagcggag ggagcggagg agtggacgat   1980
atccagctga cccagagtcc cgccatcatg agtgcaagtc ccggcgaaaa agtgaccatg   2040
acctgtagag cttcttctag tgtgagttat atgaactggt accagcagaa gagcgggacc   2100
agccccaaaa gatggatcta cgacaccagc aaggtggcca gcggcgtgcc ctaccggttc   2160
agcggatctg gcagcggaac ctcatacagc ctgactatca gcagcatgga agcagaagac   2220
gccgcaacct actactgcca gcagtggagc tctaacccac tgaccttcgg cgctggcacc   2280
aagctggagc tgaagcacca ccaccaccat cactaa                             2316
```

<210> SEQ ID NO 40
<211> LENGTH: 771
<212> TYPE: PRT
<213> ORGANISM: Artificial Sequence

<220> FEATURE:
<223> OTHER INFORMATION: CAIX-CAB

<400> SEQUENCE: 40

Met Leu Leu Leu Val Thr Ser Leu Leu Leu Cys Glu Leu Pro His Pro
1 5 10 15

Ala Phe Leu Leu Ile Pro Asp Gly Asn Glu Glu Met Gly Gly Ile Thr
20 25 30

Gln Thr Pro Tyr Lys Val Ser Ile Ser Gly Thr Thr Val Ile Leu Thr
35 40 45

Cys Pro Gln Tyr Pro Gly Ser Glu Ile Leu Trp Gln His Asn Asp Lys
50 55 60

Asn Ile Gly Gly Asp Glu Asp Asp Lys Asn Ile Gly Ser Asp Glu Asp
65 70 75 80

His Leu Ser Leu Lys Glu Phe Ser Glu Leu Glu Gln Ser Gly Tyr Tyr
85 90 95

Val Cys Tyr Pro Arg Gly Ser Lys Pro Glu Asp Ala Asn Phe Tyr Leu
100 105 110

Tyr Leu Arg Ala Arg Val Cys Glu Asn Cys Met Glu Met Asp Thr Thr
115 120 125

Thr Pro Ala Pro Arg Pro Pro Thr Pro Ala Pro Thr Ile Ala Ser Gln
130 135 140

Pro Leu Ser Leu Arg Pro Glu Ala Cys Arg Pro Ala Ala Gly Gly Ala
145 150 155 160

Val His Thr Arg Gly Leu Asp Phe Ala Cys Asp Ile Tyr Ile Trp Ala
165 170 175

Pro Leu Ala Gly Thr Cys Gly Val Leu Leu Leu Ser Leu Val Ile Thr
180 185 190

Leu Tyr Cys Lys Arg Gly Arg Lys Lys Leu Leu Tyr Ile Phe Lys Gln
195 200 205

Pro Phe Met Arg Pro Val Gln Thr Thr Gln Glu Glu Asp Gly Cys Ser
210 215 220

Cys Arg Phe Pro Glu Glu Glu Glu Gly Gly Cys Glu Leu Arg Val Lys
225 230 235 240

Phe Ser Arg Ser Ala Asp Ala Pro Ala Tyr Gln Gln Gly Gln Asn Gln
245 250 255

Leu Tyr Asn Glu Leu Asn Leu Gly Arg Arg Glu Glu Tyr Asp Val Leu
260 265 270

Asp Lys Arg Arg Gly Arg Asp Pro Glu Met Gly Gly Lys Pro Arg Arg
275 280 285

Lys Asn Pro Gln Glu Gly Leu Tyr Asn Glu Leu Gln Lys Asp Lys Met
290 295 300

Ala Glu Ala Tyr Ser Glu Ile Gly Met Lys Gly Glu Arg Arg Arg Gly
305 310 315 320

Lys Gly His Asp Gly Leu Tyr Gln Gly Leu Ser Thr Ala Thr Lys Asp
325 330 335

Thr Tyr Asp Ala Leu His Met Gln Ala Leu Pro Pro Arg Asp Tyr Lys
340 345 350

Asp Asp Asp Asp Lys Gly Ser Gly Glu Gly Arg Gly Ser Leu Leu Thr
355 360 365

Cys Gly Asp Val Glu Glu Asn Pro Gly Pro Met Leu Leu Leu Val Thr
370 375 380

Ser Leu Leu Leu Cys Glu Leu Pro His Pro Ala Phe Leu Leu Ile Pro
385 390 395 400

```
Gln Val Gln Leu Gln Glu Ser Gly Gly Gly Leu Val Gln Pro Gly Gly
                405                 410                 415

Ser Leu Arg Leu Ser Cys Ala Ala Ser Gly Asn Ser Ala Asn Ile Phe
            420                 425                 430

Ser Phe Ala Ser Val Ala Trp Tyr Arg Gln Ala Pro Gly Lys Gln Arg
        435                 440                 445

Glu Leu Val Ala Val Ile Thr Ser Ala Gly Gly Thr Lys Tyr Ser Asp
    450                 455                 460

Ser Val Lys Gly Arg Phe Thr Ile Ser Arg Asp Asn Ala Lys Asn Thr
465                 470                 475                 480

Ile Leu Leu Gln Met Asn Ser Leu Lys Pro Glu Asp Thr Ala Val Tyr
                485                 490                 495

Tyr Cys Asn Val Asp Tyr Leu Gln Asp Tyr Trp Gly Gln Gly Thr Gln
            500                 505                 510

Val Thr Val Ser Ser Gly Gly Gly Gly Ser Asp Ile Lys Leu Gln Gln
        515                 520                 525

Ser Gly Ala Glu Leu Ala Arg Pro Gly Ala Ser Val Lys Met Ser Cys
    530                 535                 540

Lys Thr Ser Gly Tyr Thr Phe Thr Arg Tyr Thr Met His Trp Val Lys
545                 550                 555                 560

Gln Arg Pro Gly Gln Gly Leu Glu Trp Ile Gly Tyr Ile Asn Pro Ser
                565                 570                 575

Arg Gly Tyr Thr Asn Tyr Asn Gln Lys Phe Lys Asp Lys Ala Thr Leu
            580                 585                 590

Thr Thr Asp Lys Ser Ser Ser Thr Ala Tyr Met Gln Leu Ser Ser Leu
        595                 600                 605

Thr Ser Glu Asp Ser Ala Val Tyr Tyr Cys Ala Arg Tyr Tyr Asp Asp
    610                 615                 620

His Tyr Cys Leu Asp Tyr Trp Gly Gln Gly Thr Thr Leu Thr Val Ser
625                 630                 635                 640

Ser Val Glu Gly Gly Ser Gly Gly Ser Gly Gly Ser Gly Gly Ser Gly
                645                 650                 655

Gly Val Asp Asp Ile Gln Leu Thr Gln Ser Pro Ala Ile Met Ser Ala
            660                 665                 670

Ser Pro Gly Glu Lys Val Thr Met Thr Cys Arg Ala Ser Ser Ser Val
        675                 680                 685

Ser Tyr Met Asn Trp Tyr Gln Gln Lys Ser Gly Thr Ser Pro Lys Arg
    690                 695                 700

Trp Ile Tyr Asp Thr Ser Lys Val Ala Ser Gly Val Pro Tyr Arg Phe
705                 710                 715                 720

Ser Gly Ser Gly Ser Gly Thr Ser Tyr Ser Leu Thr Ile Ser Ser Met
                725                 730                 735

Glu Ala Glu Asp Ala Ala Thr Tyr Tyr Cys Gln Gln Trp Ser Ser Asn
            740                 745                 750

Pro Leu Thr Phe Gly Ala Gly Thr Lys Leu Glu Leu Lys His His His
        755                 760                 765

His His His
    770
```

<210> SEQ ID NO 41
<211> LENGTH: 987
<212> TYPE: DNA
<213> ORGANISM: Artificial Sequence
<220> FEATURE:

<223> OTHER INFORMATION: CAIX-Zeta

<400> SEQUENCE: 41
atgctgctgc tggtgacctc cctgctgctg tgcgagctgc cccaccccgc tttcctgctg 60
atcccccagg tgcagctgca ggagtctggc ggcggcctgg tgcagcctgg aggatctctg 120
agactgagct gcgccgcctc cggcaacagc gctaacatct ttcctttgc ttccgtggcc 180 tggtataggc aggccccagg gaagcagaga gagctggtgg ccgtcattac atccgccggc 240
ggcacaaagt actccgactc tgtgaaggga agattcacca ttagccggga caatgccaag 300
aacaccattc tgctgcagat gaactcactg aaacctgagg ataccgccgt gtattattgt 360
aacgtggact acctgcagga ctactggggg cagggcaccc aggtgacagt gagcagcacc 420
accacccccg caccaagacc ccccacccca gcaccaacca tcgccagcca gcccctgagc 480
ctgagacccg aagcctgcag acccgccgcc ggaggagcag tgcacaccag aggcctggac 540
ttcgcctgcg acatctacat ctgggccccc ctggccggca cctgcggagt gctgctgctg 600
agcctggtga tcaccctgta ttgtagagtg aagttttcta gaagcgcaga tgctcccgcc 660
tatcagcagg gccagaacca gctgtacaac gaactgaacc tgggcaggag agaagagtac 720
gacgtgctgg acaaaagaag aggcagagac cccgagatgg gagggaagcc cagaagaaag 780
aacccccagg agggcctgta caacgagctg cagaaagaca agatggcaga ggcatacagc 840
gagatcggaa tgaagggaga gagaagaaga ggaaagggac acgacggact gtaccagggc 900
ctgagcacag ctacaaagga cacatacgac gccctgcaca tgcaggccct gcccccaaga 960
gattacaagg acgacgatga caagtaa 987

<210> SEQ ID NO 42
<211> LENGTH: 328
<212> TYPE: PRT
<213> ORGANISM: Artificial Sequence
<220> FEATURE:
<223> OTHER INFORMATION: CAIX-Zeta

<400> SEQUENCE: 42

Met Leu Leu Leu Val Thr Ser Leu Leu Leu Cys Glu Leu Pro His Pro
1 5 10 15

Ala Phe Leu Leu Ile Pro Gln Val Gln Leu Gln Glu Ser Gly Gly Gly
20 25 30

Leu Val Gln Pro Gly Gly Ser Leu Arg Leu Ser Cys Ala Ala Ser Gly
35 40 45

Asn Ser Ala Asn Ile Phe Ser Phe Ala Ser Val Ala Trp Tyr Arg Gln
50 55 60

Ala Pro Gly Lys Gln Arg Glu Leu Val Ala Val Ile Thr Ser Ala Gly
65 70 75 80

Gly Thr Lys Tyr Ser Asp Ser Val Lys Gly Arg Phe Thr Ile Ser Arg
85 90 95

Asp Asn Ala Lys Asn Thr Ile Leu Leu Gln Met Asn Ser Leu Lys Pro
100 105 110

Glu Asp Thr Ala Val Tyr Tyr Cys Asn Val Asp Tyr Leu Gln Asp Tyr
115 120 125

Trp Gly Gln Gly Thr Gln Val Thr Val Ser Ser Thr Thr Thr Pro Ala
130 135 140

Pro Arg Pro Pro Thr Pro Ala Pro Thr Ile Ala Ser Gln Pro Leu Ser
145 150 155 160

Leu Arg Pro Glu Ala Cys Arg Pro Ala Ala Gly Gly Ala Val His Thr

```
                165                 170                 175

Arg Gly Leu Asp Phe Ala Cys Asp Ile Tyr Ile Trp Ala Pro Leu Ala
            180                 185                 190

Gly Thr Cys Gly Val Leu Leu Leu Ser Leu Val Ile Thr Leu Tyr Cys
        195                 200                 205

Arg Val Lys Phe Ser Arg Ser Ala Asp Ala Pro Ala Tyr Gln Gln Gly
    210                 215                 220

Gln Asn Gln Leu Tyr Asn Glu Leu Asn Leu Gly Arg Arg Glu Glu Tyr
225                 230                 235                 240

Asp Val Leu Asp Lys Arg Arg Gly Arg Asp Pro Glu Met Gly Gly Lys
                245                 250                 255

Pro Arg Arg Lys Asn Pro Gln Glu Gly Leu Tyr Asn Glu Leu Gln Lys
            260                 265                 270

Asp Lys Met Ala Glu Ala Tyr Ser Glu Ile Gly Met Lys Gly Glu Arg
        275                 280                 285

Arg Arg Gly Lys Gly His Asp Gly Leu Tyr Gln Gly Leu Ser Thr Ala
    290                 295                 300

Thr Lys Asp Thr Tyr Asp Ala Leu His Met Gln Ala Leu Pro Pro Arg
305                 310                 315                 320

Asp Tyr Lys Asp Asp Asp Asp Lys
                325


<210> SEQ ID NO 43
<211> LENGTH: 63
<212> TYPE: DNA
<213> ORGANISM: Artificial Sequence
<220> FEATURE:
<223> OTHER INFORMATION: CD8L

<400> SEQUENCE: 43

atggccctgc ccgtgaccgc tctgctgctg cctctggccc tgctgctgca cgccgctaga      60

ccc                                                                    63


<210> SEQ ID NO 44
<211> LENGTH: 21
<212> TYPE: PRT
<213> ORGANISM: Artificial Sequence
<220> FEATURE:
<223> OTHER INFORMATION: CD8L

<400> SEQUENCE: 44

Met Ala Leu Pro Val Thr Ala Leu Leu Leu Pro Leu Ala Leu Leu Leu
1               5                   10                  15

His Ala Ala Arg Pro
            20


<210> SEQ ID NO 45
<211> LENGTH: 1110
<212> TYPE: DNA
<213> ORGANISM: Artificial Sequence
<220> FEATURE:
<223> OTHER INFORMATION: CAIX-BBzeta

<400> SEQUENCE: 45

atggccctgc ccgtgaccgc tctgctgctg cctctggccc tgctgctgca cgccgctaga      60

ccccaggtgc agctgcagga gtccggcgga ggcctggtgc agcctggagg aagcctgaga     120

ctgagctgcg ctgcctccgg caactccgcc aacattttct ccttcgcctc cgtggcctgg     180

tacaggcagg ccccaggcaa gcagagagag ctggtggcag tcattacatc cgccggcggc     240
```

```
accaagtaca gcgacagcgt gaagggacgg ttcactatct ccagagacaa tgccaagaac    300

acaatcctgc tgcagatgaa cagcctgaag cctgaggaca ccgcagtgta ttactgtaac    360

gtggactacc tgcaggacta ctggggccag ggcacccagg tgaccgtgtc cagcaccacc    420

acccccgccc ctagaccacc caccccagct ccaaccatcg cctctcagcc cctgagcctg    480

agacccgaag cctgccgccc cgctgcagga ggagcagtgc acaccagagg actggacttc    540

gcctgcgaca tctacatctg ggcccccctg gccggcacct gcggagtgct gctgctgagc    600

ctggtgatca ccctgtactg taagagaggc cggaagaaac tgctgtacat cttcaagcag    660

ccctttatgc ggcccgtgca gaccacccag gaagaagacg gatgctcctg ccggttcccc    720

gaggaggaag aaggcggctg cgagctgaga gtgaagtttt ccaggagcgc tgacgccccc    780

gcctaccagc agggacagaa ccagctgtac aacgagctga acctggggag acgggaggag    840

tacgacgtgc tggataagag aagaggaaga gacccagaga tgggaggaaa gccaagaaga    900

aagaacccac aggaaggcct gtacaacgaa ctgcagaagg acaagatggc agaggcatac    960

agcgagatcg gaatgaaggg agagagaaga agaggaaagg gacacgacgg actgtaccag   1020

ggactgagca cagctacaaa ggacacatac gacgcactgc acatgcaggc actgccacca   1080

agagactata aggacgacga cgacaaataa                                    1110
```

```
<210> SEQ ID NO 46
<211> LENGTH: 369
<212> TYPE: PRT
<213> ORGANISM: Artificial Sequence
<220> FEATURE:
<223> OTHER INFORMATION: CAIX-BBzeta

<400> SEQUENCE: 46

Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Gly Gly Leu
            20                  25                  30

Val Gln Pro Gly Gly Ser Leu Arg Leu Ser Cys Ala Ala Ser Gly Asn
        35                  40                  45

Ser Ala Asn Ile Phe Ser Phe Ala Ser Val Ala Trp Tyr Arg Gln Ala
    50                  55                  60

Pro Gly Lys Gln Arg Glu Leu Val Ala Val Ile Thr Ser Ala Gly Gly
65                  70                  75                  80

Thr Lys Tyr Ser Asp Ser Val Lys Gly Arg Phe Thr Ile Ser Arg Asp
                85                  90                  95

Asn Ala Lys Asn Thr Ile Leu Leu Gln Met Asn Ser Leu Lys Pro Glu
            100                 105                 110

Asp Thr Ala Val Tyr Tyr Cys Asn Val Asp Tyr Leu Gln Asp Tyr Trp
        115                 120                 125

Gly Gln Gly Thr Gln Val Thr Val Ser Ser Thr Thr Thr Pro Ala Pro
    130                 135                 140

Arg Pro Pro Thr Pro Ala Pro Thr Ile Ala Ser Gln Pro Leu Ser Leu
145                 150                 155                 160

Arg Pro Glu Ala Cys Arg Pro Ala Ala Gly Gly Ala Val His Thr Arg
                165                 170                 175

Gly Leu Asp Phe Ala Cys Asp Ile Tyr Ile Trp Ala Pro Leu Ala Gly
            180                 185                 190

Thr Cys Gly Val Leu Leu Leu Ser Leu Val Ile Thr Leu Tyr Cys Lys
        195                 200                 205
```

```
Arg Gly Arg Lys Lys Leu Leu Tyr Ile Phe Lys Gln Pro Phe Met Arg
    210                 215                 220

Pro Val Gln Thr Thr Gln Glu Glu Asp Gly Cys Ser Cys Arg Phe Pro
225                 230                 235                 240

Glu Glu Glu Glu Gly Gly Cys Glu Leu Arg Val Lys Phe Ser Arg Ser
                245                 250                 255

Ala Asp Ala Pro Ala Tyr Gln Gln Gly Gln Asn Gln Leu Tyr Asn Glu
            260                 265                 270

Leu Asn Leu Gly Arg Arg Glu Glu Tyr Asp Val Leu Asp Lys Arg Arg
        275                 280                 285

Gly Arg Asp Pro Glu Met Gly Gly Lys Pro Arg Arg Lys Asn Pro Gln
    290                 295                 300

Glu Gly Leu Tyr Asn Glu Leu Gln Lys Asp Lys Met Ala Glu Ala Tyr
305                 310                 315                 320

Ser Glu Ile Gly Met Lys Gly Glu Arg Arg Arg Gly Lys Gly His Asp
                325                 330                 335

Gly Leu Tyr Gln Gly Leu Ser Thr Ala Thr Lys Asp Thr Tyr Asp Ala
            340                 345                 350

Leu His Met Gln Ala Leu Pro Pro Arg Asp Tyr Lys Asp Asp Asp Asp
        355                 360                 365

Lys


<210> SEQ ID NO 47
<211> LENGTH: 1101
<212> TYPE: DNA
<213> ORGANISM: Artificial Sequence
<220> FEATURE:
<223> OTHER INFORMATION: CAIX-28zeta

<400> SEQUENCE: 47

atggccctgc ccgtgaccgc tctgctgctg cctctggccc tgctgctgca cgccgctaga     60

ccccaggtgc agctgcagga gtccggcgga ggcctggtgc agcctggagg aagcctgaga    120

ctgagctgcg ctgcctccgg caactccgcc aacattttct ccttcgcctc cgtggcctgg    180

tacaggcagg ccccaggcaa gcagagagag ctggtggcag tcattacatc cgccggcggc    240

accaagtaca gcgacagcgt gaagggacgg ttcactatct ccagagacaa tgccaagaac    300

acaatcctgc tgcagatgaa cagcctgaag cctgaggaca ccgcagtgta ttactgtaac    360

gtggactacc tgcaggacta ctggggccag ggcacccagg tgaccgtgtc cagcgccatc    420

gaggtgatgt acccccccccc ctacctggat aacgagaaga gtaatggcac cattatccat    480

gtgaagggca agcacctgtg ccccagccct ctgttccccg gccctagcaa acccttctgg    540

gtgctggtgg tcgtgggcgg cgtcctggct tgctactccc tgctggtgac cgtggccttt    600

atcatcttct gggtgaggtc caagcgctcc aggctgctgc acagcgatta catgaacatg    660

acccccagga gaccaggccc cacccggaag cactaccagc cctatgcccc cccccgcgac    720

ttcgctgctt atagaagcag agtcaagttc tcccgcagcg ccgacgcccc cgcataccag    780

cagggacaga accagctgta caacgaactg aacctgggcc ggagagagga atacgacgtg    840

ctggataaga gaagaggaag ggaccccgag atgggaggaa aaccaagaag aaagaaccca    900

caggagggcc tgtacaatga gctgcagaaa gacaagatgg cagaggcata tagcgagatc    960

ggaatgaagg gagagagaag aagaggaaag ggacacgacg gactgtacca gggactgagc   1020

acagctacaa aggacacata cgacgccctg cacatgcagg cactgccacc cagagactat   1080
```

aaggacgacg acgacaaata a 1101

<210> SEQ ID NO 48
<211> LENGTH: 366
<212> TYPE: PRT
<213> ORGANISM: Artificial Sequence
<220> FEATURE:
<223> OTHER INFORMATION: CAIX-28zeta

<400> SEQUENCE: 48

Met Ala Leu Pro Val Thr Ala Leu Leu Leu Pro Leu Ala Leu Leu Leu
1 5 10 15

His Ala Ala Arg Pro Gln Val Gln Leu Gln Glu Ser Gly Gly Gly Leu
20 25 30

Val Gln Pro Gly Gly Ser Leu Arg Leu Ser Cys Ala Ala Ser Gly Asn
35 40 45

Ser Ala Asn Ile Phe Ser Phe Ala Ser Val Ala Trp Tyr Arg Gln Ala
50 55 60

Pro Gly Lys Gln Arg Glu Leu Val Ala Val Ile Thr Ser Ala Gly Gly
65 70 75 80

Thr Lys Tyr Ser Asp Ser Val Lys Gly Arg Phe Thr Ile Ser Arg Asp
85 90 95

Asn Ala Lys Asn Thr Ile Leu Leu Gln Met Asn Ser Leu Lys Pro Glu
100 105 110

Asp Thr Ala Val Tyr Tyr Cys Asn Val Asp Tyr Leu Gln Asp Tyr Trp
115 120 125

Gly Gln Gly Thr Gln Val Thr Val Ser Ser Ala Ile Glu Val Met Tyr
130 135 140

Pro Pro Pro Tyr Leu Asp Asn Glu Lys Ser Asn Gly Thr Ile Ile His
145 150 155 160

Val Lys Gly Lys His Leu Cys Pro Ser Pro Leu Phe Pro Gly Pro Ser
165 170 175

Lys Pro Phe Trp Val Leu Val Val Val Gly Gly Val Leu Ala Cys Tyr
180 185 190

Ser Leu Leu Val Thr Val Ala Phe Ile Ile Phe Trp Val Arg Ser Lys
195 200 205

Arg Ser Arg Leu Leu His Ser Asp Tyr Met Asn Met Thr Pro Arg Arg
210 215 220

Pro Gly Pro Thr Arg Lys His Tyr Gln Pro Tyr Ala Pro Pro Arg Asp
225 230 235 240

Phe Ala Ala Tyr Arg Ser Arg Val Lys Phe Ser Arg Ser Ala Asp Ala
245 250 255

Pro Ala Tyr Gln Gln Gly Gln Asn Gln Leu Tyr Asn Glu Leu Asn Leu
260 265 270

Gly Arg Arg Glu Glu Tyr Asp Val Leu Asp Lys Arg Arg Gly Arg Asp
275 280 285

Pro Glu Met Gly Gly Lys Pro Arg Arg Lys Asn Pro Gln Glu Gly Leu
290 295 300

Tyr Asn Glu Leu Gln Lys Asp Lys Met Ala Glu Ala Tyr Ser Glu Ile
305 310 315 320

Gly Met Lys Gly Glu Arg Arg Arg Gly Lys Gly His Asp Gly Leu Tyr
325 330 335

Gln Gly Leu Ser Thr Ala Thr Lys Asp Thr Tyr Asp Ala Leu His Met
340 345 350

Gln Ala Leu Pro Pro Arg Asp Tyr Lys Asp Asp Asp Asp Lys 355 360 365

<210> SEQ ID NO 49
<211> LENGTH: 2700
<212> TYPE: DNA
<213> ORGANISM: Artificial Sequence
<220> FEATURE:
<223> OTHER INFORMATION: HER2-CAB

<400> SEQUENCE: 49
atgctgctgc tggtgacctc cctgctgctg tgcgagctgc cccaccccgc tttcctgctg 60
atccccgacg gcaacgagga gatgggcggc atcacccaga cccccctacaa ggtgtccatc 120 tccggcacca ccgtgatcct gacctgccct cagtaccccg gctccgagat cctgtggcag 180
cacaacgata agaacatcgg cggagacgag gacgacaaga acatcggaag tgacgaggac 240
cacctgagcc tgaaggaatt cagcgaactg gagcagagcg gctattacgt ctgctacccc 300
agaggaagca aaccagagga cgccaacttc tatctgtacc tgagagccag agtgtgcgag 360
aactgcatgg aaatggacac aaccaccccc gcccccagac cccaaccccc tgctcctacc 420
attgccagcc agccactgtc cctgaggccc gaagcctgca gaccagcagc cggcggagcc 480
gtgcacacca gaggactgga cttcgcctgc gacatctaca tctgggcccc cctggccggg 540
acctgcggag tgctgctgct gagcctggtg attactctgt actgtaagag gggaagaaag 600
aaactgctgt atatcttcaa gcagcccttt atgagacccg tgcagaccac ccaggaggag 660
gacggctgct cctgtagatt ccccgaggag gaggagggcg gctgcgagct gagagtgaag 720
ttctccagga gcgccgacgc ccccgcctac cagcagggac agaaccagct gtacaacgag 780
ctgaacctgg gcagaagaga ggagtatgac gtgctggaca agagaagagg aagagacccc 840
gagatgggag gaaagccaag aagaaagaac ccccaggagg gcctgtacaa tgagctgcag 900
aaggacaaga tggcagaggc atatagcgag atcggaatga agggagagag aagaagagga 960
aagggacacg acggactgta ccagggcctg agcacagcta caaaggacac atacgacgca 1020
ctgcacatgc aggcactgcc accaagagac tacaaggacg atgacgacaa gggaagcgga 1080
gagggcagag gaagcctgct gacatgcgga gacgtggagg agaacccagg acccatgctg 1140
ctgctggtga cctccctgct gctgtgcgag ctgccccacc ccgctttcct gctgatcccc 1200
gacatccaga tgacccagtc cccctcctcc ctgtccgcct ccgtgggaga ccgcgtgacc 1260
atcacctgcc gcgcctccca ggacgtgaac accgccgtcg cctggtacca gcagaagccc 1320
ggcaaagccc ccaaactgct gatctactcc gcctcattcc tgtatagcgg cgtgccctcc 1380
agattctccg gcagcagaag cggcaccgac ttcaccctga ctatcagcag cctgcagccc 1440
gaagacttcg ccacctacta ctgccagcag cactacacca cccccccac cttcggccag 1500 ggcacaaaag tggagatcaa gggcagcacc agcggcagcg gaaaacccgg cagcggcgag 1560
ggatctacca aaggcgaggt ccagctggtg gagagcggcg gaggcctggt gcagccagga 1620
ggaagcctga gactgagctg tgccgcaagc ggattcaata tcaaggatac atacattcat 1680
tgggtgagac aggcacccgg aaaaggcctg gagtgggtgg ctagaattta cccaaccaac 1740
ggatacaccc ggtacgccga tagcgtgaag ggcagattca ccattagcgc cgacaccagc 1800
aagaacacag cctacctgca gatgaacagc ctgagagccg aggacaccgc agtgtactac 1860
tgcagcagat ggggagggga cggattctac gccatggact actggggaca gggcaccctg 1920
gtgacagtga gcagcggcgg cggcggaagc gacattaagc tgcagcagag tggcgccgag 1980
ctggcaagac ccggagccag tgtgaagatg agctgcaaga ctagcggcta caccttcacc 2040
agatatacaa tgcattgggt gaaacagaga cccggccagg gactggagtg gattggatac 2100
attaacccca gcagaggcta caccaactac aaccagaagt tcaaggacaa ggcaaccctg 2160
accacagaca aaagcagcag cacagcctac atgcagctga gcagcctgac cagcgaggac 2220
agcgccgtgt actactgtgc cagatactac gacgaccact actgcctgga ctactggggc 2280
cagggaacca cactgaccgt gtccagcgtg gagggcggat caggcggcag cggaggaagc 2340
ggaggaagtg gggcgtgga cgacatccag ctgacacaga gtcccgctat catgagcgca 2400
agtcccggcg agaaggtgac aatgacctgc agagctagct caagcgtgag ctatatgaat 2460
tggtaccagc agaaaagcgg caccagcccc aaaagatgga tctacgacac ctcaaaggtg 2520
gccagcggag tgccctacag attcagcgga tcaggaagcg gaacatcata cagcctgact 2580
atctccagca tggaggctga agacgccgca acctactact gtcagcagtg gagctctaac 2640
cccctgacct tcggcgccgg caccaagctg gagctgaagc accaccacca ccatcactaa 2700

<210> SEQ ID NO 50
<211> LENGTH: 899
<212> TYPE: PRT
<213> ORGANISM: Artificial Sequence
<220> FEATURE:
<223> OTHER INFORMATION: HER2-CAB

<400> SEQUENCE: 50

Met Leu Leu Leu Val Thr Ser Leu Leu Leu Cys Glu Leu Pro His Pro
1 5 10 15

Ala Phe Leu Leu Ile Pro Asp Gly Asn Glu Glu Met Gly Gly Ile Thr
20 25 30

Gln Thr Pro Tyr Lys Val Ser Ile Ser Gly Thr Thr Val Ile Leu Thr
35 40 45

Cys Pro Gln Tyr Pro Gly Ser Glu Ile Leu Trp Gln His Asn Asp Lys
50 55 60

Asn Ile Gly Gly Asp Glu Asp Asp Lys Asn Ile Gly Ser Asp Glu Asp
65 70 75 80

His Leu Ser Leu Lys Glu Phe Ser Glu Leu Glu Gln Ser Gly Tyr Tyr
85 90 95

Val Cys Tyr Pro Arg Gly Ser Lys Pro Glu Asp Ala Asn Phe Tyr Leu
100 105 110

Tyr Leu Arg Ala Arg Val Cys Glu Asn Cys Met Glu Met Asp Thr Thr
115 120 125

Thr Pro Ala Pro Arg Pro Pro Thr Pro Ala Pro Thr Ile Ala Ser Gln
130 135 140

Pro Leu Ser Leu Arg Pro Glu Ala Cys Arg Pro Ala Ala Gly Gly Ala
145 150 155 160

Val His Thr Arg Gly Leu Asp Phe Ala Cys Asp Ile Tyr Ile Trp Ala
165 170 175

Pro Leu Ala Gly Thr Cys Gly Val Leu Leu Leu Ser Leu Val Ile Thr
180 185 190

Leu Tyr Cys Lys Arg Gly Arg Lys Lys Leu Leu Tyr Ile Phe Lys Gln
195 200 205

Pro Phe Met Arg Pro Val Gln Thr Thr Gln Glu Glu Asp Gly Cys Ser
210 215 220

Cys Arg Phe Pro Glu Glu Glu Glu Gly Gly Cys Glu Leu Arg Val Lys
225 230 235 240

Phe Ser Arg Ser Ala Asp Ala Pro Ala Tyr Gln Gln Gly Gln Asn Gln

```
                245                 250                 255

Leu Tyr Asn Glu Leu Asn Leu Gly Arg Arg Glu Glu Tyr Asp Val Leu
            260                 265                 270

Asp Lys Arg Arg Gly Arg Asp Pro Glu Met Gly Gly Lys Pro Arg Arg
        275                 280                 285

Lys Asn Pro Gln Glu Gly Leu Tyr Asn Glu Leu Gln Lys Asp Lys Met
    290                 295                 300

Ala Glu Ala Tyr Ser Glu Ile Gly Met Lys Gly Glu Arg Arg Arg Gly
305                 310                 315                 320

Lys Gly His Asp Gly Leu Tyr Gln Gly Leu Ser Thr Ala Thr Lys Asp
                325                 330                 335

Thr Tyr Asp Ala Leu His Met Gln Ala Leu Pro Pro Arg Asp Tyr Lys
            340                 345                 350

Asp Asp Asp Asp Lys Gly Ser Gly Glu Gly Arg Gly Ser Leu Leu Thr
        355                 360                 365

Cys Gly Asp Val Glu Glu Asn Pro Gly Pro Met Leu Leu Leu Val Thr
    370                 375                 380

Ser Leu Leu Leu Cys Glu Leu Pro His Pro Ala Phe Leu Leu Ile Pro
385                 390                 395                 400

Asp Ile Gln Met Thr Gln Ser Pro Ser Ser Leu Ser Ala Ser Val Gly
                405                 410                 415

Asp Arg Val Thr Ile Thr Cys Arg Ala Ser Gln Asp Val Asn Thr Ala
            420                 425                 430

Val Ala Trp Tyr Gln Gln Lys Pro Gly Lys Ala Pro Lys Leu Leu Ile
        435                 440                 445

Tyr Ser Ala Ser Phe Leu Tyr Ser Gly Val Pro Ser Arg Phe Ser Gly
    450                 455                 460

Ser Arg Ser Gly Thr Asp Phe Thr Leu Thr Ile Ser Ser Leu Gln Pro
465                 470                 475                 480

Glu Asp Phe Ala Thr Tyr Tyr Cys Gln Gln His Tyr Thr Thr Pro Pro
                485                 490                 495

Thr Phe Gly Gln Gly Thr Lys Val Glu Ile Lys Gly Ser Thr Ser Gly
            500                 505                 510

Ser Gly Lys Pro Gly Ser Gly Glu Gly Ser Thr Lys Gly Glu Val Gln
        515                 520                 525

Leu Val Glu Ser Gly Gly Gly Leu Val Gln Pro Gly Gly Ser Leu Arg
    530                 535                 540

Leu Ser Cys Ala Ala Ser Gly Phe Asn Ile Lys Asp Thr Tyr Ile His
545                 550                 555                 560

Trp Val Arg Gln Ala Pro Gly Lys Gly Leu Glu Trp Val Ala Arg Ile
                565                 570                 575

Tyr Pro Thr Asn Gly Tyr Thr Arg Tyr Ala Asp Ser Val Lys Gly Arg
            580                 585                 590

Phe Thr Ile Ser Ala Asp Thr Ser Lys Asn Thr Ala Tyr Leu Gln Met
        595                 600                 605

Asn Ser Leu Arg Ala Glu Asp Thr Ala Val Tyr Tyr Cys Ser Arg Trp
    610                 615                 620

Gly Gly Asp Gly Phe Tyr Ala Met Asp Tyr Trp Gly Gln Gly Thr Leu
625                 630                 635                 640

Val Thr Val Ser Ser Gly Gly Gly Gly Ser Asp Ile Lys Leu Gln Gln
                645                 650                 655

Ser Gly Ala Glu Leu Ala Arg Pro Gly Ala Ser Val Lys Met Ser Cys
            660                 665                 670
```

Lys Thr Ser Gly Tyr Thr Phe Thr Arg Tyr Thr Met His Trp Val Lys
675 680 685

Gln Arg Pro Gly Gln Gly Leu Glu Trp Ile Gly Tyr Ile Asn Pro Ser
690 695 700

Arg Gly Tyr Thr Asn Tyr Asn Gln Lys Phe Lys Asp Lys Ala Thr Leu
705 710 715 720

Thr Thr Asp Lys Ser Ser Ser Thr Ala Tyr Met Gln Leu Ser Ser Leu
725 730 735

Thr Ser Glu Asp Ser Ala Val Tyr Tyr Cys Ala Arg Tyr Tyr Asp Asp
740 745 750

His Tyr Cys Leu Asp Tyr Trp Gly Gln Gly Thr Thr Leu Thr Val Ser
755 760 765

Ser Val Glu Gly Gly Ser Gly Gly Ser Gly Gly Ser Gly Gly Ser Gly
770 775 780

Gly Val Asp Asp Ile Gln Leu Thr Gln Ser Pro Ala Ile Met Ser Ala
785 790 795 800

Ser Pro Gly Glu Lys Val Thr Met Thr Cys Arg Ala Ser Ser Ser Val
805 810 815

Ser Tyr Met Asn Trp Tyr Gln Gln Lys Ser Gly Thr Ser Pro Lys Arg
820 825 830

Trp Ile Tyr Asp Thr Ser Lys Val Ala Ser Gly Val Pro Tyr Arg Phe
835 840 845

Ser Gly Ser Gly Ser Gly Thr Ser Tyr Ser Leu Thr Ile Ser Ser Met
850 855 860

Glu Ala Glu Asp Ala Ala Thr Tyr Tyr Cys Gln Gln Trp Ser Ser Asn
865 870 875 880

Pro Leu Thr Phe Gly Ala Gly Thr Lys Leu Glu Leu Lys His His His
885 890 895

His His His

<210> SEQ ID NO 51
<211> LENGTH: 1350
<212> TYPE: DNA
<213> ORGANISM: Artificial Sequence
<220> FEATURE:
<223> OTHER INFORMATION: HER2-Zeta

<400> SEQUENCE: 51
atggccctgc ccgtgaccgc cctgctgctg cccctggccc tgctgctgca cgccgcccgc 60
cccgacatcc agatgaccca gagccccagc agcctgagcg ccagcgtggg cgaccgcgtg 120
accatcacct gccgcgccag ccaggacgtg aacaccgccg tggcctggta ccagcagaag 180
cccggcaagg cccccaagct gctgatctac agcgccagct tcctgtacag cggcgtgccc 240
agccgcttca gcggcagccg cagcggcacc gacttcaccc tgaccatcag cagcctgcag 300
cccgaggact tcgccaccta ctactgccag cagcactaca ccaccccccc caccttcggc 360
cagggcacca aggtggagat caagggcagc accagcggca gcggcaagcc cggcagcggc 420
gagggcagca ccaagggcga ggtgcagctg gtggagagcg gcggcggcct ggtgcagccc 480
ggcggcagcc tgcgcctgag ctgcgccgcc agcggcttca acatcaagga cacctacatc 540
cactgggtgc gccaggcccc cggcaagggc ctggagtggg tggcccgcat ctaccccacc 600
aacggctaca cccgctacgc cgacagcgtg aagggccgct tcaccatcag cgccgacacc 660
agcaagaaca ccgcctacct gcagatgaac agcctgcgcg ccgaggacac cgccgtgtac 720

```
tactgcagcc gctggggcgg cgacggcttc tacgccatgg actactgggg ccagggcacc    780

ctggtgaccg tgagcagcac gcgtaccacc acccccgcac caagaccccc caccccagca    840

ccaaccatcg ccagccagcc cctgagcctg agacccgaag cctgcagacc cgccgccgga    900

ggagcagtgc acaccagagg cctggacttc gcctgcgaca tctacatctg ggcccccctg    960

gccggcacct gcggagtgct gctgctgagc ctggtgatca ccctgtattg tagagtgaag   1020

ttttctagaa gcgcagatgc tcccgcctat cagcagggcc agaaccagct gtacaacgaa   1080

ctgaacctgg gcaggagaga agagtacgac gtgctggaca aaagaagagg cagagacccc   1140

gagatgggag ggaagcccag aagaaagaac ccccaggagg gcctgtacaa cgagctgcag   1200

aaagacaaga tggcagaggc atacagcgag atcggaatga agggagagag aagaagagga   1260

aagggacacg acggactgta ccagggcctg agcacagcta caaaggacac atacgacgcc   1320

ctgcacatgc aggccctgcc cccaagataa                                    1350
```

<210> SEQ ID NO 52
<211> LENGTH: 449
<212> TYPE: PRT
<213> ORGANISM: Artificial Sequence
<220> FEATURE:
<223> OTHER INFORMATION: HER2-Zeta

<400> SEQUENCE: 52

```
Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Ser Leu
            20                  25                  30

Ser Ala Ser Val Gly Asp Arg Val Thr Ile Thr Cys Arg Ala Ser Gln
        35                  40                  45

Asp Val Asn Thr Ala Val Ala Trp Tyr Gln Gln Lys Pro Gly Lys Ala
    50                  55                  60

Pro Lys Leu Leu Ile Tyr Ser Ala Ser Phe Leu Tyr Ser Gly Val Pro
65                  70                  75                  80

Ser Arg Phe Ser Gly Ser Arg Ser Gly Thr Asp Phe Thr Leu Thr Ile
                85                  90                  95

Ser Ser Leu Gln Pro Glu Asp Phe Ala Thr Tyr Tyr Cys  Gln Gln His
            100                 105                 110

Tyr Thr Thr Pro Pro Thr Phe Gly Gln Gly Thr Lys Val Glu Ile Lys
        115                 120                 125

Gly Ser Thr Ser Gly Ser Gly Lys Pro Gly Ser Gly Glu Gly Ser Thr
    130                 135                 140

Lys Gly Glu Val Gln Leu Val Glu Ser Gly Gly Gly Leu Val Gln Pro
145                 150                 155                 160

Gly Gly Ser Leu Arg Leu Ser Cys Ala Ala Ser Gly Phe Asn Ile Lys
                165                 170                 175

Asp Thr Tyr Ile His Trp Val Arg Gln Ala Pro Gly Lys Gly Leu Glu
            180                 185                 190

Trp Val Ala Arg Ile Tyr Pro Thr Asn Gly Tyr Thr Arg Tyr Ala Asp
        195                 200                 205

Ser Val Lys Gly Arg Phe Thr Ile Ser Ala Asp Thr Ser Lys Asn Thr
    210                 215                 220

Ala Tyr Leu Gln Met Asn Ser Leu Arg Ala Glu Asp Thr Ala Val Tyr
225                 230                 235                 240

Tyr Cys Ser Arg Trp Gly Gly Asp Gly Phe Tyr Ala Met Asp Tyr Trp
                245                 250                 255
```

```
Gly Gln Gly Thr Leu Val Thr Val Ser Ser Thr Arg Thr Thr Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335

Cys Arg Val Lys Phe Ser Arg Ser Ala Asp Ala Pro Ala Tyr Gln Gln
            340                 345                 350

Gly Gln Asn Gln Leu Tyr Asn Glu Leu Asn Leu Gly Arg Arg Glu Glu
        355                 360                 365

Tyr Asp Val Leu Asp Lys Arg Arg Gly Arg Asp Pro Glu Met Gly Gly
    370                 375                 380

Lys Pro Arg Arg Lys Asn Pro Gln Glu Gly Leu Tyr Asn Glu Leu Gln
385                 390                 395                 400

Lys Asp Lys Met Ala Glu Ala Tyr Ser Glu Ile Gly Met Lys Gly Glu
                405                 410                 415

Arg Arg Arg Gly Lys Gly His Asp Gly Leu Tyr Gln Gly Leu Ser Thr
            420                 425                 430

Ala Thr Lys Asp Thr Tyr Asp Ala Leu His Met Gln Ala Leu Pro Pro
        435                 440                 445

Arg
```

<210> SEQ ID NO 53
<211> LENGTH: 1101
<212> TYPE: DNA
<213> ORGANISM: Artificial Sequence
<220> FEATURE:
<223> OTHER INFORMATION: HER2-BBzeta

<400> SEQUENCE: 53

```
atggccctgc ccgtgaccgc tctgctgctg cctctggccc tgctgctgca cgccgctaga     60

ccccaggtgc agctgcagga gtccggcgga ggcctggtgc agcctggagg aagcctgaga    120

ctgagctgcg ctgcctccgg caactccgcc aacattttct ccttcgcctc cgtggcctgg    180

tacaggcagg ccccaggcaa gcagagagag ctggtggcag tcattacatc cgccggcggc    240

accaagtaca gcgacagcgt gaagggacgg ttcactatct ccagagacaa tgccaagaac    300

acaatcctgc tgcagatgaa cagcctgaag cctgaggaca ccgcagtgta ttactgtaac    360

gtggactacc tgcaggacta ctggggccag ggcacccagg tgaccgtgtc cagcgccatc    420

gaggtgatgt accccccccc ctacctggat aacgagaaga gtaatggcac cattatccat    480

gtgaagggca agcacctgtg ccccagccct ctgttccccg gccctagcaa acccttctgg    540

gtgctggtgg tcgtgggcgg cgtcctggct tgctactccc tgctggtgac cgtggccttt    600

atcatcttct gggtgaggtc caagcgctcc aggctgctgc acagcgatta catgaacatg    660

acccccagga gaccaggccc cacccggaag cactaccagc cctatgcccc cccccgcgac    720

ttcgctgctt atagaagcag agtcaagttc tcccgcagcg ccgacgcccc cgcataccag    780

cagggacaga accagctgta caacgaactg aacctgggcc ggagagagga atacgacgtg    840

ctggataaga gaagaggaag ggaccccgag atgggaggaa aaccaagaag aaagaaccca    900
```

```
caggagggcc tgtacaatga gctgcagaaa gacaagatgg cagaggcata tagcgagatc    960

ggaatgaagg gagagagaag aagaggaaag ggacacgacg gactgtacca gggactgagc   1020

acagctacaa aggacacata cgacgccctg cacatgcagg cactgccacc cagagactat   1080

aaggacgacg acgacaaata a                                             1101


<210> SEQ ID NO 54
<211> LENGTH: 366
<212> TYPE: PRT
<213> ORGANISM: Artificial Sequence
<220> FEATURE:
<223> OTHER INFORMATION: HER2-BBzeta

<400> SEQUENCE: 54

Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Gly Gly Leu
            20                  25                  30

Val Gln Pro Gly Gly Ser Leu Arg Leu Ser Cys Ala Ala Ser Gly Asn
        35                  40                  45

Ser Ala Asn Ile Phe Ser Phe Ala Ser Val Ala Trp Tyr Arg Gln Ala
    50                  55                  60

Pro Gly Lys Gln Arg Glu Leu Val Ala Val Ile Thr Ser Ala Gly Gly
65                  70                  75                  80

Thr Lys Tyr Ser Asp Ser Val Lys Gly Arg Phe Thr Ile Ser Arg Asp
                85                  90                  95

Asn Ala Lys Asn Thr Ile Leu Leu Gln Met Asn Ser Leu Lys Pro Glu
            100                 105                 110

Asp Thr Ala Val Tyr Tyr Cys Asn Val Asp Tyr Leu Gln Asp Tyr Trp
        115                 120                 125

Gly Gln Gly Thr Gln Val Thr Val Ser Ser Ala Ile Glu Val Met Tyr
    130                 135                 140

Pro Pro Pro Tyr Leu Asp Asn Glu Lys Ser Asn Gly Thr Ile Ile His
145                 150                 155                 160

Val Lys Gly Lys His Leu Cys Pro Ser Pro Leu Phe Pro Gly Pro Ser
                165                 170                 175

Lys Pro Phe Trp Val Leu Val Val Val Gly Gly Val Leu Ala Cys Tyr
            180                 185                 190

Ser Leu Leu Val Thr Val Ala Phe Ile Ile Phe Trp Val Arg Ser Lys
        195                 200                 205

Arg Ser Arg Leu Leu His Ser Asp Tyr Met Asn Met Thr Pro Arg Arg
    210                 215                 220

Pro Gly Pro Thr Arg Lys His Tyr Gln Pro Tyr Ala Pro Pro Arg Asp
225                 230                 235                 240

Phe Ala Ala Tyr Arg Ser Arg Val Lys Phe Ser Arg Ser Ala Asp Ala
                245                 250                 255

Pro Ala Tyr Gln Gln Gly Gln Asn Gln Leu Tyr Asn Glu Leu Asn Leu
            260                 265                 270

Gly Arg Arg Glu Glu Tyr Asp Val Leu Asp Lys Arg Arg Gly Arg Asp
        275                 280                 285

Pro Glu Met Gly Gly Lys Pro Arg Arg Lys Asn Pro Gln Glu Gly Leu
    290                 295                 300

Tyr Asn Glu Leu Gln Lys Asp Lys Met Ala Glu Ala Tyr Ser Glu Ile
305                 310                 315                 320

Gly Met Lys Gly Glu Arg Arg Arg Gly Lys Gly His Asp Gly Leu Tyr
```

```
            325                 330                 335

Gln Gly Leu Ser Thr Ala Thr Lys Asp Thr Tyr Asp Ala Leu His Met
        340                 345                 350

Gln Ala Leu Pro Pro Arg Asp Tyr Lys Asp Asp Asp Asp Lys
    355                 360                 365


<210> SEQ ID NO 55
<211> LENGTH: 1485
<212> TYPE: DNA
<213> ORGANISM: Artificial Sequence
<220> FEATURE:
<223> OTHER INFORMATION: HER2-28zeta

<400> SEQUENCE: 55

atggccctgc ccgtgaccgc tctgctgctg cctctggccc tgctgctgca cgccgctaga      60

cccgacatcc agatgaccca gtcccccagc agcctgagcg ccagcgtggg agacagggtg     120

accatcacct gtagagcctc ccaggacgtc aacaccgccg tcgcctggta ccagcagaaa     180

ccaggcaagg cccccaaact gctgatctac tccgccagct tcctgtatag tggcgtgccc     240

tcccgattca gcggcagcag aagcggaacc gacttcaccc tgactatcag cagcctgcag     300

cccgaggatt tcgccaccta ctactgccag cagcactaca ccaccccccc cacattcggc     360

cagggcacaa aggtggaaat caagggctcc acctccggct ccggcaaacc cggatcaggc     420

gaaggctcta ccaaaggcga ggtccagctg gtcgagagcg gcggaggcct ggtgcagcca     480

ggaggaagcc tgagactgag ctgtgccgcc agcggattca atatcaaaga cacctacatc     540

cattgggtga gacaggcacc cggaaaaggg ctggagtggg tggctagaat ctaccccacc     600

aacggataca cccgctacgc cgacagcgtg aagggccgct tcaccatcag cgccgacacc     660

agcaagaaca ccgcctacct gcagatgaac agcctgagag ccgaggacac cgccgtgtac     720

tactgcagca gatggggagg agacggattc tacgccatgg actactgggg acagggcacc     780

ctggtgacag tgagcagcgc catcgaggtg atgtaccctc ccccctacct ggacaacgag     840

aagagcaacg gcaccatcat tcacgtcaag ggaaagcacc tgtgccccag cccccctgttc     900

cccggacctt ccaagccctt ctgggtcctg gtggtggtcg gcggcgtgct ggcttgctac     960

agcctgctgg tgaccgtcgc ctttatcatt ttctgggtga gatccaagag atcccgcctg    1020

ctgcacagcg actacatgaa catgaccccc agaagacccg gccccacccg caagcactac    1080

cagccttatg cccccccccg cgacttcgcc gcttatagaa gcagagtgaa gttctcccgc    1140

agcgccgacg cccccgctta ccagcaggga cagaaccagc tgtacaacga actgaacctg    1200

ggccgcagag aagaatatga cgtgctggat aagagaagag gaagagaccc cgagatggga    1260

ggaaaaccaa gaagaaagaa cccacaggag ggcctgtaca atgagctgca gaaagacaag    1320

atggcagagg catatagcga gatcggaatg aagggagaga gaagaagagg aaagggacac    1380

gacggactgt accagggact gagcacagct acaaaggaca catacgacgc cctgcacatg    1440

caggcactgc cacccagaga ctataaggac gacgacgaca aataa                   1485


<210> SEQ ID NO 56
<211> LENGTH: 494
<212> TYPE: PRT
<213> ORGANISM: Artificial Sequence
<220> FEATURE:
<223> OTHER INFORMATION: HER2-28zeta

<400> SEQUENCE: 56

Met Ala Leu Pro Val Thr Ala Leu Leu Leu Pro Leu Ala Leu Leu Leu
```

-continued 1 5 10 15

His Ala Ala Arg Pro Asp Ile Gln Met Thr Gln Ser Pro Ser Ser Leu
20 25 30

Ser Ala Ser Val Gly Asp Arg Val Thr Ile Thr Cys Arg Ala Ser Gln
35 40 45

Asp Val Asn Thr Ala Val Ala Trp Tyr Gln Gln Lys Pro Gly Lys Ala
50 55 60

Pro Lys Leu Leu Ile Tyr Ser Ala Ser Phe Leu Tyr Ser Gly Val Pro
65 70 75 80

Ser Arg Phe Ser Gly Ser Arg Ser Gly Thr Asp Phe Thr Leu Thr Ile
85 90 95

Ser Ser Leu Gln Pro Glu Asp Phe Ala Thr Tyr Tyr Cys Gln Gln His
100 105 110

Tyr Thr Thr Pro Pro Thr Phe Gly Gln Gly Thr Lys Val Glu Ile Lys
115 120 125

Gly Ser Thr Ser Gly Ser Gly Lys Pro Gly Ser Gly Glu Gly Ser Thr
130 135 140

Lys Gly Glu Val Gln Leu Val Glu Ser Gly Gly Gly Leu Val Gln Pro
145 150 155 160

Gly Gly Ser Leu Arg Leu Ser Cys Ala Ala Ser Gly Phe Asn Ile Lys
165 170 175

Asp Thr Tyr Ile His Trp Val Arg Gln Ala Pro Gly Lys Gly Leu Glu
180 185 190

Trp Val Ala Arg Ile Tyr Pro Thr Asn Gly Tyr Thr Arg Tyr Ala Asp
195 200 205

Ser Val Lys Gly Arg Phe Thr Ile Ser Ala Asp Thr Ser Lys Asn Thr
210 215 220

Ala Tyr Leu Gln Met Asn Ser Leu Arg Ala Glu Asp Thr Ala Val Tyr
225 230 235 240

Tyr Cys Ser Arg Trp Gly Gly Asp Gly Phe Tyr Ala Met Asp Tyr Trp
245 250 255

Gly Gln Gly Thr Leu Val Thr Val Ser Ser Ala Ile Glu Val Met Tyr
260 265 270

Pro Pro Pro Tyr Leu Asp Asn Glu Lys Ser Asn Gly Thr Ile Ile His
275 280 285

Val Lys Gly Lys His Leu Cys Pro Ser Pro Leu Phe Pro Gly Pro Ser
290 295 300

Lys Pro Phe Trp Val Leu Val Val Val Gly Gly Val Leu Ala Cys Tyr
305 310 315 320

Ser Leu Leu Val Thr Val Ala Phe Ile Ile Phe Trp Val Arg Ser Lys
325 330 335

Arg Ser Arg Leu Leu His Ser Asp Tyr Met Asn Met Thr Pro Arg Arg
340 345 350

Pro Gly Pro Thr Arg Lys His Tyr Gln Pro Tyr Ala Pro Pro Arg Asp
355 360 365

Phe Ala Ala Tyr Arg Ser Arg Val Lys Phe Ser Arg Ser Ala Asp Ala
370 375 380

Pro Ala Tyr Gln Gln Gly Gln Asn Gln Leu Tyr Asn Glu Leu Asn Leu
385 390 395 400

Gly Arg Arg Glu Glu Tyr Asp Val Leu Asp Lys Arg Arg Gly Arg Asp
405 410 415

Pro Glu Met Gly Gly Lys Pro Arg Arg Lys Asn Pro Gln Glu Gly Leu
420 425 430

```
Tyr Asn Glu Leu Gln Lys Asp Lys Met Ala Glu Ala Tyr Ser Glu Ile
        435                 440                 445

Gly Met Lys Gly Glu Arg Arg Arg Gly Lys Gly His Asp Gly Leu Tyr
    450                 455                 460

Gln Gly Leu Ser Thr Ala Thr Lys Asp Thr Tyr Asp Ala Leu His Met
465                 470                 475                 480

Gln Ala Leu Pro Pro Arg Asp Tyr Lys Asp Asp Asp Asp Lys
                485                 490
```

<210> SEQ ID NO 57
<211> LENGTH: 120
<212> TYPE: DNA
<213> ORGANISM: Artificial Sequence
<220> FEATURE:
<223> OTHER INFORMATION: CD28 Hinge

<400> SEQUENCE: 57

```
gccatcgagg tgatgtaccc tcccccctac ctggacaacg agaagagcaa cggcaccatc      60

attcacgtca agggaaagca cctgtgcccc agccccctgt tccccggacc ttccaagccc     120
```

<210> SEQ ID NO 58
<211> LENGTH: 40
<212> TYPE: PRT
<213> ORGANISM: Artificial Sequence
<220> FEATURE:
<223> OTHER INFORMATION: CD28 Hinge

<400> SEQUENCE: 58

```
Ala Ile Glu Val Met Tyr Pro Pro Pro Tyr Leu Asp Asn Glu Lys Ser
1               5                   10                  15

Asn Gly Thr Ile Ile His Val Lys Gly Lys His Leu Cys Pro Ser Pro
            20                  25                  30

Leu Phe Pro Gly Pro Ser Lys Pro
        35                  40
```

<210> SEQ ID NO 59
<211> LENGTH: 81
<212> TYPE: DNA
<213> ORGANISM: Artificial Sequence
<220> FEATURE:
<223> OTHER INFORMATION: CD28 TM

<400> SEQUENCE: 59

```
ttctgggtcc tggtggtggt cggcggcgtg ctggcttgct acagcctgct ggtgaccgtc      60

gcctttatca ttttctgggt g                                                81
```

<210> SEQ ID NO 60
<211> LENGTH: 27
<212> TYPE: PRT
<213> ORGANISM: Artificial Sequence
<220> FEATURE:
<223> OTHER INFORMATION: CD28 TM

<400> SEQUENCE: 60

```
Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25
```

<210> SEQ ID NO 61
<211> LENGTH: 123

<212> TYPE: DNA
<213> ORGANISM: Artificial Sequence
<220> FEATURE:
<223> OTHER INFORMATION: CD28 costimulatory domain

<400> SEQUENCE: 61
agatccaaga gatcccgcct gctgcacagc gactacatga acatgacccc cagaagaccc 60
ggccccaccc gcaagcacta ccagccttat gcccccccc gcgacttcgc cgcttataga 120
agc 123

<210> SEQ ID NO 62
<211> LENGTH: 41
<212> TYPE: PRT
<213> ORGANISM: Artificial Sequence
<220> FEATURE:
<223> OTHER INFORMATION: CD28 costimulatory domain

<400> SEQUENCE: 62

Arg Ser Lys Arg Ser Arg Leu Leu His Ser Asp Tyr Met Asn Met Thr
1 5 10 15

Pro Arg Arg Pro Gly Pro Thr Arg Lys His Tyr Gln Pro Tyr Ala Pro
20 25 30

Pro Arg Asp Phe Ala Ala Tyr Arg Ser
35 40

<210> SEQ ID NO 63
<211> LENGTH: 2235
<212> TYPE: DNA
<213> ORGANISM: Artificial Sequence
<220> FEATURE:
<223> OTHER INFORMATION: HER2-BiTA

<400> SEQUENCE: 63
atgctgctgc tggtgacctc cctgctgctg tgcgagctgc cccaccccgc tttcctgctg 60
atccccgaca tccagatgac ccagtccccc tcctccctgt ccgcctccgt gggagaccgc 120
gtgaccatca cctgccgcgc ctcccaggac gtgaacaccg ccgtcgcctg gtaccagcag 180
aagcccggca aagcccccaa actgctgatc tactccgcct cattcctgta tagcggcgtg 240
ccctccagat tctccggcag cagaagcggc accgacttca ccctgactat cagcagcctg 300
cagcccgaag acttcgccac ctactactgc cagcagcact acaccacccc ccccaccttc 360
ggccagggca caaaagtgga gatcaagggc agcaccagcg gcagcggaaa acccggcagc 420
ggcgagggat ctaccaaagg cgaggtccag ctggtggaga gcggcggagg cctggtgcag 480
ccaggaggaa gcctgagact gagctgtgcc gcaagcggat tcaatatcaa ggatacatac 540
attcattggg tgagacaggc acccggaaaa ggcctggagt gggtggctag aatttaccca 600
accaacggat acacccggta cgccgatagc gtgaagggca gattcaccat tagcgccgac 660
accagcaaga acacagccta cctgcagatg aacagcctga gagccgagga caccgcagtg 720
tactactgca gcagatgggg aggggacgga ttctacgcca tggactactg gggacagggc 780
accctggtga cagtgagcag cggcggcggc ggaagcgaca ttaagctgca gcagagtggc 840
gccgagctgg caagacccgg agccagtgtg aagatgagct gcaagactag cggctacacc 900
ttcaccagat atacaatgca ttgggtgaaa cagagacccg gccagggact ggagtggatt 960
ggatacatta accccagcag aggctacacc aactacaacc agaagttcaa ggacaaggca 1020
accctgacca cagacaaaag cagcagcaca gcctacatgc agctgagcag cctgaccagc 1080
gaggacagcg ccgtgtacta ctgtgccaga tactacgacg accactactg cctggactac 1140
tggggccagg gaaccacact gaccgtgtcc agcgtggagg gcggatcagg cggcagcgga 1200
ggaagcggag gaagtggggg cgtggacgac atccagctga cacagagtcc cgctatcatg 1260
agcgcaagtc ccggcgagaa ggtgacaatg acctgcagag ctagctcaag cgtgagctat 1320
atgaattggt accagcagaa aagcggcacc agccccaaaa gatggatcta cgacacctca 1380
aaggtggcca gcggagtgcc ctacagattc agcggatcag gaagcggaac atcatacagc 1440
ctgactatct ccagcatgga ggctgaagac gccgcaacct actactgtca gcagtggagc 1500
tctaaccccc tgaccttcgg cgccggcacc aagctggagc tgaagcacca ccaccaccat 1560
cacggcagcg gcgaaggcag aggcagcctg ctgacctgcg gcgacgtcga ggaaaacccc 1620
ggccccatgc tgctgctggt cacctccctg ctgctgtgcg aactgcccca ccccgccttt 1680
ctgctgattc ctgatggcaa cgaggagatg ggcggcatca cacagacccc ctacaaagtg 1740
tccatctccg gcaccaccgt gatcctgacc tgcccccagt accccggctc cgagatcctg 1800
tggcagcaca acgacaagaa cattggcgga gacgaggacg acaaaaacat cggaagcgac 1860
gaggaccacc tgagcctgaa ggaattcagc gaactggagc agtcaggcta ctacgtctgc 1920
tacccaagag gaagcaaacc agaggacgcc aacttctatc tgtacctgag agccagagtc 1980
tgcgagaact gcatggagat ggacacaacc acccccgccc ccagaccccc taccccctgct 2040 cctaccattg ccagccagcc actgtccctg aggcccgaag cctgcagacc agcagccggc 2100
ggagccgtgc acaccagagg actggacttc gcctgtgaca tctacatctg ggcccccctg 2160
gccgggacct gcggagtgct gctgctgagc ctggtgatta ctctgtactg cgattacaag 2220
gatgatgacg acaaa 2235

<210> SEQ ID NO 64
<211> LENGTH: 745
<212> TYPE: PRT
<213> ORGANISM: Artificial Sequence
<220> FEATURE:
<223> OTHER INFORMATION: HER2-BiTA

<400> SEQUENCE: 64

Met Leu Leu Leu Val Thr Ser Leu Leu Leu Cys Glu Leu Pro His Pro
1 5 10 15

Ala Phe Leu Leu Ile Pro Asp Ile Gln Met Thr Gln Ser Pro Ser Ser
20 25 30

Leu Ser Ala Ser Val Gly Asp Arg Val Thr Ile Thr Cys Arg Ala Ser
35 40 45

Gln Asp Val Asn Thr Ala Val Ala Trp Tyr Gln Gln Lys Pro Gly Lys
50 55 60

Ala Pro Lys Leu Leu Ile Tyr Ser Ala Ser Phe Leu Tyr Ser Gly Val
65 70 75 80

Pro Ser Arg Phe Ser Gly Ser Arg Ser Gly Thr Asp Phe Thr Leu Thr
85 90 95

Ile Ser Ser Leu Gln Pro Glu Asp Phe Ala Thr Tyr Tyr Cys Gln Gln
100 105 110

His Tyr Thr Thr Pro Pro Thr Phe Gly Gln Gly Thr Lys Val Glu Ile
115 120 125

Lys Gly Ser Thr Ser Gly Ser Gly Lys Pro Gly Ser Gly Glu Gly Ser
130 135 140

Thr Lys Gly Glu Val Gln Leu Val Glu Ser Gly Gly Gly Leu Val Gln
145 150 155 160

-continued

```
Pro Gly Gly Ser Leu Arg Leu Ser Cys Ala Ala Ser Gly Phe Asn Ile
                165                 170                 175

Lys Asp Thr Tyr Ile His Trp Val Arg Gln Ala Pro Gly Lys Gly Leu
            180                 185                 190

Glu Trp Val Ala Arg Ile Tyr Pro Thr Asn Gly Tyr Thr Arg Tyr Ala
        195                 200                 205

Asp Ser Val Lys Gly Arg Phe Thr Ile Ser Ala Asp Thr Ser Lys Asn
    210                 215                 220

Thr Ala Tyr Leu Gln Met Asn Ser Leu Arg Ala Glu Asp Thr Ala Val
225                 230                 235                 240

Tyr Tyr Cys Ser Arg Trp Gly Gly Asp Gly Phe Tyr Ala Met Asp Tyr
                245                 250                 255

Trp Gly Gln Gly Thr Leu Val Thr Val Ser Ser Gly Gly Gly Gly Ser
            260                 265                 270

Asp Ile Lys Leu Gln Gln Ser Gly Ala Glu Leu Ala Arg Pro Gly Ala
        275                 280                 285

Ser Val Lys Met Ser Cys Lys Thr Ser Gly Tyr Thr Phe Thr Arg Tyr
    290                 295                 300

Thr Met His Trp Val Lys Gln Arg Pro Gly Gln Gly Leu Glu Trp Ile
305                 310                 315                 320

Gly Tyr Ile Asn Pro Ser Arg Gly Tyr Thr Asn Tyr Asn Gln Lys Phe
                325                 330                 335

Lys Asp Lys Ala Thr Leu Thr Thr Asp Lys Ser Ser Ser Thr Ala Tyr
            340                 345                 350

Met Gln Leu Ser Ser Leu Thr Ser Glu Asp Ser Ala Val Tyr Tyr Cys
        355                 360                 365

Ala Arg Tyr Tyr Asp Asp His Tyr Cys Leu Asp Tyr Trp Gly Gln Gly
    370                 375                 380

Thr Thr Leu Thr Val Ser Ser Val Glu Gly Gly Ser Gly Gly Ser Gly
385                 390                 395                 400

Gly Ser Gly Gly Ser Gly Gly Val Asp Asp Ile Gln Leu Thr Gln Ser
                405                 410                 415

Pro Ala Ile Met Ser Ala Ser Pro Gly Glu Lys Val Thr Met Thr Cys
            420                 425                 430

Arg Ala Ser Ser Ser Val Ser Tyr Met Asn Trp Tyr Gln Gln Lys Ser
        435                 440                 445

Gly Thr Ser Pro Lys Arg Trp Ile Tyr Asp Thr Ser Lys Val Ala Ser
    450                 455                 460

Gly Val Pro Tyr Arg Phe Ser Gly Ser Gly Ser Gly Thr Ser Tyr Ser
465                 470                 475                 480

Leu Thr Ile Ser Ser Met Glu Ala Glu Asp Ala Ala Thr Tyr Tyr Cys
                485                 490                 495

Gln Gln Trp Ser Ser Asn Pro Leu Thr Phe Gly Ala Gly Thr Lys Leu
            500                 505                 510

Glu Leu Lys His His His His His His Gly Ser Gly Glu Gly Arg Gly
        515                 520                 525

Ser Leu Leu Thr Cys Gly Asp Val Glu Glu Asn Pro Gly Pro Met Leu
    530                 535                 540

Leu Leu Val Thr Ser Leu Leu Leu Cys Glu Leu Pro His Pro Ala Phe
545                 550                 555                 560

Leu Leu Ile Pro Asp Gly Asn Glu Glu Met Gly Gly Ile Thr Gln Thr
                565                 570                 575

Pro Tyr Lys Val Ser Ile Ser Gly Thr Thr Val Ile Leu Thr Cys Pro
```

580 585 590

Gln Tyr Pro Gly Ser Glu Ile Leu Trp Gln His Asn Asp Lys Asn Ile
595 600 605

Gly Gly Asp Glu Asp Asp Lys Asn Ile Gly Ser Asp Glu Asp His Leu
610 615 620

Ser Leu Lys Glu Phe Ser Glu Leu Glu Gln Ser Gly Tyr Tyr Val Cys
625 630 635 640

Tyr Pro Arg Gly Ser Lys Pro Glu Asp Ala Asn Phe Tyr Leu Tyr Leu
645 650 655

Arg Ala Arg Val Cys Glu Asn Cys Met Glu Met Asp Thr Thr Thr Pro
660 665 670

Ala Pro Arg Pro Pro Thr Pro Ala Pro Thr Ile Ala Ser Gln Pro Leu
675 680 685

Ser Leu Arg Pro Glu Ala Cys Arg Pro Ala Ala Gly Gly Ala Val His
690 695 700

Thr Arg Gly Leu Asp Phe Ala Cys Asp Ile Tyr Ile Trp Ala Pro Leu
705 710 715 720

Ala Gly Thr Cys Gly Val Leu Leu Leu Ser Leu Val Ile Thr Leu Tyr
725 730 735

Cys Asp Tyr Lys Asp Asp Asp Asp Lys
740 745

<210> SEQ ID NO 65
<211> LENGTH: 735
<212> TYPE: DNA
<213> ORGANISM: Artificial Sequence
<220> FEATURE:
<223> OTHER INFORMATION: Trastuzumab scFv

<400> SEQUENCE: 65
gacatccaga tgacccagag ccccagcagc ctgagcgcca gcgtgggcga ccgcgtgacc 60
atcacctgcc gcgccagcca ggacgtgaac accgccgtgg cctggtacca gcagaagccc 120
ggcaaggccc ccaagctgct gatctacagc gccagcttcc tgtacagcgg cgtgcccagc 180
cgcttcagcg gcagccgcag cggcaccgac ttcaccctga ccatcagcag cctgcagccc 240
gaggacttcg ccacctacta ctgccagcag cactacacca cccccccac cttcggccag 300 ggcaccaagg tggagatcaa gggcagcacc agcggcagcg gcaagcccgg cagcggcgag 360
ggcagcacca agggcgaggt gcagctggtg gagagcggcg gcggcctggt gcagcccggc 420
ggcagcctgc gcctgagctg cgccgccagc ggcttcaaca tcaaggacac ctacatccac 480
tgggtgcgcc aggcccccgg caagggcctg gagtgggtgg cccgcatcta ccccaccaac 540
ggctacaccc gctacgccga cagcgtgaag ggccgcttca ccatcagcgc cgacaccagc 600
aagaacaccg cctacctgca gatgaacagc ctgcgcgccg aggacaccgc cgtgtactac 660
tgcagccgct ggggcggcga cggcttctac gccatggact actggggcca gggcaccctg 720
gtgaccgtga gcagc 735

<210> SEQ ID NO 66
<211> LENGTH: 245
<212> TYPE: PRT
<213> ORGANISM: Artificial Sequence
<220> FEATURE:
<223> OTHER INFORMATION: Trastuzumab scFv

<400> SEQUENCE: 66

Asp Ile Gln Met Thr Gln Ser Pro Ser Ser Leu Ser Ala Ser Val Gly

-continued

```
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Gly Ser Thr Ser Gly
            100                 105                 110

Ser Gly Lys Pro Gly Ser Gly Glu Gly Ser Thr Lys Gly Glu Val Gln
        115                 120                 125

Leu Val Glu Ser Gly Gly Gly Leu Val Gln Pro Gly Gly Ser Leu Arg
    130                 135                 140

Leu Ser Cys Ala Ala Ser Gly Phe Asn Ile Lys Asp Thr Tyr Ile His
145                 150                 155                 160

Trp Val Arg Gln Ala Pro Gly Lys Gly Leu Glu Trp Val Ala Arg Ile
                165                 170                 175

Tyr Pro Thr Asn Gly Tyr Thr Arg Tyr Ala Asp Ser Val Lys Gly Arg
            180                 185                 190

Phe Thr Ile Ser Ala Asp Thr Ser Lys Asn Thr Ala Tyr Leu Gln Met
        195                 200                 205

Asn Ser Leu Arg Ala Glu Asp Thr Ala Val Tyr Tyr Cys Ser Arg Trp
    210                 215                 220

Gly Gly Asp Gly Phe Tyr Ala Met Asp Tyr Trp Gly Gln Gly Thr Leu
225                 230                 235                 240

Val Thr Val Ser Ser
                245
```

<210> SEQ ID NO 67
<211> LENGTH: 2700
<212> TYPE: DNA
<213> ORGANISM: Artificial Sequence
<220> FEATURE:
<223> OTHER INFORMATION: HER2-CABR

<400> SEQUENCE: 67

```
atgctgctgc tggtgacctc cctgctgctg tgcgagctgc cccaccccgc tttcctgctg      60

atccccgaca tccagatgac ccagtccccc tcctccctgt ccgcctccgt gggagaccgc     120

gtgaccatca cctgccgcgc ctcccaggac gtgaacaccg ccgtcgcctg gtaccagcag     180

aagcccggca aagcccccaa actgctgatc tactccgcct cattcctgta tagcggcgtg     240

ccctccagat tctccggcag cagaagcggc accgacttca ccctgactat cagcagcctg     300

cagcccgaag acttcgccac ctactactgc cagcagcact acaccacccc ccccaccttc     360

ggccagggca caaaagtgga gatcaagggc agcaccagcg gcagcggaaa acccggcagc     420

ggcgagggat ctaccaaagg cgaggtccag ctggtggaga gcggcggagg cctggtgcag     480

ccaggaggaa gcctgagact gagctgtgcc gcaagcggat tcaatatcaa ggatacatac     540

attcattggg tgagacaggc acccggaaaa ggcctggagt gggtggctag aatttaccca     600

accaacggat acacccggta cgccgatagc gtgaagggca gattcaccat tagcgccgac     660
```

accagcaaga acacagccta cctgcagatg aacagcctga gagccgagga caccgcagtg 720
tactactgca gcagatgggg aggggacgga ttctacgcca tggactactg gggacagggc 780
accctggtga cagtgagcag cggcggcggc ggaagcgaca ttaagctgca gcagagtggc 840
gccgagctgg caagacccgg agccagtgtg aagatgagct gcaagactag cggctacacc 900
ttcaccagat atacaatgca ttgggtgaaa cagagacccg gccagggact ggagtggatt 960
ggatacatta accccagcag aggctacacc aactacaacc agaagttcaa ggacaaggca 1020
accctgacca cagacaaaag cagcagcaca gcctacatgc agctgagcag cctgaccagc 1080
gaggacagcg ccgtgtacta ctgtgccaga tactacgacg accactactg cctggactac 1140
tggggccagg gaaccacact gaccgtgtcc agcgtggagg gcggatcagg cggcagcgga 1200
ggaagcggag gaagtggggg cgtggacgac atccagctga cacagagtcc cgctatcatg 1260
agcgcaagtc ccggcgagaa ggtgacaatg acctgcagag ctagctcaag cgtgagctat 1320
atgaattggt accagcagaa aagcggcacc agccccaaaa gatggatcta cgacacctca 1380
aaggtggcca gcggagtgcc ctacagattc agcggatcag gaagcggaac atcatacagc 1440
ctgactatct ccagcatgga ggctgaagac gccgcaacct actactgtca gcagtggagc 1500
tctaaccccc tgaccttcgg cgccggcacc aagctggagc tgaagcacca ccaccaccat 1560
cacggatctg gggaggggag aggaagcctg ctgacatgtg gagacgtgga ggagaaccct 1620
gggcctatgc tgctgctggt gaccagcctg ctgctgtgtg agctgcctca cccagctttt 1680
ctgctgattc ccgatggaaa tgaagaaatg ggaggaatta cccagacccc ttacaaagtg 1740
agcatctccg gcactaccgt gatcctgacc tgcccccagt accccggcag cgagatcctg 1800
tggcagcaca acgacaagaa catcggcgga gacgaggacg acaaaaacat cggcagcgac 1860
gaggaccacc tgagcctgaa ggaatttagc gaactggagc agagcggata ctacgtgtgc 1920
taccccagag gaagcaaacc agaggacgca aacttctacc tgtacctgag agccagagtc 1980
tgcgagaact gcatggagat ggacacaacc acccccgcac caagaccccc cacccctgct 2040
ccaaccattg ccagccagcc cctgtccctg agacccgagg cctgcagacc agccgccgga 2100
ggagcagtgc acacaagagg actggacttc gcctgtgaca tctacatctg ggccccccctg 2160
gccgggacct gcggagtgct gctgctgtcc ctggtgatta ctctgtactg taagagagga 2220
aggaagaaac tgctgtacat cttcaagcag ccttttatgc ggcccgtgca gaccacccag 2280
gaggaggatg gatgttcctg tagatttcct gaggaggagg agggcgggtg cgagctgaga 2340
gtgaagtttt ccaggagcgc cgacgccccc gcctaccagc agggacagaa tcagctgtat 2400
aacgagctga acctgggcag acgggaagag tatgacgtgc tggataagag aagaggaaga 2460
gacccagaga tgggaggaaa gccaagaaga aagaaccccc aggagggcct gtacaacgag 2520
ctgcagaaag acaagatggc agaggcatac agcgagatcg gaatgaaggg agagagaaga 2580
agaggaaagg gacacgacgg actgtaccag ggcctgagca cagctacaaa ggacacatac 2640
gacgccctgc acatgcaggc cctgcccccca agagactaca aggacgacga cgacaagtaa 2700

<210> SEQ ID NO 68
<211> LENGTH: 899
<212> TYPE: PRT
<213> ORGANISM: Artificial Sequence
<220> FEATURE:
<223> OTHER INFORMATION: HER2-CABR

<400> SEQUENCE: 68

Met Leu Leu Leu Val Thr Ser Leu Leu Leu Cys Glu Leu Pro His Pro

-continued

```
1               5                   10                  15

Ala Phe Leu Leu Ile Pro Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Asp Val Asn Thr Ala Val Ala Trp Tyr Gln Gln Lys Pro Gly Lys
    50                  55                  60

Ala Pro Lys Leu Leu Ile Tyr Ser Ala Ser Phe Leu Tyr Ser Gly Val
65                  70                  75                  80

Pro Ser Arg Phe Ser Gly Ser Arg Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

His Tyr Thr Thr Pro Pro Thr Phe Gly Gln Gly Thr Lys Val Glu Ile
        115                 120                 125

Lys Gly Ser Thr Ser Gly Ser Gly Lys Pro Gly Ser Gly Glu Gly Ser
    130                 135                 140

Thr Lys Gly Glu Val Gln Leu Val Glu Ser Gly Gly Gly Leu Val Gln
145                 150                 155                 160

Pro Gly Gly Ser Leu Arg Leu Ser Cys Ala Ala Ser Gly Phe Asn Ile
                165                 170                 175

Lys Asp Thr Tyr Ile His Trp Val Arg Gln Ala Pro Gly Lys Gly Leu
            180                 185                 190

Glu Trp Val Ala Arg Ile Tyr Pro Thr Asn Gly Tyr Thr Arg Tyr Ala
        195                 200                 205

Asp Ser Val Lys Gly Arg Phe Thr Ile Ser Ala Asp Thr Ser Lys Asn
    210                 215                 220

Thr Ala Tyr Leu Gln Met Asn Ser Leu Arg Ala Glu Asp Thr Ala Val
225                 230                 235                 240

Tyr Tyr Cys Ser Arg Trp Gly Gly Asp Gly Phe Tyr Ala Met Asp Tyr
                245                 250                 255

Trp Gly Gln Gly Thr Leu Val Thr Val Ser Ser Gly Gly Gly Gly Ser
            260                 265                 270

Asp Ile Lys Leu Gln Gln Ser Gly Ala Glu Leu Ala Arg Pro Gly Ala
        275                 280                 285

Ser Val Lys Met Ser Cys Lys Thr Ser Gly Tyr Thr Phe Thr Arg Tyr
    290                 295                 300

Thr Met His Trp Val Lys Gln Arg Pro Gly Gln Gly Leu Glu Trp Ile
305                 310                 315                 320

Gly Tyr Ile Asn Pro Ser Arg Gly Tyr Thr Asn Tyr Asn Gln Lys Phe
                325                 330                 335

Lys Asp Lys Ala Thr Leu Thr Thr Asp Lys Ser Ser Ser Thr Ala Tyr
            340                 345                 350

Met Gln Leu Ser Ser Leu Thr Ser Glu Asp Ser Ala Val Tyr Tyr Cys
        355                 360                 365

Ala Arg Tyr Tyr Asp Asp His Tyr Cys Leu Asp Tyr Trp Gly Gln Gly
    370                 375                 380

Thr Thr Leu Thr Val Ser Ser Val Glu Gly Gly Ser Gly Gly Ser Gly
385                 390                 395                 400

Gly Ser Gly Gly Ser Gly Gly Val Asp Asp Ile Gln Leu Thr Gln Ser
                405                 410                 415

Pro Ala Ile Met Ser Ala Ser Pro Gly Glu Lys Val Thr Met Thr Cys
            420                 425                 430
```

```
Arg Ala Ser Ser Ser Val Ser Tyr Met Asn Trp Tyr Gln Gln Lys Ser
        435                 440                 445

Gly Thr Ser Pro Lys Arg Trp Ile Tyr Asp Thr Ser Lys Val Ala Ser
    450                 455                 460

Gly Val Pro Tyr Arg Phe Ser Gly Ser Gly Ser Gly Thr Ser Tyr Ser
465                 470                 475                 480

Leu Thr Ile Ser Ser Met Glu Ala Glu Asp Ala Ala Thr Tyr Tyr Cys
                485                 490                 495

Gln Gln Trp Ser Ser Asn Pro Leu Thr Phe Gly Ala Gly Thr Lys Leu
            500                 505                 510

Glu Leu Lys His His His His His His Gly Ser Gly Glu Gly Arg Gly
        515                 520                 525

Ser Leu Leu Thr Cys Gly Asp Val Glu Glu Asn Pro Gly Pro Met Leu
    530                 535                 540

Leu Leu Val Thr Ser Leu Leu Leu Cys Glu Leu Pro His Pro Ala Phe
545                 550                 555                 560

Leu Leu Ile Pro Asp Gly Asn Glu Glu Met Gly Gly Ile Thr Gln Thr
                565                 570                 575

Pro Tyr Lys Val Ser Ile Ser Gly Thr Thr Val Ile Leu Thr Cys Pro
            580                 585                 590

Gln Tyr Pro Gly Ser Glu Ile Leu Trp Gln His Asn Asp Lys Asn Ile
        595                 600                 605

Gly Gly Asp Glu Asp Asp Lys Asn Ile Gly Ser Asp Glu Asp His Leu
    610                 615                 620

Ser Leu Lys Glu Phe Ser Glu Leu Glu Gln Ser Gly Tyr Tyr Val Cys
625                 630                 635                 640

Tyr Pro Arg Gly Ser Lys Pro Glu Asp Ala Asn Phe Tyr Leu Tyr Leu
                645                 650                 655

Arg Ala Arg Val Cys Glu Asn Cys Met Glu Met Asp Thr Thr Thr Pro
            660                 665                 670

Ala Pro Arg Pro Pro Thr Pro Ala Pro Thr Ile Ala Ser Gln Pro Leu
        675                 680                 685

Ser Leu Arg Pro Glu Ala Cys Arg Pro Ala Ala Gly Gly Ala Val His
    690                 695                 700

Thr Arg Gly Leu Asp Phe Ala Cys Asp Ile Tyr Ile Trp Ala Pro Leu
705                 710                 715                 720

Ala Gly Thr Cys Gly Val Leu Leu Leu Ser Leu Val Ile Thr Leu Tyr
                725                 730                 735

Cys Lys Arg Gly Arg Lys Lys Leu Leu Tyr Ile Phe Lys Gln Pro Phe
            740                 745                 750

Met Arg Pro Val Gln Thr Thr Gln Glu Glu Asp Gly Cys Ser Cys Arg
        755                 760                 765

Phe Pro Glu Glu Glu Glu Gly Gly Cys Glu Leu Arg Val Lys Phe Ser
    770                 775                 780

Arg Ser Ala Asp Ala Pro Ala Tyr Gln Gln Gly Gln Asn Gln Leu Tyr
785                 790                 795                 800

Asn Glu Leu Asn Leu Gly Arg Arg Glu Glu Tyr Asp Val Leu Asp Lys
                805                 810                 815

Arg Arg Gly Arg Asp Pro Glu Met Gly Gly Lys Pro Arg Arg Lys Asn
            820                 825                 830

Pro Gln Glu Gly Leu Tyr Asn Glu Leu Gln Lys Asp Lys Met Ala Glu
        835                 840                 845
```

```
Ala Tyr Ser Glu Ile Gly Met Lys Gly Glu Arg Arg Arg Gly Lys Gly
    850                 855                 860

His Asp Gly Leu Tyr Gln Gly Leu Ser Thr Ala Thr Lys Asp Thr Tyr
865                 870                 875                 880

Asp Ala Leu His Met Gln Ala Leu Pro Pro Arg Asp Tyr Lys Asp Asp
                885                 890                 895

Asp Asp Lys
```

<210> SEQ ID NO 69
<211> LENGTH: 351
<212> TYPE: DNA
<213> ORGANISM: Artificial Sequence
<220> FEATURE:
<223> OTHER INFORMATION: Humanized CAIX VHH

<400> SEQUENCE: 69

```
caggtgcagc tggtggagtc cggcggaggc ctggtgcagc ctggaggaag cctgagactg     60

agctgtagcg cctccggcaa cagcgccaat atcttctcct ttgcttccgt ggcctggtat    120

aggcaggccc ccgggaaggg cctggagctg gtgtcagtca ttacatccgc cggcggcacc    180

aagtacagcg acagcgtgaa aggccggttc accatcagca gagacaatag caagaacaca    240

ctgtacctgc agatgaatag cctgagagcc gaggacaccg ccgtgtatta ctgcaacgtg    300

gactacctgc aggactactg gggccagggc accctggtga ccgtgagcag c             351
```

<210> SEQ ID NO 70
<211> LENGTH: 117
<212> TYPE: PRT
<213> ORGANISM: Artificial Sequence
<220> FEATURE:
<223> OTHER INFORMATION: Humanized CAIX VHH

<400> SEQUENCE: 70

```
Gln Val Gln Leu Val Glu Ser Gly Gly Gly Leu Val Gln Pro Gly Gly
1               5                   10                  15

Ser Leu Arg Leu Ser Cys Ser Ala Ser Gly Asn Ser Ala Asn Ile Phe
            20                  25                  30

Ser Phe Ala Ser Val Ala Trp Tyr Arg Gln Ala Pro Gly Lys Gly Leu
        35                  40                  45

Glu Leu Val Ser Val Ile Thr Ser Ala Gly Gly Thr Lys Tyr Ser Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Asn Val Asp Tyr Leu Gln Asp Tyr Trp Gly Gln Gly Thr Leu
            100                 105                 110

Val Thr Val Ser Ser
        115
```

<210> SEQ ID NO 71
<211> LENGTH: 1881
<212> TYPE: DNA
<213> ORGANISM: Artificial Sequence
<220> FEATURE:
<223> OTHER INFORMATION: hCAIX-BiTA

<400> SEQUENCE: 71

```
atgctgctgc tggtgacctc cctgctgctg tgcgagctgc cccaccccgc tttcctgctg     60
```

```
atcccccagg tgcagctggt ggagtccggc ggaggcctgg tgcagcctgg aggaagcctg    120

agactgagct gtagcgcctc cggcaacagc gccaatatct tctcctttgc ttccgtggcc    180

tggtataggc aggcccccgg gaagggcctg gagctggtgt cagtcattac atccgccggc    240

ggcaccaagt acagcgacag cgtgaaaggc cggttcacca tcagcagaga caatagcaag    300

aacacactgt acctgcagat gaatagcctg agagccgagg acaccgccgt gtattactgc    360

aacgtggact acctgcagga ctactggggc cagggcaccc tggtgaccgt gagcagcggc    420

ggaggcggaa gcgacatcaa gctgcagcag tccggagccg aactggctag gcccggcgca    480

agtgtgaaga tgagctgcaa gacctcaggc tacacattta ccagatatac aatgcattgg    540

gtgaagcaga gacccggcca gggactggag tggattggat acattaaccc cagcagaggc    600

tataccaact acaaccagaa attcaaagac aaggccaccc tgaccacaga caaaagcagc    660

agcaccgcat atatgcagct gagcagcctg acaagcgagg acagcgccgt gtactactgc    720

gccagatact acgacgacca ctactgcctg gactactggg gacagggaac cacactgacc    780

gtgagtagcg tggagggcgg atcaggcggc agcggaggaa gcggaggaag tggggggtg    840

gacgacatcc agctgacaca gagccccgcc atcatgagcg caagccccgg cgagaaggtg    900

accatgacct gcagagctag ctcaagcgtg agctacatga actggtacca gcagaagagc    960

ggcaccagcc caaaaagatg gatctatgac accagcaagg tggccagcgg agtgccctac   1020

agattcagcg ggagcggctc cggaacctca tactccctga ctatcagcag catggaagct   1080

gaagacgcag ccacatacta ctgccagcag tggagctcta acccccctgac attcggcgca   1140

ggcaccaagc tggaactgaa gcaccaccac caccatcacg gcagcggcga aggaagaggc   1200

agcctgctga cctgcggcga cgtggaagag aaccccggcc ccatgctgct cctcgtcacc   1260

agcctcctcc tctgcgaact cccccacccc gccttcctgc tgattcccgc ttgccaccag   1320

ctgtgcgccc ggggacactg ctggggacca ggacctaccc agtgcgtgaa ctgcagccag   1380

ttcctccgcg gtcaggaatg cgtcgaagaa tgccgggttc tgcagggact gcccagagaa   1440

tacgttaacg ccagacactg cctgccctgc caccccgaat gtcagcccca gaacggctcc   1500

gtcacctgtt tcggccccga ggcagaccaa tgcgtggcct gcgctcacta caaggacccc   1560

cccttctgcg tggcccgttg cccttccggc gtgaagcccg acctctccta catgcccatt   1620

tggaagttcc ccgatgagga aggcgcctgc cagccctgtc ccatcaactg cacccactcc   1680

tgcgttgacc tggacgacaa gggctgtccc gccgaacaga gagccagccc cctcacctct   1740

atcatctccg ccgtggtggg cattctgctg gtcgtggtcc tgggcgttgt gttcggcatc   1800

ctgatcaaaa gaagacaaca aaagatcaga aagtacacca tgcggcgcct cctggactac   1860

aaggacgatg atgataagta a                                             1881
```

```
<210> SEQ ID NO 72
<211> LENGTH: 626
<212> TYPE: PRT
<213> ORGANISM: Artificial Sequence
<220> FEATURE:
<223> OTHER INFORMATION: hCAIX-BiTA

<400> SEQUENCE: 72

Met Leu Leu Leu Val Thr Ser Leu Leu Leu Cys Glu Leu Pro His Pro
1               5                   10                  15

Ala Phe Leu Leu Ile Pro Gln Val Gln Leu Val Glu Ser Gly Gly Gly
            20                  25                  30

Leu Val Gln Pro Gly Gly Ser Leu Arg Leu Ser Cys Ser Ala Ser Gly
```

```
        35                  40                  45

Asn Ser Ala Asn Ile Phe Ser Phe Ala Ser Val Ala Trp Tyr Arg Gln
    50                  55                  60

Ala Pro Gly Lys Gly Leu Glu Leu Val Ser Val Ile Thr Ser Ala Gly
65                  70                  75                  80

Gly Thr Lys Tyr Ser Asp Ser Val Lys Gly Arg Phe Thr Ile Ser Arg
                85                  90                  95

Asp Asn Ser Lys Asn Thr Leu Tyr Leu Gln Met Asn Ser Leu Arg Ala
            100                 105                 110

Glu Asp Thr Ala Val Tyr Tyr Cys Asn Val Asp Tyr Leu Gln Asp Tyr
        115                 120                 125

Trp Gly Gln Gly Thr Leu Val Thr Val Ser Ser Gly Gly Gly Gly Ser
    130                 135                 140

Asp Ile Lys Leu Gln Gln Ser Gly Ala Glu Leu Ala Arg Pro Gly Ala
145                 150                 155                 160

Ser Val Lys Met Ser Cys Lys Thr Ser Gly Tyr Thr Phe Thr Arg Tyr
                165                 170                 175

Thr Met His Trp Val Lys Gln Arg Pro Gly Gln Gly Leu Glu Trp Ile
            180                 185                 190

Gly Tyr Ile Asn Pro Ser Arg Gly Tyr Thr Asn Tyr Asn Gln Lys Phe
        195                 200                 205

Lys Asp Lys Ala Thr Leu Thr Thr Asp Lys Ser Ser Ser Thr Ala Tyr
    210                 215                 220

Met Gln Leu Ser Ser Leu Thr Ser Glu Asp Ser Ala Val Tyr Tyr Cys
225                 230                 235                 240

Ala Arg Tyr Tyr Asp Asp His Tyr Cys Leu Asp Tyr Trp Gly Gln Gly
                245                 250                 255

Thr Thr Leu Thr Val Ser Ser Val Glu Gly Gly Ser Gly Gly Ser Gly
            260                 265                 270

Gly Ser Gly Gly Ser Gly Gly Val Asp Asp Ile Gln Leu Thr Gln Ser
        275                 280                 285

Pro Ala Ile Met Ser Ala Ser Pro Gly Glu Lys Val Thr Met Thr Cys
    290                 295                 300

Arg Ala Ser Ser Ser Val Ser Tyr Met Asn Trp Tyr Gln Gln Lys Ser
305                 310                 315                 320

Gly Thr Ser Pro Lys Arg Trp Ile Tyr Asp Thr Ser Lys Val Ala Ser
                325                 330                 335

Gly Val Pro Tyr Arg Phe Ser Gly Ser Gly Ser Gly Thr Ser Tyr Ser
            340                 345                 350

Leu Thr Ile Ser Ser Met Glu Ala Glu Asp Ala Ala Thr Tyr Tyr Cys
        355                 360                 365

Gln Gln Trp Ser Ser Asn Pro Leu Thr Phe Gly Ala Gly Thr Lys Leu
    370                 375                 380

Glu Leu Lys His His His His His His Gly Ser Gly Glu Gly Arg Gly
385                 390                 395                 400

Ser Leu Leu Thr Cys Gly Asp Val Glu Glu Asn Pro Gly Pro Met Leu
                405                 410                 415

Leu Leu Val Thr Ser Leu Leu Leu Cys Glu Leu Pro His Pro Ala Phe
            420                 425                 430

Leu Leu Ile Pro Ala Cys His Gln Leu Cys Ala Arg Gly His Cys Trp
        435                 440                 445

Gly Pro Gly Pro Thr Gln Cys Val Asn Cys Ser Gln Phe Leu Arg Gly
    450                 455                 460
```

```
Gln Glu Cys Val Glu Glu Cys Arg Val Leu Gln Gly Leu Pro Arg Glu
465                 470                 475                 480

Tyr Val Asn Ala Arg His Cys Leu Pro Cys His Pro Glu Cys Gln Pro
                485                 490                 495

Gln Asn Gly Ser Val Thr Cys Phe Gly Pro Glu Ala Asp Gln Cys Val
            500                 505                 510

Ala Cys Ala His Tyr Lys Asp Pro Pro Phe Cys Val Ala Arg Cys Pro
        515                 520                 525

Ser Gly Val Lys Pro Asp Leu Ser Tyr Met Pro Ile Trp Lys Phe Pro
    530                 535                 540

Asp Glu Glu Gly Ala Cys Gln Pro Cys Pro Ile Asn Cys Thr His Ser
545                 550                 555                 560

Cys Val Asp Leu Asp Asp Lys Gly Cys Pro Ala Glu Gln Arg Ala Ser
                565                 570                 575

Pro Leu Thr Ser Ile Ile Ser Ala Val Val Gly Ile Leu Leu Val Val
            580                 585                 590

Val Leu Gly Val Val Phe Gly Ile Leu Ile Lys Arg Arg Gln Gln Lys
        595                 600                 605

Ile Arg Lys Tyr Thr Met Arg Arg Leu Leu Asp Tyr Lys Asp Asp Asp
    610                 615                 620

Asp Lys
625


<210> SEQ ID NO 73
<211> LENGTH: 2316
<212> TYPE: DNA
<213> ORGANISM: Artificial Sequence
<220> FEATURE:
<223> OTHER INFORMATION: hCAIX-CAB

<400> SEQUENCE: 73

atgctgctgc tggtgacctc cctgctgctg tgcgagctgc cccaccccgc tttcctgctg     60

atccccgacg gcaacgagga gatgggcggc atcacccaga ccccctacaa ggtgtccatc    120

tccggcacca ccgtgatcct gacctgccct cagtaccccg gctccgagat cctgtggcag    180

cacaacgata agaacatcgg cggagacgag gacgacaaga acatcggaag tgacgaggac    240

cacctgagcc tgaaggaatt cagcgaactg gagcagagcg gctattacgt ctgctacccc    300

agaggaagca aaccagagga cgccaacttc tatctgtacc tgagagccag agtgtgcgag    360

aactgcatgg aaatggacac aaccaccccc gcccccagac cccaacccc  tgctcctacc    420

attgccagcc agccactgtc cctgaggccc gaagcctgca gaccagcagc cggcggagcc    480

gtgcacacca gaggactgga cttcgcctgc gacatctaca tctgggcccc cctggccggg    540

acctgcggag tgctgctgct gagcctggtg attactctgt actgtaagag gggaagaaag    600

aaactgctgt atatcttcaa gcagcccttt atgagacccg tgcagaccac ccaggaggag    660

gacggctgct cctgtagatt ccccgaggag gaggagggcg gctgcgagct gagagtgaag    720

ttctccagga gcgccgacgc ccccgcctac cagcagggac agaaccagct gtacaacgag    780

ctgaacctgg gcagaagaga ggagtatgac gtgctggaca agagaagagg aagagacccc    840

gagatgggag gaaagccaag aagaaagaac ccccaggagg gcctgtacaa tgagctgcag    900

aaggacaaga tggcagaggc atatagcgag atcggaatga agggagagag aagaagagga    960

aagggacacg acggactgta ccagggcctg agcacagcta caaaggacac atacgacgca   1020

ctgcacatgc aggcactgcc accaagagac tacaaggacg atgacgacaa gggatctggg   1080
```

```
gaggggagag gaagcctgct gacatgtgga gacgtggagg agaaccctgg gcctatgctg   1140

ctgctggtga ccagcctgct gctgtgtgag ctgcctcacc cagcttttct gctgattccc   1200

caggtgcagc tggtggagag cggaggcggc ctggtgcagc ctggaggatc tctgagactg   1260

agctgtagcg cctccggcaa ctctgctaac atcttcagct ttgcctccgt ggcctggtac   1320

aggcaggccc ctggaaaagg actggagctg gtgagcgtga tcacctccgc cgggggcacc   1380

aagtactccg acagcgtgaa gggaagattc acaatctcta gagataacag caagaacacc   1440

ctgtacctgc agatgaatag cctgagagcc gaagataccg cagtgtacta ctgcaacgtg   1500

gactacctgc aggactactg gggccaggga accctggtga ccgtgagcag cggaggcgga   1560

ggcagcgaca tcaaactgca gcagagtgga gccgagctgg ccagacccgg ggcaagtgtg   1620

aagatgagct gcaagaccag cggctacacc ttcaccagat acacaatgca ctgggtgaaa   1680

cagagaccag gccagggact ggagtggatt ggatacatta accctagtag aggctacacc   1740

aactacaacc agaaattcaa ggacaaggca acactgacca cagacaaaag cagcagcacc   1800

gcctacatgc agctgagcag cctgaccagc gaagacagcg ccgtgtacta ctgtgccaga   1860

tactacgacg accactactg cctggactac tggggacagg gaaccaccct gaccgtgtcc   1920

agcgtggagg gcggatcagg cggcagcgga ggaagcggag gaagtggggg ggtggacgac   1980

atccagctga cacagagtcc cgccatcatg agcgcaagcc ccggcgagaa ggtgacaatg   2040

acctgcagag ctagctcaag cgtgagctac atgaactggt accagcagaa gagcggcacc   2100

agccccaaaa gatggatcta cgacaccagc aaggtggcca gcggcgtgcc ctacagattc   2160

agcgggagcg gctccggaac ctcctactcc ctgactatca gcagcatgga ggccgaagac   2220

gccgcaacat actactgcca gcagtggagc tctaatccac tgacattcgg cgcaggcacc   2280

aagctggagc tgaagcacca ccaccaccat cactaa                             2316
```

<210> SEQ ID NO 74
<211> LENGTH: 771
<212> TYPE: PRT
<213> ORGANISM: Artificial Sequence
<220> FEATURE:
<223> OTHER INFORMATION: hCAIX-CAB

<400> SEQUENCE: 74

```
Met Leu Leu Leu Val Thr Ser Leu Leu Leu Cys Glu Leu Pro His Pro
1               5                   10                  15

Ala Phe Leu Leu Ile Pro Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
    50                  55                  60

Asn Ile Gly Gly Asp Glu Asp Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp Thr Thr
        115                 120                 125

Thr Pro Ala Pro Arg Pro Pro Thr Pro Ala Pro Thr Ile Ala Ser Gln
    130                 135                 140
```

```
Pro Leu Ser Leu Arg Pro Glu Ala Cys Arg Pro Ala Ala Gly Gly Ala
145                 150                 155                 160

Val His Thr Arg Gly Leu Asp Phe Ala Cys Asp Ile Tyr Ile Trp Ala
                165                 170                 175

Pro Leu Ala Gly Thr Cys Gly Val Leu Leu Leu Ser Leu Val Ile Thr
            180                 185                 190

Leu Tyr Cys Lys Arg Gly Arg Lys Lys Leu Leu Tyr Ile Phe Lys Gln
        195                 200                 205

Pro Phe Met Arg Pro Val Gln Thr Thr Gln Glu Glu Asp Gly Cys Ser
    210                 215                 220

Cys Arg Phe Pro Glu Glu Glu Glu Gly Gly Cys Glu Leu Arg Val Lys
225                 230                 235                 240

Phe Ser Arg Ser Ala Asp Ala Pro Ala Tyr Gln Gln Gly Gln Asn Gln
                245                 250                 255

Leu Tyr Asn Glu Leu Asn Leu Gly Arg Arg Glu Glu Tyr Asp Val Leu
            260                 265                 270

Asp Lys Arg Arg Gly Arg Asp Pro Glu Met Gly Gly Lys Pro Arg Arg
        275                 280                 285

Lys Asn Pro Gln Glu Gly Leu Tyr Asn Glu Leu Gln Lys Asp Lys Met
    290                 295                 300

Ala Glu Ala Tyr Ser Glu Ile Gly Met Lys Gly Glu Arg Arg Arg Gly
305                 310                 315                 320

Lys Gly His Asp Gly Leu Tyr Gln Gly Leu Ser Thr Ala Thr Lys Asp
                325                 330                 335

Thr Tyr Asp Ala Leu His Met Gln Ala Leu Pro Pro Arg Asp Tyr Lys
            340                 345                 350

Asp Asp Asp Asp Lys Gly Ser Gly Glu Gly Arg Gly Ser Leu Leu Thr
        355                 360                 365

Cys Gly Asp Val Glu Glu Asn Pro Gly Pro Met Leu Leu Leu Val Thr
    370                 375                 380

Ser Leu Leu Leu Cys Glu Leu Pro His Pro Ala Phe Leu Leu Ile Pro
385                 390                 395                 400

Gln Val Gln Leu Val Glu Ser Gly Gly Gly Leu Val Gln Pro Gly Gly
                405                 410                 415

Ser Leu Arg Leu Ser Cys Ser Ala Ser Gly Asn Ser Ala Asn Ile Phe
            420                 425                 430

Ser Phe Ala Ser Val Ala Trp Tyr Arg Gln Ala Pro Gly Lys Gly Leu
        435                 440                 445

Glu Leu Val Ser Val Ile Thr Ser Ala Gly Gly Thr Lys Tyr Ser Asp
    450                 455                 460

Ser Val Lys Gly Arg Phe Thr Ile Ser Arg Asp Asn Ser Lys Asn Thr
465                 470                 475                 480

Leu Tyr Leu Gln Met Asn Ser Leu Arg Ala Glu Asp Thr Ala Val Tyr
                485                 490                 495

Tyr Cys Asn Val Asp Tyr Leu Gln Asp Tyr Trp Gly Gln Gly Thr Leu
            500                 505                 510

Val Thr Val Ser Ser Gly Gly Gly Gly Ser Asp Ile Lys Leu Gln Gln
        515                 520                 525

Ser Gly Ala Glu Leu Ala Arg Pro Gly Ala Ser Val Lys Met Ser Cys
    530                 535                 540

Lys Thr Ser Gly Tyr Thr Phe Thr Arg Tyr Thr Met His Trp Val Lys
545                 550                 555                 560
```

```
Gln Arg Pro Gly Gln Gly Leu Glu Trp Ile Gly Tyr Ile Asn Pro Ser
                565                 570                 575

Arg Gly Tyr Thr Asn Tyr Asn Gln Lys Phe Lys Asp Lys Ala Thr Leu
            580                 585                 590

Thr Thr Asp Lys Ser Ser Ser Thr Ala Tyr Met Gln Leu Ser Ser Leu
        595                 600                 605

Thr Ser Glu Asp Ser Ala Val Tyr Tyr Cys Ala Arg Tyr Tyr Asp Asp
    610                 615                 620

His Tyr Cys Leu Asp Tyr Trp Gly Gln Gly Thr Thr Leu Thr Val Ser
625                 630                 635                 640

Ser Val Glu Gly Gly Ser Gly Gly Ser Gly Gly Ser Gly Gly Ser Gly
                645                 650                 655

Gly Val Asp Asp Ile Gln Leu Thr Gln Ser Pro Ala Ile Met Ser Ala
            660                 665                 670

Ser Pro Gly Glu Lys Val Thr Met Thr Cys Arg Ala Ser Ser Ser Val
        675                 680                 685

Ser Tyr Met Asn Trp Tyr Gln Gln Lys Ser Gly Thr Ser Pro Lys Arg
    690                 695                 700

Trp Ile Tyr Asp Thr Ser Lys Val Ala Ser Gly Val Pro Tyr Arg Phe
705                 710                 715                 720

Ser Gly Ser Gly Ser Gly Thr Ser Tyr Ser Leu Thr Ile Ser Ser Met
                725                 730                 735

Glu Ala Glu Asp Ala Ala Thr Tyr Tyr Cys Gln Gln Trp Ser Ser Asn
            740                 745                 750

Pro Leu Thr Phe Gly Ala Gly Thr Lys Leu Glu Leu Lys His His His
        755                 760                 765

His His His
    770
```

<210> SEQ ID NO 75
<211> LENGTH: 1113
<212> TYPE: DNA
<213> ORGANISM: Artificial Sequence
<220> FEATURE:
<223> OTHER INFORMATION: hCAIX-BBzeta

<400> SEQUENCE: 75

```
atgctgctgc tggtgacctc cctgctgctg tgcgagctgc cccaccccgc tttcctgctg      60

atcccccagg tgcagctggt ggagtccggc ggaggcctgg tgcagcctgg aggaagcctg     120

agactgagct gtagcgcctc cggcaacagc gccaatatct tctcctttgc ttccgtggcc     180

tggtataggc aggcccccgg gaagggcctg gagctggtgt cagtcattac atccgccggc     240

ggcaccaagt acagcgacag cgtgaaaggc cggttcacca tcagcagaga caatagcaag     300

aacacactgt acctgcagat gaatagcctg agagccgagg acaccgccgt gtattactgc     360

aacgtggact acctgcagga ctactggggc cagggcaccc tggtgaccgt gagcagcacc     420

acaacccccg cccccagacc ccctacccca gctcctacca tcgccagcca gcccctgagc     480

ctgagacccg aagcctgccg ccctgctgcc ggaggagctg tgcacaccag aggactggac     540

ttcgcctgtg acatctacat ctgggccccc ctggccggca cctgcggagt gctgctgctg     600

agcctggtga ttaccctgta ctgcaagaga ggcagaaaga aactgctgta catcttcaag     660

cagcccttca tgaggcccgt gcagaccacc caggaagaag acggatgtag ctgccgcttc     720

cccgaagagg aagaaggcgg gtgcgagctg agagtgaaat tctctaggag cgccgacgcc     780

cccgcttacc agcagggaca gaaccagctg tacaacgagc tgaacctggg gagacgggag     840
```

```
gagtatgacg tgctggataa gagaagaggc agagaccccg agatgggagg aaaaccaaga    900

agaaagaacc cacaggaggg cctgtacaac gaactgcaga aggacaagat ggcagaggca    960

tacagcgaga tcggaatgaa gggagagaga agaagaggaa agggacacga cggactgtac   1020

cagggactga gcacagctac aaaggacaca tacgacgcac tgcacatgca ggcactgcca   1080

ccaagagact acaaggacga tgacgacaaa taa                                1113
```

<210> SEQ ID NO 76
<211> LENGTH: 370
<212> TYPE: PRT
<213> ORGANISM: Artificial Sequence
<220> FEATURE:
<223> OTHER INFORMATION: hCAIX-BBzeta

<400> SEQUENCE: 76

```
Met Leu Leu Leu Val Thr Ser Leu Leu Leu Cys Glu Leu Pro His Pro
1               5                   10                  15

Ala Phe Leu Leu Ile Pro Gln Val Gln Leu Val Glu Ser Gly Gly Gly
            20                  25                  30

Leu Val Gln Pro Gly Gly Ser Leu Arg Leu Ser Cys Ser Ala Ser Gly
        35                  40                  45

Asn Ser Ala Asn Ile Phe Ser Phe Ala Ser Val Ala Trp Tyr Arg Gln
    50                  55                  60

Ala Pro Gly Lys Gly Leu Glu Leu Val Ser Val Ile Thr Ser Ala Gly
65                  70                  75                  80

Gly Thr Lys Tyr Ser Asp Ser Val Lys Gly Arg Phe Thr Ile Ser Arg
                85                  90                  95

Asp Asn Ser Lys Asn Thr Leu Tyr Leu Gln Met Asn Ser Leu Arg Ala
            100                 105                 110

Glu Asp Thr Ala Val Tyr Tyr Cys Asn Val Asp Tyr Leu Gln Asp Tyr
        115                 120                 125

Trp Gly Gln Gly Thr Leu Val Thr Val Ser Ser Thr Thr Thr Pro Ala
    130                 135                 140

Pro Arg Pro Pro Thr Pro Ala Pro Thr Ile Ala Ser Gln Pro Leu Ser
145                 150                 155                 160

Leu Arg Pro Glu Ala Cys Arg Pro Ala Ala Gly Gly Ala Val His Thr
                165                 170                 175

Arg Gly Leu Asp Phe Ala Cys Asp Ile Tyr Ile Trp Ala Pro Leu Ala
            180                 185                 190

Gly Thr Cys Gly Val Leu Leu Leu Ser Leu Val Ile Thr Leu Tyr Cys
        195                 200                 205

Lys Arg Gly Arg Lys Lys Leu Leu Tyr Ile Phe Lys Gln Pro Phe Met
    210                 215                 220

Arg Pro Val Gln Thr Thr Gln Glu Glu Asp Gly Cys Ser Cys Arg Phe
225                 230                 235                 240

Pro Glu Glu Glu Glu Gly Gly Cys Glu Leu Arg Val Lys Phe Ser Arg
                245                 250                 255

Ser Ala Asp Ala Pro Ala Tyr Gln Gln Gly Gln Asn Gln Leu Tyr Asn
            260                 265                 270

Glu Leu Asn Leu Gly Arg Arg Glu Glu Tyr Asp Val Leu Asp Lys Arg
        275                 280                 285

Arg Gly Arg Asp Pro Glu Met Gly Gly Lys Pro Arg Arg Lys Asn Pro
    290                 295                 300

Gln Glu Gly Leu Tyr Asn Glu Leu Gln Lys Asp Lys Met Ala Glu Ala
```

-continued

```
305                 310                 315                 320

Tyr Ser Glu Ile Gly Met Lys Gly Glu Arg Arg Arg Gly Lys Gly His
                325                 330                 335

Asp Gly Leu Tyr Gln Gly Leu Ser Thr Ala Thr Lys Asp Thr Tyr Asp
            340                 345                 350

Ala Leu His Met Gln Ala Leu Pro Pro Arg Asp Tyr Lys Asp Asp Asp
        355                 360                 365

Asp Lys
    370
```